(12) United States Patent
Murray

(10) Patent No.: US 6,559,358 B1
(45) Date of Patent: May 6, 2003

(54) PLANTS WITH MODIFIED GROWTH

(75) Inventor: James Augustus Henry Murray, Cambridge (GB)

(73) Assignee: Cambridge University Technical Services, Ltd., Cambridge (GB)

( * ) Notice: Subject to any disclaimer, the term of this patent is extended or adjusted under 35 U.S.C. 154(b) by 0 days.

(21) Appl. No.: 09/404,296

(22) Filed: Sep. 24, 1999

Related U.S. Application Data

(63) Continuation of application No. PCT/EP98/01701, filed on Mar. 24, 1998.

(30) Foreign Application Priority Data

Mar. 26, 1997 (EP) .............................................. 97302096

(51) Int. Cl.⁷ ........................ C12N 15/29; C12N 15/82; A01H 5/00
(52) U.S. Cl. .................... 800/290; 800/298; 435/320.1; 435/419
(58) Field of Search ................................ 800/298, 290; 435/419, 468, 320.1

(56) References Cited

FOREIGN PATENT DOCUMENTS

| WO | WO9209685 | 6/1992 |
|----|-----------|--------|
| WO | WO9315213 | 8/1993 |
| WO | WO9747745 | 12/1997 |
| WO | WO9803631 | 1/1998 |

OTHER PUBLICATIONS

Cockcroft et al, "Cyclin D control of growth rate in plants", Jun. 2000, Nature vol. 405 pp. 575–579.*

Riou–Khamlichi et al, "Cytokinin Activiation of Arabidopsis Cell Division Through a D–Type Cyclin", Mar. 1999, Science vol. 283, ppp. 1541–1544.*

Nature Biotechnology 15(Mar. 1997) 244–247 Holmberg et al. "Transgenic tobacco expressing Vitreoscilla hemoglobin . . . ".

Nature 380 (Apr. 11, 1996) 520–23 Doerner et al. "Control of root growth and development by cyclin expression".

Plant Molecular Biology 32 (1996) 1003–18 Renaudin et al "Plant cyclins: a unified nomenclature for plant A–, B– and D–type . . . ".

Proc Natl Acad Sci USA 93 (Aug. 1996) 8962–67 Grafi et al "A maize cDNA encoding a member of the retinoblastoma . . . ".

Current Biology 6(7) 1996 788–89 Doonan, J "Plant growth: roots in the cell cycle".

The EMBO Journal 15(18) 1966, 4900–908 Xie et al "Plant cells contain a novel membe of the retinoblastoma family . . . ".

The Plant Cell 7 (Nov. 1995) 1847–57 Dahl et al "The D–type alfalfa cyclin gene cycMs4 compliments . . . ".

The Plant Cell 7 (Jan. 1995) 85–103 Soni et al "A family of cyclin D homologs from plants differentially . . . ".

The EMBO Journal of 14(16) 1995, 3925–36 Hemerly et al "Dominant negative mutants of the Cdc2 kinase uncouple cell division from iterative plant development".

Plant Molecular Biology 23 (1993) 445–451 Bell et al "Tobacco plants transformed with cdc25, a mitotic inducer gene from fission yeast".

The Plant Journal 2(5) 1992, 799–807 Kamada et al "Transgenic tobacco plants expressing rgp1, a gene encoding . . . ".

* cited by examiner

*Primary Examiner*—Elizabeth F. McElwain
*Assistant Examiner*—Cynthia Collins
(74) *Attorney, Agent, or Firm*—Leonard S. Svensson; Birch, Stewart, Kolasch & Birch, LLP

(57) ABSTRACT

A process is provided for modifying growth or architecture of plants by altering the level or the functional level of a cell division controlling protein, preferably a cell-division controlling protein that binds phosphorylates retinoblasoma-link proteins, more preferably a cyclin, particularly a D-type cyclin within cells of a plant. Also provided are chimeric genes comprising a transcribed DNA region encoding an RNA or a protein, which when expressed either increases or decreases the level or functional level of a cell-division controlling protein, and plant cells and plants expressing such chimeric genes.

7 Claims, No Drawings

PLANTS WITH MODIFIED GROWTH

This application is a Continuation of PCT International Application No. PCT/EP98/01701 filed on Mar. 24, 1998, which designated the United States and on which priority is claimed under 35 U.S.C. § 120, the entire contents of which are hereby incorporated by reference.

This invention relates to the use of cell-division controlling proteins or parts thereof, preferably cell-division controlling proteins that bind retinoblasoma-like proteins, more preferably cyclins, particularly D-type cyclins and genes encoding same, for producing plants with modified phenotypes, particularly plants with modified growth rates or plants comprising parts with modified growth rates and/or modified relative sizes or plants with modified architecture. This invention also relates to plant cells and plants expressing such DNAs.

BACKGROUND TO THE INVENTION

All eukaryotic cells undergo the same sequential series of events when they divide, and the term "cell cycle" reflects the ordered nature and universality of these events. In the eukaryotic cell cycle DNA replication (S) and cell division (M) are normally temporally separated by "gap" phases (G1 and G2) in the sequence G1-S-G2-M. This arrangement allows entry to the critical processes of DNA replication and mitosis to be precisely controlled. Underlying the cytological events of the cell cycle is an ordered series of temporally and spatially organised molecular and cellular processes which define the direction and order of the cycle. Cell cycle progression appears to be regulated in all eukaryotes by major controls operating at the G1-to-S phase and G2-to-M phase boundaries. Passage through these control points requires the activation of cyclin-dependent kinases (CDKs), whose catalytic activity and substrate specificity are determined by specific regulatory subunits known as cyclins and by interactions with other proteins that regulate the phosphorylation state of the complex (reviewed in Atherton-Fessier et al., 1993; Solomon, 1993). In budding and fission yeasts, both the G1-to-S and G2-to-M phase transitions are controlled by a single CDK, encoded by the cdc2+ gene in *Schizosaccharomyces pombe* and by CDC28 in *Saccharomyces cerevisiae*. The association of $p34^{cdc2}$ ($p34^{CDC28}$ in budding yeast) with different cyclin partners distinguishes the two control points (reviewed in Nasmyth, 1993). In mammalian cells, a more complex situation prevails, with at least six related but distinct CDKs (encoded by cdc2/cdk1, cdk2, cdk3, cdkain 4, cdk5, and cdk6) having distinct roles, each in conjunction with one or more cognate cyclin partners (Fang and Newport, 1991; Meyerson et al., 1991, 1992; Xiong et al., 1992b; Tsai et al., 1993a; van den Heuvel and Harlow, 1993; Meyerson and Harlow, 1994). B-type cyclins are the major class involved in the G2-to-M transition and associate with $p34^{cdc2}$ or its direct homologs (reviewed in Nurse, 1990). Cyclin B is one of two cyclins originally described as accumulating in invertebrate eggs during interphase, and rapidly destroyed in mitosis (Evans et al., 1983), and it is a component of Xenopus maturation-promoting factor (Murray et al., 1989). Subsequently, cyclin B homologs have been identified from many eukaryotic species. Cyclin A is also of widespread occurrence in multicellular organisms, and its precise role is unclear, although its peak of abundance suggests a function in S phase (reviewed in Pines, 1993).

The G1-to-S phase transition is best understood in *S. cerevisiae*. Genetic studies define a point late in G1 called START. After passing START, cells are committed to enter S phase and to complete a full additional round of division, which will result in two daughter cells again in G1 phase (Hartwell, 1974; reviewed in Nasmyth, 1993). The products of three *S. cerevisiae* G1 cyclin genes called CLN1, CLN2, and CLN3 are the principal limiting components for passage through START (Richardson et al., 1989; Wittenberg et al., 1990; Tyers et al., 1993). Transcription of CLN1 and CLN2 is activated in G1, and accumulation of their protein products to a critical threshold level by a positive feedback mechanism leads to activation of the $p34^{CDC28}$ kinase and transition through START (Dirick and Nasmyth, 1991). The G1 cyclins are then degraded as a consequence of PEST motifs in their primary sequence that appear to result in rapid protein turnover (Rogers et al., 1986; Lew et al., 1991; reviewed in Reed, 1991).

The *S. cerevisiae* G1 cyclins are at least partially redundant, because yeast strains in which two of the three G1 cyclin genes are deleted and the third placed under the control of a galactose-regulated promoter show a galactose-dependent growth phenotype. Such strains have been used to identity Drosophila and human cDNA clones that rescue this conditional cln-deficient phenotype on glucose plates when the single yeast CLN gene present is repressed (Koff et al., 1991; Lahue et al., 1991; Leopold and O'Farrell, 1991; Lew et al., 1991; Xiong et al., 1991). Human cDNAs encoding three new classes of cyclins, C, D, and E, were identified by this means. Although these cyclins show only limited homology with the yeast CLN proteins, they have proved important for understanding controls that operate in mammalian cells during G1 and at the restriction point at the G1-to-S phase boundary (Pardee, 1989; Matsushime et al., 1992; Koff et al., 1992, 1993; Ando et al., 1993; Quelle et al., 1993; Tsai et al., 1993b). Cyclin E may act as a rate-limiting component at the G1-to-S phase boundary (Ohtsubo and Roberts, 1993; Wimmel et al., 1994), whereas the dependency of cyclin D levels on serum growth factors (Matsushime et al., 1991; Baldin et al., 1993; Sewing et al., 1993) suggests that cyclins of the D-type may form a link between these signals and cell cycle progression.

An important factor involved in the regulation of cell cycle progression in mammals is the retinoblastoma susceptibility gene encoding the retinoblastoma protein (Rb). Rb binds and inactivates the E2F family of transcription factors, and it is through this ability that Rb exerts most of its potential to restrain cell division in the G1-phase. E2F transcription factors are known to switch on cyclin E and S-phase genes and the rising levels off cyclin E and/or E2F lead to the onset of replication (Nevins, 1992, Johnson et al., 1993). The ability of Rb to inactivate E2F depends on its phosphorylation state. During most of G1, Rb is in a hypophosphorylated state, but in late G1 phase, phosphorylation of Rb is carried out by cyclin-dependent kinases particularly CDK4 complexed to its essential regulatory subunit, cyclin D (Pines, 1995) and CDK2 complexed to cyclin E (at the G1/S boundary) or cyclin A (in S phase). These multiple phosphorylations of Rb cause it to release E2F, which can then, ultimately promote transcription of the S-phase genes.

Plant cells were used in early studies of cell growth and division to define the discrete phases of the eukaryotic cell cycle (Howard and Pelc, 1953), but there is a paucity of data on molecular cell cycle control in plant systems. Plant cells that cease dividing in vivo due to dormancy, or in vitro due to nutrient starvation, arrest at principal control points in G1 and G2 (van't Hof and Kovacs, 1972; Gould et al., 1981; reviewed in van't Hof, 1985); this is in general agreement with the controls operating in other eukaryotic systems.

Although mature plant cells may be found with either a G1 or a G2 DNA content (Evans and van't Hof, 1974; Gould et al., 1981), the G1 population generally predominates. The G1 control point is found to be more stringent in cultured plant cells subjected to nitrogen starvation; these cells arrest exclusively in G1 phase (Gould et al., 1981). Strong analogies thus exist between the principal control point in G1 of the plant cell cycle, the START control in yeasts, and the restriction point of mammalian cells.

Antibodies or histone HI kinase assays have been used to indicate the presence and localization of active CDC2-related kinases in plant cells (John et al., 1989,1990, 1991; Mineyuki et al., 1991; Chiatante et al., 1993; Colasanti et al., 1993; reviewed in John et al., 1993), and cDNAs encoding functional homologs of CDC2 kinase have been isolated by reduced stringency hybridization or redundant polymerase chain reaction from a number of plant species, including pea (Feiler and Jacobs, 1990), alfalfa (Hirt et al., 1991, 1993), Arabidopsis (Ferreira et al., 1991; Hirayama et al., 1991), soybean (Miao et al., 1993), Antirrhinum (Fobert et al., 1994), and maize (Colasanti et al., 1991). A number of cDNA sequences encoding plant mitotic cyclins with A- or B-type characteristics or having mixed A- and B-type features have also been isolated from various species, including carrot (Hata et al., 1991), soybean (Hata et al., 1991), Arabidopsis (Hemerly et al., 1992; Day and Reddy, 1994), alfalfa (Hirt et al., 1992), Antirrhinum (Fobert et al., 1994), and maize (Renaudin et al., 1994).

Soni et al. (1995) identified a new family of three related cyclins in Arabidopsis by complementation of a yeast strain deficient in G1 cyclins. Individual members of this family showed tissue specific expression and are conserved in other plant species.

They form a distinctive group of plant cyclins and were named δ-type cyclins to indicate their similarities with mammalian D-type cyclins. The sequence relationships between δ and D cyclins include the N-terminal sequence LxCxE. The leucine is preceded at position −1 or −2 by an amino acid with an acidic side chain (D, E). This motif was originally identified in certain viral oncoproteins and is strongly implicated in binding to the retinoblastoma protein. By analogy to mammalian cyclin D, these plant homologs may mediate growth and phytohormonal signals into the plant cell cycle. In this respect it was shown that, on restimulation of suspension-cultured cells, cyclin δ3 was rapidly induced by the plant growth regulator cytokinin and cyclin δ2 was induced by carbon source. Renaudin et al. (1996) defined the groups and nomenclature of plant cyclins and δ-cyclins are now called CycD cyclins.

Dahl et al. (1995) identified in alfalfa a cyclin (cycMs4) related to δ3 in alfalfa.

Recently, Rb-like proteins were identified in plant. Both Xie et al. (1996) and Grafi et al. (1996) describe the isolation and preliminary characterization of an Rb homologue from maize.

Doerner et al. (1996) describe the ectopic expression of a B-type cyclin (cyc1At from Arabidopsis) under control of a promoter from the cdc2a gene, in Arabidopsis. The "cdc2a" transgenic plants expressing the transgene strongly had a markedly increased root growth rate. Moreover, growth and development of lateral roots was accelerated following induction with indoieacetic acid in the transgenic plants relative to the control plants.

Hemerly et al. (1995) describe transgenic tobacco and Arabidopsis plants expressing wild type or dominant mutations of a kinase operating at mitosis (CDC2a). Plants constitutively overproducing the wild-type CDC2a or a mutant form predicted to accelerate the cell cycle did not exhibit a significantly altered development. A mutant CDC2a, expected to arrest the cell cycle, abolished cell division when expressed in Arabidopsis. Some tobacco plants constitutively producing the latter mutant kinase, were recovered. These plants contained considerably fewer but larger cells.

PCT patent publication "WO" 92/09685 describes a method for controlling plant cell growth comprising modulating the level of a cell cycle protein in a plant for a time and under conditions sufficient to control cell division. The preferred protein, identified in the examples, is a $p34^{cdc2}$ kinase or the like operating at mitosis.

WO93/12239 describes plants with altered stature and other phenotypic effects, particularly precocious flowering and increased numbers of flowers by transformation of the plant genome with a cdc25 gene from a yeast such as *Schizosaccharomyces pombe*.

WO97/47647 relates to the isolation and characterization of a plant DNA sequence coding for a retinoblastoma protein, the use thereof for the control of the growth in plant cells, plants and/or plant viruses as well as the use of vectors, plants, or animals or animal cells modified through manipulation of the control route based on the retinoblastoma protein of plants.

U.S. Pat. No. 5,514,571 discloses the use of cyclin D1 as a negative regulator of mammalian cell proliferation. Overexpression of cyclin D1 blocks mammalian cell growth, while blocking cyclin D1 expression promotes cell proliferation.

SUMMARY OF THE INVENTION

The invention provides a process to obtain a plant with altered growth characteristics or altered architecture, particularly plants with reduced or increased growth rate, plants which require less time to flower or plants with an increased number of flowers per plant, or plant with an increased size of an organ comprising the step of altering the level or the functional level of a cell-division controlling protein, capable of binding and/or phosphorylating an Rb-like protein, preferably a cell-division controlling protein comprising an LxCxE binding motif or related motif, preferably in the N-terminal part of the protein, particularly a D-type cyclin, within the cells of a plant.

Also provided is a process to obtain a plant with altered growth characteristics or altered architecture comprising the step of altering the level or functional level of the cell-division controlling protein by integrating a chimeric gene into the genome of the cells of the plant, comprising the following operably linked DNA fragments:

a) a plant expressible promoter region, particularly a CaMV35S promoter region, b) a transcribed DNA region encoding an RNA or a protein, which when expressed, either increases or decreases the level or the functional level of the cell-division controlling protein; and optionally c) a 3' end formation and polyadenylation signal functional in plant cells.

In accordance with the invention, the transcribed DNA region encodes an antisense RNA, a ribozyme, or a sense RNA strand which when expressed reduces, inhibits or prevents the expression of a cell-division controlling protein particularly an endogenous D-type cyclin.

Further in accordance with the invention the transcribed DNA encodes a cell-division controlling protein capable of binding the pocket domain of an Rb-like protein, preferably a cell-division controlling protein comprising an LxCxE binding motif, more preferably a D-type cyclin, particularly a D-type cyclin from plants, more particularly a D-type cyclin is selected from group of *Arabidopsis thaliana* CYCD1, *Arabidopsis thaliana* CYCD2, *Arabidopsis thaliana* CYCD3, *Nicotiana tabacum* CYCD2;1, *Nicotiana tabacum* CYCD3;1, *Nicotiana tabacum* CYCD3;2, *Helianthus tuberosus* CYCD1;1, *Zea mays* CYCD2 and *Helianthus tuberosus* CYCD3;1.

Also in accordance with the invention the transcribed RNA encodes a protein or peptide which, when expressed, increases said functional level of said cell division controlling protein, particularly a protein or peptide selected from: a mutant D-type cyclin, a part of a D-type cyclin, a D-type cyclin which has a mutation in the cyclin box, a D2-type cyclin which has a substitution of amino acid 185 or amino acid 155, a D2-type cyclin which has mutation E185A or K155A, a D-type cyclin wherein the PEST sequences are removed, a D-type cyclin wherein the LxCxE binding motif has been changed or deleted, or a D-type cyclin wherein the C-residue from the LxCxE binding motif has been deleted.

It is also an object of the invention to provide such chimeric genes.

Further provided are plant cells, plants and seed thereof, comprising the chimeric genes of the invention and having altered growth characteristics and/or altered architecture.

Another object of the invention is to provide the use of a cell-division controlling protein, capable of binding the pocket domain of an Rb-like protein and/or capable of phosphorylating an Rb-like protein, particularly a cell-division controlling protein comprising an LxCxE binding motif in the N-terminal part of the protein, more particularly a D-type cyclin and genes encoding same, to alter the growth characteristics or architecture of a plant. The cell-division controlling protein is preferably encoded by a chimeric gene, integrated in the genome of the cells of a plant.

DETAILED DESCRIPTION OF THE INVENTION

As used herein "architecture" of a plant refers to the general morphology as defined by the relative sizes, positions and number of the several parts of a plant (i.e., organs such as but not limited to leaves, inflorescences, storage organs such as tubers, roots, stems, flowers, or parts of organs such as petals, sepals, anthers, stigma, style, petiole and the like). "Altering the architecture of a plant" thus refers to changes in the general morphology as the result of changing e.g., the number, size and position of organs or parts of organs. It is clear that altering either one organ or part of an organ or several organs or parts of organs, as described, will result in an altered plant architecture. This can be achieved by altering (i.e., enhancing or reducing) cell division activity in existing meristems and/or organ primordia or by creating de novo meristems.

As used herein, "co-suppression" refers to the process of transcriptional and/or post-transcriptional suppression of RNA accumulation in a sequence specific manner, resulting in the suppresion of expression of homologous endogenous genes or transgenes. Suppressing the expression of an endogenous gene can be achieved by introduction of a transgene comprising a strong promoter operably linked to a DNA region whereby the resulting transcribed RNA is a sense RNA comprising a nucleotide sequence which is has at least 75%, preferably at least 80%, particularly at least 85%, more particularly at least 90%, especially at least 95% to the coding or transcribed DNA sequence (sense) of the gene whose expression is to be suppressed. Preferably, the transcribed DNA region does not code for a functional protein. Particularly, the transcribed region does not code for a protein.

As used herein, the term "plant-expressible promoter" means a promoter which is capable of driving transcription in a plant cell. This includes any promoter of plant origin, but also any promoter of non-plant origin which is capable of directing transcription in a plant cell, e.g., certain promoters of viral or bacterial origin such as the CaMV35S or the T-DNA gene promoters.

The term "expression of a gene" refers to the process wherein a DNA region under control of regulatory regions, particularly the promoter, is transcribed into an RNA which is biologically active i.e., which is either capable of interaction with another nucleic acid or protein or which is capable of being translated into a biologically active polypeptide or protein. A gene is said to encode an RNA when the end product of the expression of the gene is biologically active RNA, such as e.g., an antisense RNA or a ribozyme. A gene is said to encode a protein when the end product of the expression of the gene is a biologically active protein or polypeptide.

The term "gene" means any DNA fragment comprising a DNA region (the "transcribed DNA region") that is transcribed into a RNA molecule (e.g., an mRNA) in a cell under control of suitable regulatory regions, e.g., a plant-expressible promoter. A gene may thus comprise several operably linked DNA fragments such as a promoter, a 5' leader sequence, a coding region, and a 3' region comprising a pqlyadenylation site. An endogenous plant gene is a gene which is naturally found in a plant species. A chimeric gene is any gene which is not normally found in a plant species or, alternatively, any gene in which the promoter is not associated in nature with part or all of the transcribed DNA region or with at least one other regulatory region of the gene.

This invention is based on the unexpected finding that chimeric genes comprising DNA encoding a cell-division controlling protein capable of binding an Rb-like protein, particularly a plant cyclin of the D-type, under control of a plant-expressible promoter could be stably integrated in the genome of plant cells, without deleterious effects, and furthermore that the increased expression of such a cell-division controlling protein, particularly a cyclin of the D-type, in the plant cells led to specific alterations in the growth rate and architecture of the resulting transformed plants.

Thus, the invention relates to modulating the level of expression or activity of functional cell-division controlling proteins, preferably in a stable mannner, within plant cells of a plant to alter the architecture or the growth rate or both of the transformed plant and its progeny. Conveniently, the level or functional level of cell-division controlling proteins is controlled genetically by altering the expression of genes encoding these cell-division controlling proteins. Increasing the level or functional level of a cell-division controlling protein genetically can be achieved e.g., by manipulating the copy number of the encoding gene(s), by altering the promoter region of the encoding genes or by manipulation of the genes regulating directly or indirectly the level of the expression of a cell-division controlling protein. Alternatively, the level of a cell-division controlling protein can be increased by stabilizing the mRNA encoding the cell-division controlling protein, or by stabilizing the cell-division controlling protein e.g., by removal of destruction motifs or so-called PEST sequences.

The functional level or activity of cell-division controlling protein can be increased by the decreasing the level of an antagonist or an inhibitor of the cell-divsion promoting protein, through techniques such as, but not limited to, providing the cell with a protein, such as an inactive cell-division controlling protein similar to the one whose functional level is to be increased, or part of a such a cell-division controlling protein, which is still capable of binding an inhibitor or other regulatory protein, or is still capable of binding to cyclin-dependent kinases. The functional level or activity of cell-division controlling protein can also be increased by alteration or mutation of the cell-division controlling protein to reduce or elimate binding of an antagonist or inhibitor of the activity of the cell division related protein.

Reducing the functional level of a cell-division controlling protein can be achieved e.g., by decreasing the mRNA pool encoding the cell-division controlling protein that is available for translation, through techniques such as, but not limited to, antisense RNA, ribozyme action or co-suppresion. Alternatively, the functional level of of cell-division controlling protein can be decreased by the increasing the level of an antagonist or an inhibitor of the cell-divsion promoting protein.

For the purpose of this invention, a "cell-division controlling protein" is a polypeptide or protein which is required for the regulation of the progression through the cell cycle of a eukaryotic cell, preferably a plant cell, or a protein which can effect the entry of cells into the cell cycle or affect progression of cells through the cell cycle by direct interaction with a protein required for the regulation of progression through the cell cycle, or a polypeptide or protein which can assume an equivalent function but is not required for the regulation of the cell cycle.

Suitable cell-division controlling proteins are proteins capable of phosphorylating either alone or in combination with other proteins an Rb-like protein, preferably capable of phosphorylating an Rb-like protein in a plant cell in the G1-S transition phase, or are capable of binding the pocket domain of retinoblastoma-like (Rb-like) proteins, preferably proteins having an LxCxE binding motif comprised within the amino-acid sequence or a related motif such as LxSxE or FxCxE (binding motifs are represented in the one-letter amino acid code wherein x represents any amino-acid). Particularly preferred are cyclins which comprise the LxCxE binding motif (and/or related motif) in the N-terminal half of the protein, preferably within the first 50 amino acid residues, particularly within the first 30 amino acid residues, such as the cyclins of the D-type, particularly plant cyclins of the D-type, especially a cyclin from the group of *Arabidopsis thaliana* CYCD1, *Arabidopsis thaliana* CYCD2, *Arabidopsis thaliana* CYCD3, *Nicotiana tabacum* CYCD3;1, *Nicotiana tabacum* CYCD2;1, *Nicotiana tabacum* CYCD3;2, *Helianthus tuberosus* CYCD1;1, *Zea mays* CYCD2 and *Helianthus tuberosus* CYCD3;1 or a cyclin with essentially similar protein sequences.

The mentioned plant cyclins of the D-type are fully characterized by the amino acid sequence encoded by the DNA sequence of EMBL Accession No X83369 (hereinafter, may be referred to as SEQ ID NO: 27) from the nucleotide position 104 to the nucleotide position 1108 for *Arabidopsis thaliana* CYCD1, EMBL Accession No X83370 (hereinafter, may be referred to as SEQ ID NO:29) from the nucleotide position 195 to the nucleotide position 1346 for *Arabidopsis thalina* CYCD2, EMBL Accession No X83371 (hereinafter, may be referred to as SEQ ID NO:31) from the nucleotide position 266 to the nucleotide position 1396 for *Arabidopsis thaliana* CYCD3, the nucleotide sequence of SEQ ID NO: 1 from nucleotide position 182 to nucleotide position 1243 for *Nicotiana tabacum* CYCD2;1, the nucleotide sequence of SEQ ID NO:3 from nucleotide position 181 to nucleotide position 1299 for *Nicotiana tabacum* CYCD3;1, the nucleotide sequence of SEQ ID NO:5 from nucleotide position 198 to nucleotide position 1298 for *Nicotiana tabacum* CYCD3;2, the nucleotide sequence of SEQ ID NO:7 from nucleotide position 165 to nucleotide position 1109 for *Helianthus tuberosus* CYCD1;1, the nucleotide sequence of SEQ ID NO:9 from nucleotide position 48 to nucleotide position 1118 for *Helianthus tuberosus* CYCD3;1 and the nucleotide sequence of SEQ ID NO:26 from nucleotide position 316 to nucleotide position 1389 for *Zea mays* CYCD2.

It is thought that increasing, respectively decreasing, the level or the functional level or the activity of these cell-division controlling proteins accelerates, respectively delays, the transition of G1 to the S-phase in plant cells, or increases, respectively decreases, the proportion of actively dividing cells, by their interaction with Rb-like proteins affecting the ability of the Rb-like protein to inactivate certain transcription factors. It is further thought that expression of these cell-division controlling proteins interacting with Rb-like proteins effectively allows the cells to initiate division processes, whereas (over)expression of G2/mitotic cyclins (such as cyclins of the B-type or the cdc25 gene product) is in contrast expected to lead to faster progression through the G2/mitotic phases of cell cycles already started.

For the purpose of this invention "Rb-like proteins" are defined as proteins from the group of human Rb-1 protein (Lee et al. 1987; Accession no P06400), human p107 (Ewen et al., 1991; Accession no L14812) and human p130 (Hannon et al.1993; Accession A49370), Drosophila RBF (Du et al., 1996; Accession no for DNA entry of the encoding gene X96975), mouse RB (Bemards et al. 1989; Accession no P13405) chicken RB (Boehmelt et al., 1994; Accession no X72218), Xenopus Rb (Destree et al. 1992; Accession A44879), ZmRb and Rb1 from *Zea mays* (Xie et al., 1996; Grafi et al. 1996; Accession numbers for DNA entry of the encoding genes: X98923; GenBank U52099) as well as any protein that has simultaneously at least 25–30% amino acid sequence similarity (identity) to at least three members of the above-mentioned group, and comprises the conserved cysteine residue located at position 706 of human Rb-1 or at equivalent positions in the other Rb-like proteins (see e.g., Xie et al. 1996).

Rb-like proteins are members of a small family known as "pocket proteins". This term is derived from a conserved bipartite domain, the so-called "pocket domain", which is the binding site for several growth control proteins such as E2F family of transcription factors, D-type cyclins and viral oncoproteins. The A and B subdomains of the pocket domain are more conserved than the rest of the protein (~50–64% for the A and B subdomains) and are separated by a non-conserved spacer. Pocket domains are located between amino acids at positions 451 and 766 for human Rb, 321 to 811 for human p107, 438 to 962 for human p130, 445 to 758 for mouse RB, 441 to 758 for chicken RB, 440 to 767 for Xenopus Rb, 11 to 382 for com ZmRb, 89 to 540 for com Rb1.

For the purpose of the invention "binding to an Rb-like protein" or "binding to the pocket domain of an Rb-like protein" can be analyzed by either an in vitro assay or one of the in vivo assays, or a combination thereof. In the in vitro assay, the binding is analyzed between the protein in question which has been labelled by $^{35}$S-methionine, and a fusion protein of glutathione-S-transferase (GST) and the pocket domain of an Rb-like protein, such as the human Rb. The fusion to GST allows easy purification and fixation of the fusion protein on glutathione sepharose beads. The interaction between the assayed protein and the Rb-like protein is compared to the binding between the same protein and a fusion protein of GST and an Rb-like protein with a mutation in the conserved cysteine at a position equivalent to cysteine 706 in human Rb, such as human Rb C706F. Such an assay has been described e.g., by Dowdy et al. (1993) and Ewen et al. (1993). In a variant of this assay, the Rb-like protein can be expressed in baculovirus-infected insect cells (Dowdy et al., 1 993). In a further variant, both the Rb-like protein and Rb-binding protein can be co-expressed in insect cells, and association detected by gel-filtration or co-immunoprecipitation (O'Reilly et al., 1992).

An in vivo assay which can be used to determine the binding of a protein to the pocket domain of Rb-like proteins, is the yeast two-hybrid system (Fields and Song, 1989). This analysis relies on the ability to reconstitute a functional GAL4 activity from two separated GAL4 fusion proteins containing the DNA binding domain (GAL4$^{BD}$) and the activation domain (GAL4$^{AD}$) fused to a pocket domain of an Rb-like protein and the protein to be assayed respectively. Expression plasmids comprising chimeric genes encoding these fusion proteins are introduced into a yeast strain encoding appropriate GAL4 inducible markers, such as strain HF7c (Feilloter et al., 1994) containing GAL4-inducible HIS3 and LacZ markers, or strain Y190 (Harper et al., 1993). Proteins binding to the pocket domain of the Rb-like protein will allow growth in the absence of histidine. An example of a two-hybrid assay to demonstrate interaction of a protein with an Rb-like protein has been described by Durfee et al. (1993).

Preferably, suitable control experiments should be included, such as separate introduction into the same yeast strain of the expression plasmids, or introduction of expression plasmids encoding fusion proteins containing the DNA binding domain (GAL4$^{BD}$) and the activation domain (GAL4$^{AD}$) fused to a mutated pocket domain of an Rb-like protein, preferably mutated at the C706 or equivalent positions and the protein to be assayed respectively.

An alternative in vitro assay to determine the binding of a protein to the pocket domain of Rb-like proteins comprises transient expression of both proteins in plant cells, preferably tobacco protoplasts, and immunoprecipitation using an antibody directed against one of the two proteins to measure co-precipitation of the other protein.

For the purpose of the invention "phosphorylating an Rb-like protein" can be analyzed by an in vitro assay relying on the use of gamma $^{32}$P-labeled adenosine-triphosphate to monitor the capacity of a protein (or a combination of proteins such as cyclins and cyclin dependent kinases) to transfer the labeled phosphate group to a target protein, as known in the art.

For the purpose of the invention "cyclin" can be defined as a regulatory protein, comprising a protein domain of about 100 amino acids known as the "cyclin box". The cyclin box is the binding site for cyclin-dependent kinases, allowing the cyclin to exert its regulatory effect on the kinase activity of the CDKs.

A cyclin box can be identified by comparing the amino acid sequence of the protein with known cyclin boxes, such as the amino acid sequence between positions 81–186 of CYCD1 from *Arabidopsis thaliana*, between positions 96–201 of CYCD2 from *Arabidopsis thaliana*, between positions 86–191 of CYCD3 from *Arabidopsis thaliana*, the cyclin boxes described by Renaudin et al. (1994; 1996), by Soni et al. (1995), and by Hemerly et al. (1992). An amino acid sequence identified as a cyclin box on the basis of sequence comparison should posses at least the five conserved residues required for cyclin activity R(97), D(126), L (144), K(155), E(185) (indicated positions are from the sequence of CYCD2 from *Arabidopsis thaliana*) at equivalent positions. (see e.g., Soni et al. (1995) and Renaudin et al. (1996).

D-type cyclins (cyclin D or CycD) are cyclins that are characterized by the presence of additional characteristic sequences, such as the LxCxE motif or related motifs for binding Rb-like proteins, which is found within the N-terminal part of the protein, preferably located between the N-terminus and the cyclin box, particularly within the first 50 amino acids, more particularly within the first 30 amino acids of the initiating methionine-residue. Preferably, the leucine of the binding motif is preceded at position −1 or −2 by an amino acid with an acidic side chain (D, E). Alternative binding motifs such as LxSxE or FxCxE can be found. Indeed, Phelps et al. (1992) have identified that mutating the binding motif LxCxE in human papillomavirus E7 to LxSxE does not affect the ability of the protein to bind Rb-like proteins. Three groups of D-type cyclins have been identified on the basis of sequence homology: CycD1 (comprising *Arabidopsis thaliana* CycD1 and *Helianthus tuberosus* CYCD1;1) CycD2 (comprising *Arabidopsis thaliana* CYCD2, *Nicotiana tabacum* CYCD2;1, *Zea mays* CYCD2), CycD3 (comprising *Arabidopsis thaliana* CYCD3, *Nicotiana tabacum* CYCD3;1, *Nicotiana tabacum* CYCD3;2, and *Helianthus tuberosps* CYCD3;1).

Nomenclature and consensus sequences for the different types and groups of plant cyclins, including cyclins of the D-type, have been described by Renaudin et al. (1996) and can be used to classify new cyclins based on their amino acid sequence.

For the purpose of the invention, the cell-division controlling proteins can be provided to the cells either directly, e.g., by electroporation of the protoplasts in the presence of the cell-division controlling proteins, or indirectly, by transforming the plant cells with a plant-expressible chimeric gene encoding the protein to be tested either transiently, or stably integrated in the genome of the protoplasts.

In one aspect of the invention the level or the functional level of the cell-division controlling protein, capable of phosphorylating an RB-like protein or binding the pocket domain of an Rb-like proteins, is increased, to obtain a plant with altered growth rate or architecture, by integrating a chimeric gene into the genome of the cells of the plant, comprising the following operably linked DNA fragments:

a) a plant-expressible promoter region, particularly a CaMV35S promoter region,
  b) a transcribed DNA region encoding a protein, which when expressed, increases the level or the functional level of the cell-division controlling protein; and optionally
  c) a 3' end formation and polyadenylation signal functional in plant cells.

In a preferred embodiment of the invention, the expression level of cyclin D is increased by introduction into the genome of a plant cell, a chimeric gene comprising a transcribed DNA region encoding a cyclin D, under control of a plant-expressible promoter. The transcribed DNA region preferably comprises a nucleotide sequence selected from the nucleotide sequence of EMBL Accession No X83369 (SEQ ID NO:27) from the nucleotide position 104 to the nucleotide position 1108, the nucleotide sequence of EMBL Accession No X83370 (SEQ ID NO:29) from the nucleotide position 195 to the nucleotide position 1346, the nucleotide sequence of EMBL Accession No X83371 (SEQ ID NO:31) from the nucleotide position 266 to the nucleotide position 1396, the nucleotide sequence of SEQ ID NO:1 from nucleotide position 182 to nucleotide position 1243, the nucleotide sequence of SEQ ID NO:3 from nucleotide position 181 to nucleotide position 1299, the nucleotide sequence of SEQ ID NO:5 from nucleotide position 198 to nucleotide position 1298, the nucleotide sequence of SEQ ID NO:7 from nucleotide position 165 to nucleotide position 1109, the nucleotide sequence of SEQ ID NO:9 from nucleotide position 48 to nucleotide position 1118 or the nucleotide sequence of SEQ ID NO:26 from nucleotide position 316 to nucleotide position 1389 for *Zea mays* CYCD2.

In a particularly preferred embodiment the expression level of a cyclin of the CycD2 type is altered (i.e., increased) by introduction into the genome of a plant cell, of a "chimeric cycD2 gene" comprising a transcribed DNA region encocding a cyclin of the CycD2 type, under control of a plant-expressible promoter, preferably a constitutive promoter, particularly a CaMV35S promoter, such as the chimeric cycD2 gene of plasmid pCEC1, in order to alter the morphology, architecture and growth characteristics of the transgenic plant, particularly to increase the vegetative growth of the transgenic plant, more particularly to alter the growth rate of the transgenic plant.

For the purpose of the invention, "increase" or "decrease" of a measurable phenotypic trait is quantified as the difference between the mean of the measurements pertinent to the description of that trait in different plants of one transgenic plant line, and the mean of the measurements of that trait in wild type plants, divided by the mean of the measurements of that trait in wild type plants, expressed in percentage, whereby transgenic and control (wild type) plants are grown under the same conditions of nutrient supply, light, moisture, temperature and the like, preferably under standardized conditions. Prefered levels of increase or decrease are statistically significant, preferably at the 0.05 confidence level, particularly at the 0.01 confidence level, e.g., by one way variance analysis (e.g., as described in Statistical Methods by Snedecor and Cochran).

Increase of the vegetative growth of a transgenic plant is preferably monitored by measuring the increase in dry weight during the growth period. The mean increase of dry weight is defined as the difference in mean dry weight of transgenic plants and wild type plants multiplied by 100 and divided by the mean dry weight of wild type plants. Typical increases in dry weight, particularly early in growth period, by introduction of the chimeric cycD2 genes of the invention range from at least about 39% to about 350%, particularly from about 68% to about 150%.

It is clear that increases in dry weight resulting from introduction of the chimeric genes of the invention may vary, depending on the plant species or chimeric genes used, and any significant increase in dry weight in transgenic plants is encompassed by the invention, particularly a dry weight of at least about 1.4 times to at least about 4.5 times the dry weight in untransformed control plants, particularly of at least about 1.8 times to at least about 2.7 times the dry weight in untransformed control plants. In any case, the mean dry weight of the transgenic plants is statistically significantly different from the mean dry weight of the untransformed plants.

Increase in the vegetative growth of a transgenic plant can also be determined by comparing the number of leaves visible on the transgenic plants and the control wild-type plants at any given, point in time. The difference in number of leaves of transgenic plants in the middle of the growth period is expected to be at least about 1.1 to at least about 3 times, particularly at least about 1.5 to at least about 2 times the leaf number in untransformed plants.

Increase of the vegetative growth of a transgenic plant can also be monitored by measuring the height of the stem (measured from soil level to the top of growing point) during the growth period. The mean increase of the stem height is defined as the difference in mean stem height of transgenic plants and wild type plants multiplied by 100 and divided by the mean height of wild type plants. Typical increases in stem height by introduction of the chimeric cycD2 genes of the invention range from at least about 65% early during growth, over at least about 20–30% in the middle of the growing period, to at least about 10% by the time of flowering, but may be as high as about 120% to about 190% early during growth, as high as about 40–50% to about 75% in the middle of the growing period, and as high as about 15–20% at the end of the flowering stage.

It is clear that increases in stem height resulting from introduction of the chimeric genes of the invention may vary, depending on the plant species or chimeric genes used, and any significant increase in stem height in transgenic plants is encompassed by the invention, particularly stem height of at least about 1.1 times to at least about 3 times the stem height in untransformed control plants, particularly of at least about 1.5 times to at least about 2 times the stem height in untransformed control plants.

The difference in stem height between transgenic and control plants diminishes as growth progresses, because the growth rate slows down in plants that are flowering. The terminal height of a transgenic plant, may thus be similar to the terminal height of a non-transgenic plant.

The transgenic plants comprising the chimeric cycD2 genes of the invention have an increased growth rate, when compared with untransformed plants, resulting in a reduced time required to reach a given dry weight or stem height. "Growth rate" as used herein, refers to the increase in size of a plant or part of plant per day, particularly to increase in stem height per day, and can be calculated as the difference between the size of a plant or part of a plant at the start and end of a period comprising a number of days, particularly 6 to 8 days, divided by the number of days. Increase in growth rate is preferably expressed according to the general definition of increase of a measurable phenotype, but can also be expressed as the ratio between the growth rate of the transgenic plants, versus the growth rate of the untransformed control plants, during the same period, under the same conditions.

As mentioned before the increase in growth rate resulting from introduction of the chimeric genes, particularly the chimeric cycD2 genes of the invention may vary, depending on the plant species or the chimeric genes used, and any significant increase in growth rate in transgenic plants is encompassed by the invention, particularly increase in growth rate ranging from about 4% to about 85%, more particularly from about 20% to about 60%, especially from about 30% to about 50%.

Increase of the vegetative growth of a transgenic plant can also be monitored by measuring the length or the size of the largest leaf at different time points during the growth period whilst the leaves are still expanding. This measurable phenotype is a measure of the increased maturity of the transgenic plants. The mean increase of the length of the largest leaf (defined as the difference between mean length of the largest leaf of transgenic plants and wild type plants multiplied by 100 and divided by the mean length of the largest leaf of wild type plants) obtained by introduction of the chimeric genes of the invention ranges from about 7 to 31% (mean about 17%) early during growth, to about 3–14% (mean about 7%) in the middle of the growing period.

Again, these increases in the size of the largest leaf, resulting from introduction of the chimeric genes of the invention, may vary, depending on the plant species or chimeric gene used, and any significant increase in leaf growth or size in transgenic plants is encompassed by the invention.

As another object of the invention, the chimeric cell-division controlling gene, particularly the chimeric cycD2 genes, can also be introduced in plants to increase the root development, particularly to increase the mean root length. In general, the increase in root development, is parallel to the increase in the vegetative part above the ground (stem, leaves, flowers) and may range from about 40% to about 70%, but again these increases may vary depending on the plant species or chimeric gene used, and any significant increase, particularly statistically significant increase in root development is encompassed by the invention.

As yet another object of the invention, the chimeric cell-division controlling gene, particularly the chimeric cycD2 genes, can also be introduced in plants to increase the size as well as the number of flowers, particularly the number of fertilized flowers, and the number of fertilized ovules in each flower. As a result of the increase in the number of fertilized flowers, and the number of fertilized ovules in each flower (generally leading to a greater number of seeds per plant), it is clear that; also an increase in seed yield per plant can be obtained. It is clear that the increase in the number of flowers and ovules per flower, as well as the increase in seed yield can vary, depending on the plant species transformed with the chimeric cell-division controlling genes of the invention or the chimeric genes used. Typical increases in flower size resulting from the introduction of a chimeric gene comprising a CycD2 encoding DNA region under control of a CaMV35S promoter range from at least about 4% to at least about 30%, particularly at least about 10% to at least about 20%. Typical increases in the number of flowers range from about at least 20% to at least about 50%, particularly from about 24% to about 45% while increases in the number of seeds/plants (expressed on a weight basis) are in a range from at least about 5% to at least about 55%, particularly from at least about 10% to at least about 30%, more particularly about 25%.

In still another embodiment of the invention, the chimeric cell-division controlling gene, particularly the chimeric cycD2 genes, can also be introduced in plants or their seeds to accelerate germination. It has been found that transgenic seeds comprising the chimeric cycD2 genes of the invention can germinate at least between about 8 to about 16 hrs faster than wild type controls.

Moreover, the mentioned chimeric genes can also be introduced in plants to decrease the mean number of days required to reach the development of an inflorescence, thus effectively reducing the time required to start flowering. Transgenic plants comprising the chimeric cycD2 genes of the invention thus reach maturity, particularly the flowering stage, earlier, but have the normal size of a flowering plant. The actual reduction in time required to reach the flowering stage may depend on the plant species or chimeric genes used. Typically, transgenic plants harboring the chimeric gene comprising a CycD2 encoding DNA region under control of a CaMV35S promoter exhibit a reduction in the time required to flower of at least about 3% to 11–12%, particularly at least about 4% to 7%.

In another particularly preferred embodiment, a chimeric gene comprising a CycD3 encoding transcribed DNA region under control of a plant-expressible promoter, preferably a constitutive promoter, particularly a CaMV35S promoter, such as a chimeric gene comprising the nucleotide sequence of the chimeric cycD3 gene of pCRK9, is introduced into a plant cell to obtain transgenic plants with altered morphological traits or architecture, particularly with altered size of specific plant parts or organs, more particularly with altered flower size and morphology such as flowers with elongated and/or enlarged petals. Transgenic plants transformed with a chimeric gene comprising a CycD3 encoding DNA region under control of a plant-expressible promoter (and the progeny thereof) exhibit an increase in the flower size of about 31% to about 44%. Moreover these transgenic plants also flower later than wild type plants, corresponding to an increase in flowering time of about 5% to about 20%, particularly about 8% to about 16%.

In another embodiment of the invention the functional level of the cell-division controlling protein, capable of phosphorylating an RB-like protein or binding the pocket domain of an Rb-like proteins, particularly of the D-type cyclin is increased, to obtain a plant with altered growth rate or architecture, by integrating a chimeric gene into the genome of the cells of the plant, comprising the following operably linked DNA fragments:

a) a plant-expressible promoter region, particularly a CaMV35S promoter region, b) a transcribed DNA region encoding a protein, which when expressed, increases the functional level of a cell-division controlling protein, preferably encoding a mutant cell-division controlling protein or part of a mutant cell-division controlling protein, more preferably encoding a mutant D-type cyclin or part of a D-type cyclin, particularly encoding a D-type cyclin which has a mutation in cyclin box (quite particularly a substitution of amino acid 185 or amino acid 155 of a D2-type cyclin, especially E185A or K155A), or a D-type cyclin wherein the PEST sequences are removed, particularly which has been C-terminally deleted to remove the PEST sequences, or a D-type cyclin wherein the LxCxE binding motif has been changed or deleted, particularly wherein the C-residue from the LxCxE binding motif has been deleted; and optionally c) a 3' end formation and polyadenylation signal functional in plant cells.

Although not intending to limit the invention to a mode of action, it is believed that the mutant cell-division controlling proteins exert their effects by sequestering inhibitors or antagonists of the normal functional cell-division controlling proteins.

It is clear from this description that chimeric genes comprising a transcribed DNA region encoding other cyclins of the D-type, particularly plant-derived cyclins of the CycD group, may be used to obtain similar effects. These genes can be obtained from other plant species or varieties, by different methods including hybridization using the available CycD1, CycD2 or CycD3 encoding DNAs as probes and hybridization conditions with reduced stringency, or polymerase chain reaction based methods using oligonucleotides based on the available nucleotide sequences of D-type cyclins, preferably oligonucleotides having a nucleotide sequence corresponding to the sequences encoding the consensus amino acid sequences, particularly oligonucleotides having a nucleotide sequence corresponding to the sequences encoding conserved amino acid sequences within the cyclin box for each group of cyclins. These conserved amino acid sequences can be deduced from available aligned DNA encoding such amino acid sequences. A particularly preferred combination of oligonucleotides for PCR amplification of plant cyclins of the D1 type is an oligonucleotide selected from the group of oligonucleotides having the DNA sequence of SEQ ID NO:12 SEQ ID NO:13 or SEQ ID NO:14 and an oligonucleotide selected from the group of oligonucleotides having the DNA sequence of SEQ ID NO:15 or SEQ ID NO:16.

A particularly preferred combination of oligonucleotides for PCR amplification of plant cyclins of the D2 type is an oligonucleotide selected from the group of oligonucleotides having the DNA sequence of SEQ ID NO:17 or SEQ ID NO:18 and an oligonucleotide selected from the group of oligonucleotides having the DNA sequence of SEQ ID NO:19 or SEQ ID NO:20. A particularly preferred combination of oligonucleotides for PCR amplification of plant cyclins of the D3 type is an oligonucleotide selected from the group of oligonucleotides having the DNA sequence of SEQ ID NO:21, SEQ ID NO:22 or SEQ ID NO:23 and an oligonucleotide selected from the group of oligonucleotides having the DNA sequence of SEQ ID NO:24 or SEQ ID NO:25. The amplified DNA fragment is then used to screen a cDNA or genomic library (under stringent conditions) to isolate full length clones.

Alternatively, additional genes encoding plant-derived cyclins can be obtained by techniques such as, but not limited to, functional complementation of conditional G1-S cyclin deficient yeast strains, as described by Soni et al. (1995) and Dahl et al. (1995) or by using the yeast two-hybrid system (Fields and Song, 1989) to isolate DNA sequences encoding cyclins binding to the pocket domain of Rb-like proteins as described supra.

It is further known that some plants contain more than one gene encoding a D-type cyclin of the same subgroup (e.g., tobacco contains at least two genes of the CycD3 subgroup) and it is clear that these variants can be used within the scope of the invention.

Moreover D-type cyclins which have an amino acid sequence which is essentially similar to the ones disclosed in this invention, such as mutant D-type cyclins, can be used to the same effect. With regard to "amino acid sequences", essentially similar means that when the two relevant sequences are aligned, the percent sequence identity i.e., the number of positions with identical amino acid residues divided by the number of residues in the shorter of the two sequences- is higher than 80%, preferably higher than 90%. The alignment of the two amino acid sequences is performed by the Wilbur and Lipmann algorithm (Wilbur and Lipmann, 1983) using a window-size of 20 amino acids, a word length of 2 amino acids, and a gap penalty of 4. Computer-assisted analysis and interpretation of sequence data including sequence alignment as described above, can be conveniently performed using the programs of the Intelligenetics™ Suite (Intelligenetics Inc. CA).

It is clear that any DNA sequence encoding a cell-division controlling protein, particularly a D-type cyclin, can be used to construct the chimeric cell-division controlling genes of the invention, especially DNA sequences which are partly or completely synthesized by man.

It is also clear that other plant-expressible promoters, particularly constitutive promoters, such as the the opine synthase promoters of the Agrobacterium Ti- or Ri-plasmids, particularly a nopaline synthase promoter can be used to obtain similar effects. Moreover, in the light of the existence of variant forms of the CaMV35S promoter, as known by the skilled artisan, the object of the invention can be equally be achieved by employing these alternative CaMV35S promoters, such as those described by Hull and Howell, Virology, 86, pg. 482 (1978).

It is a further object of the invention to provide plants with altered morphology or architecture, restricted to specific organs or tissues by using tissue-specific or organ-specific promoters to control the expression of the DNA encoding a cell-division controlling protein, particularly a cyclin of the D-type. Such tissue-specific or organ-specific promoters are well known in the art and include but are not limited to seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), meristem specific promoters (such as the promoter of the SHOOTMERISTEMLESS (STM) gene, Long et al., 1996), primordia specific promoter (such as the promoter of the Antirrhinum CycD3a gene, Doonan et al., 1998) and the like.

In another embodiment of the invention, the expression of a chimeric gene encoding a cell-division controlling protein can be controlled at will by the application of an appropriate chemical inducer, by operably linking the DNA region coding for the cell-division controlling protein to a promoter whose expression is induced by a chemical compound, such as the promoter of the gene disclosed in European Patent publication "EP" 0332104, or the promoter of the gene disclosed in WO90/08826.

In yet another embodiment of the invention, the expression of a chimeric gene encoding a cell-division controlling protein can be controlled by use of site-specific recombinases and their corresponding cis-acting sequences, e.g., by inserting between the plant-expressible promoter and the transcribed region encoding the cell-division controlling protein, an unrelated nucleotide sequence (preferably with transcriptional and/or translational termination signals) flanked by the cis-acting sequences recognized by a site-specific recombinase (e.g., lox or FRT sites); providing the plant cells comprising this chimeric gene with the site-specific recombinase (e.g., Cre or FLP) so that the inserted unrelated nucleotide sequence is eliminated by recombination, thus allowing the chimeric cell division controlling gene to be expressed.

It is thought that the morphological alterations obtained by increased expression of cell-division controlling proteins, particularly D-type cyclins in plants due to the introduction of a chimeric gene comprising a DNA region encoding a cell-division controlling protein, particularly a D-type cyclin under control of a plant expressible promoter, can be enhanced, by removal, adaptation or inactivation of PEST sequences. PEST sequences are amino acid sequences which are rich in proline, glutamate or aspartate and serine or threonine, located between positively charged flanking residues, which are involved in rapid turnover of the protein comprising such sequences (Tyers et al., 1992; Cross, 1988; Wittenberg and Reed, 1988; Salama et al., 1994). Removal of these PEST sequences in yeast cyclins stabilizes the cyclins in vivo (Pines, 1995). PEST regions can be identified by computer analysis, using software packages such as PESTFIND (Rogers et al., 1986; Rechsteiner, 1990). Mutation of a DNA encoding cell-division controlling protein with altered PEST sequences is well within the reach of the skilled artisan using methods such as described e.g., by Sambrook et al. (1989)

It is further expected that the quantitative effects of phenotypic alterations can be modulated -i.e., enhanced or repressed- by expression of endogenous cell-division controlling encoding chimeric genes, particularly endogenous CycD encoding chimeric genes as an alternative to using heterologous genes encoding similar proteins from other plants. Preferably, heterologous genes are used, particularly heterologous genes encoding similar proteins with less than about 65%, preferably less than about 75%, more preferably less than about 65% amino acid sequence identity to the endogenous cell division controlling protein.

In another aspect of this invention, the morphology of plants can be altered by decreasing expression of a functional cell-division controlling protein, particularly a D-type cyclin. This can be achieved using e.g., antisense-RNA, ribozyme, or co-suppresion techniques. To this end, a chimeric gene comprising a transcribed DNA region which is transcribed into an RNA, the production of which reduces, inhibits or prevents the expression of a cell-division controlling protein, particularly a D-type cyclin within the plant cells is introduced in the plant cells, particularly stably integrated in the genome of the plant cells.

In one embodiment of this aspect, the transcribed DNA region of the chimeric gene encodes an antisense RNA which is complementary to at least part of a sense mRNA encoding a cell-division controlling protein, particularly a D-type cyclin. The antisense RNA thus comprises a region which is complementary to a part of the sense mRNA preferably to a continuous stretch thereof of at least 50 bases in length, particularly of at least between 100 and 1000 bases in length. The antisense RNA can be complementary to any part of the mRNA sequence: it may be complementary to the sequence proximal to the 5' end or capping site, to part or all of the leader region, to an intron or exon region (or to a region bridging an exon and intron) of the sense pre-mRNA, to the region bridging the noncoding and coding region, to all or part of the coding region including the 3' end of the coding region, and/or to all or part of the 3' or trailer region. The sequence similarity between the antisense RNA and the complement of the sense RNA encoding a cell-division controlling protein, should be in the range of at least about 75% to about 100%.

In another embodiment of this aspect, the transcribed DNA region of the chimeric gene encodes a specific RNA enzyme or so-called ribozyme (see e.g., WO 89/05852) capable of highly specific cleavage of the sense mRNA encoding a cell-division controlling protein, particularly a D-type cyclin.

In yet another embodiment, the level of a functional cell-division controlling protein, particularly a D-type cyclin can be decreased by the expression of chimeric gene comprising a DNA region encoding a protein or polypeptide which when expressed reduces the level of a cell-division controlling protein, particularly a D-type cyclin, or inhibits the cell division controlling protein, particularly the D-type cyclin, to exert its function within the plant cells. Preferably, the chimeric gene encodes an antibody that binds to a cell-division controlling protein, particularly a D-type cyclin.

Decreasing the level or the functional level of a cell-division controlling protein, particularly a D-type cyclin within the cells of a transgenic plant, comprising the chimeric genes of this embodiment of the invention, results in altered architecture, particularly in a decreased stem height, a decrease of the growth rate or a delaying in the flowering of the transgenic plants when compared to untransformed plants, grown under the same conditions. The effect obtained might vary, depending on the plant species or chimeric genes used, and any effect on architecture and/or growth rate, particularly a decrease in stem height or growth rate, or an increase in the time required to develop an inflorescence, is encompassed by the invention.

The decrease in growth rate due to decreasing the level of a cell-division controlling protein, preferably a D-type cyclin, particularly a CYCD2 type cyclin, ranges from about 30% to about 60%, particularly from about 35% to about 50%.

The decrease in stem height due to decreasing the level of a cell-division controlling protein, preferably a D-type cyclin, particularly a CYCD2 type cyclin, ranges from about 10% to about 60%, particularly from about 30% to about 50%, more particularly around 40%.

The increase in flowering time due to decreasing the level of a cell-division controlling protein, preferably a D-type cyclin, particularly a D2 type cyclin, ranges from about 10% to about 40%, particularly from about 15% to about 38%.

The chimeric cell-division controlling gene may include further regulatory or other sequences, such as leader sequences [e.g., cab22L leader from Petunia or the omega leader from TMV (Gallie et al., 1987)], 3' transcription termination and polyadenylation signals (e.g., of the octopine synthase gene [De Greve et al., 1982)], of the nopaline synthase gene [Depicker et al., 1982] or of the T-DNA gene 7 [Velten and Schell, 1985] and the like [Guerineau et al., 1991; Proudfoot, 1991; Safacon et al., 1991; Mogen et al., 1990; Munroe et al., 1990; Ballas et al., 1989; Joshi et al.,1987], plant translation initiation consensus sequences [Joshi, 1987], introns [Luehrsen and Walbot, 1991] and the like, operably linked to the nucleotide sequence of the chimeric cell-division controlling gene.

Preferably, the recombinant DNA comprising the chimeric cell-division controlling gene is accompanied by a chimeric marker gene. The chimerc marker gene can comprise a marker DNA that is operably linked at its 5' end to a plant-expressible promoter, preferably a constitutive promoter, such as the CaMV 35S promoter, or a light inducible promoter such as the promoter of the gene encoding the small subunit of Rubisco; and operably linked at its 3' end to suitable plant transcription 3' end formation and polyadenylation signals. It is expected that the choice of the marker DNA is not critical, and any suitable marker DNA can be used. For example, a marker DNA can encode a protein that provides a distinguishable color to the transformed plant cell, such as the A1 gene (Meyer et al., 1987), can provide herbicide resistance to the transformed plant cell, such as the bar gene, encoding resistance to phosphinothricin (EP 0,242,246), or can provided antibiotic resistance to the transformed cells, such as the aac(6') gene, encoding resistance to gentamycin (WO94/01560).

Although it is clear that the invention can be applied essentially to all plant species and varieties, the invention will be especially suited to alter the architecture or to increase the growth rate of plants with a commercial value. It is expected that the enhancements in vegetative growth will be most pronounced in plants which have not undergone extensive breeding and selection for fast vegetative growth. The invention will be particularly relevant for plant which are grown in greenhouse, particularly to reduce the time required for greenhouse plants to reach the desired developmental stage, such as but not limited to flowering, fruit setting or seed setting. The invention will further be relevant to enhance the growth rate of trees, particularly softwood trees such as pine, poplar, Eucalyptus trees and the like. Another important application of the invention encompasses the expansion of effective area wherein plants can be cultivated by reduction of the time required to reach the economically important developmental stage. Particularly preferred plants to which the invention can be applied are corn, oil seed rape, linseed, wheat, grasses, alfalfa, legumes, a brassica vegetable, tomato, lettuce, rice, barley, potato, tobacco, sugar beet, sunflower, and ornamental plants such as carnation, chrysanthemum, roses, tulips and the like.

A recombinant DNA comprising a chimeric cell-division controlling gene can be stably incorporated in the nuclear genome of a cell of a plant. Gene transfer can be carried out with a vector that is a disarmed Ti-plasmid, comprising a chimeric gene of the invention, and carried by Agrobacterium. This transformation can be carried out using the procedures described, for example, in EP 0,116,718. Alternatively, any type of vector can be used to transform the plant cell, applying methods such as direct gene transfer (as described, for example, in EP 0,233,247), pollen-mediated transformation (as described, for example, in EP 0,270,356, WO85/01856 and U.S. Pat. No. 4,684,611), plant RNA virus-mediated transformation (as described, for example, in EP 0,067,553 and U.S. Pat. No. 4,407,956), liposome-mediated transformation (as described, for example, in U.S. Pat. No. 4,536,475), and the like.

Other methods, such as microprojectile bombardment as described, for corn by Fromm et al. (1990) and Gordon-Kamm et al. (1990), are suitable as well. Cells of monocotyledonous plants, such as the major cereals, can also be transformed using wounded and/or enzyme-degraded compact embryogenic tissue capable of forming compact embryogenic callus, or wounded and/or degraded immmature embryos as described in WO92/09696. The resulting transformed plant cell can then be used to regenerate a transformed plant in a conventional manner.

The obtained transformed plant can be used in a conventional breeding scheme to produce more transformed plants with the same characteristics or to introduce the chimeric cell-division controlling gene of the invention in other varieties of the same or related plant species. Seeds obtained from the transformed plants contain the chimeric cell-division controlling gene of the invention as a stable genomic insert.

The following non-limiting Examples describe the construction of chimeric cell-division controlling genes and the use of such genes for the modification of the architecture and growth rate of plants. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) Current Protocols in *Molecular Biology, Current Protocols, USA*. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

Throughout the description and Examples, reference is made to the following sequences:

SEQ ID NO:1 cDNA encoding *Nicotiana tabacum* CYCD2;1

SEQ ID NO:3 cDNA encoding *Nicotiana tabacum* CYCD3;1

SEQ ID NO:5 cDNA encoding *Nicotiana tabacum* CYCD3;2

SEQ ID NO:7 cDNA encoding *Helianthus tuberosus* CYCD1;1

SEQ ID NO:9 cDNA encoding *Helianthus tuberosus* CYCD3;1

SEQ ID NO:11 T-DNA of pGSV5

SEQ ID NO:12 PCR primer 1

SEQ ID NO:13 PCR primer 2

SEQ ID NO:14 PCR primer 3

SEQ ID NO:15 PCR primer 4

SEQ ID NO:16 PCR primer 5

SEQ ID NO:17 PCR primer 6

SEQ ID NO:18 PCR primer 7

SEQ ID NO:19 PCR primer 8

SEQ ID NO:20 PCR primer 9

SEQ ID NO:21 PCR primer 10

SEQ ID NO:22 PCR primer 11

SEQ ID NO:23 PCR primer 12

SEQ ID NO:24 PCR primer 13

SEQ ID NO:25 PCR primer 14

SEQ ID NO:26 cDNA encoding *Zea mays* CYCD2

Plasmids pCEC1 and pCRK9 have been deposited at the

Belgian Coordinated Collections of Microorganisms (BCCM)

Laboratorium voor Moleculaire Biologie-Plasmidecollectie (LMBP)

Universiteit Gent

K. L. Ledeganckstraat 35

B-9000 Gent, Belgium on Mar. 11, 1997 and have been attributed the following deposition numbers:

MC1061(pCEC1): BCCM/LMBP3657

DH5α (pCRK9): BCCM/LMBP3656

Plasmids pBlueScript-ZM18 has been deposited at the

Belgian Coordinated Collections of Microorganisms (BCCM)

Laboratorium voor Moleculaire Biologie-Plasmidecollectie (LMBP)

Universiteit Gent

K. L. Ledeganckstraat 35

B-9000 Gent, Belgium on Mar. 19, 1998 under the deposit number BCCM/LMBP 3866.

EXAMPLES

Example 1

Construction of the Chimeric Genes 1.1 Construction of the CaMV35S-AthcycD2 Chimeric Gene X Inclusion in a T-DNA Vector.

A 1298 bp NcoI-SacI fragment comprising the DNA encoding CYCD2 from *A. thaliana* (having the nucleotide sequence of EMBL Accesion No X83370 from nucleotide position 194 to nuceotide position 1332) was treated with Klenow polymerase to render the protruding termini blunt, and ligated to SmaI linearized pART7 (Gleave, 1992), yielding plasmid pCEC1. In this way, a chimeric gene flanked by NotI sites was constructed, wherein the DNA encoding the CYCD2 was operably linked to a CaMV35S promoter of the CabbB-J1 isolate (Harpster et al., 1988) and a 3'ocs region (MacDonald et al., 1991). The chimeric gene was then inserted between the T-DNA border of a T-DNA vector, comprising also a selectable chimeric marker gene.

To this end, the chimeric cycD2 gene was excised from pCEC1, using NotI, and ligated to NotI linearized pART27 (Gleave, 1992) to create pCEC5. pART27 comprises a chimeric selectable marker gene consisting of the following operably linked fragments: a nopaline synthase gene promoter, a neo coding region and 3' end of a nopaline synthase gene (An et al., 1988).

Alternatively, the chimeric cycD2 gene is excised from pCEC1 using an appropriate restriction enzyme (e.g. NotI) and introduced in the polylinker between the T-DNA border sequences of the T-DNA vector pGSV5, together with a selectable chimeric marker gene (pSSU-bar-3'ocs; De Aimedia el al., 1989) viewing pCEC5b. pGSV5 was derived from plasmid pGSC1700 (Cornelissen and Vandewiele, 1989) but differs from the latter in that it does not contain a beta-lactamase gene and that its T-DNA is characterized by the sequence of SEQ ID NO:11.

1.2 Construction of the CaMV35S-AthcycD3 Chimeric Gene and Inclusion in a T-DNA Vector.

The cycD3 cDNA was isolated as a 1335 bp BsI-DraI fragment, rendered blunt-ended by treatment with Kienow polymerase (having the nucleotide sequence of EMBL Accesion No X83371 from nucleotide position 104 to nucleotide position 1439) and inserted into the SmaI site of pUC18, to create pRS14a. This clone carries the full coding sequence of cycD3, with the translation initiation codon located immediately adjacent to the cleaved SmaI site of pUC18 in such an orientation that the SacI site of pUC18 is at the 5' end of the cycD3 cDNA and the BamHI site is at the 3' end. The 1.35 kb SacI-BamHI fragment of pRS14a was isolated and ligated to the about 26.6 kb SacI-BamHI fragment of pSLJ94 (Jones et al., 1992), generating pCRK9. In this way a chimeric gene was constructed wherein the DNA encoding the cycD3 coding region from *A. thaliana* was operably linked to a CaMV35S promoter and the 3'ocs region. In pCRK9 the chimeric gene is located between T-DNA borders, accompanied by a chimeric selectable neo gene (Jones et al., 1992)

Alternatively, the chimeric cycD3 gene is excised from pRS14a using appropriate restriction enzymes and introduced in the polylinker between the T-DNA border sequences of the T-DNA vector pGSV5, together with a selectable chimeric marker gene (pSSU-bar-3'ocs; De Almeida et al., 1989) yielding pCRK9b.

Example 2

Agrobacterium-mediated Transformation of Tobacco Plants with the T-DNA Vectors of Example 1

T-DNA vectors pCEC5 and pCRK9 were introduced in *Agrobacterium tumefaciens* LBA4404 (Klapwijk et al., 1980) by electroporation as described by Walkerpeach and Velten (1995) and transformants were selected using spectinomycin and tetracycline respectively.

T-DNA vectors pCEC5b and pCRK9b are introduced in *A. tumefaciens* C58C1Rif$^R$ by triparental mating (Ditta et al., 1980).

The resulting Agrobacterium strains were used to transform *Nicotiana tabacum* var Xanthi, applying the leaf disc transformation method as described in An et al. (1985).

Eight tobacco plants transformed with pCRK9 (designated 1K9, 2K9, 3K9, 4K9, 8K9, 10K9, 17K9, 19K9 and 28K9) were generated and eleven tobacco plants transformed with pCEC5 (designated C8 lines 1 to 3 and 5 to 12).

Plants transformed by pCRK9 T-DNA were analyzed for the copy number of the inserted transgenes by Southern hybridization using the labelled cDNA insert of pRS14a as probe. Lines 2K9, 3K9 and 4K9 each had obtained 1 copy of the transgene, while line 1K9 contained three copies of the transgene.

Plants transformed by pCEC5 T-DNA were analyzed for the copy number of the inserted transgenes by Southern hybridization using BamHI digested DNA prepared from these plants and labelled 0.7 kb NcoI-EcoRI fragment from J22 cDNA (comprising part of the cycD2 coding region; Soni et al., 1995). Lines C8-2, C8-3, C8-5, C8-8, C8-9, C8-10, C8-11, C8-12 all had one copy of the transgene, line C8-7 had two copies, line C8-6 had three copies and line C8-1 had four copies of the transgene.

The T0 (primary transformants) were self-fertilized and allowed to set seeds (T1 seeds). Plants grown from T1 seeds were designated C8-T1-X, where X stands for the line number of the original transformant. Seeds from T1 plants were referred to as T2 seed; plants grown from such seed were named C8-T2-X, where X is again the line number of the original transformant. Whenever the generation was not mentioned, the plants were grown from T1 seed.

Northern analysis confirmed transcription of the transgenes in at least lines C8-1, C8-3, C8-7, 3K9, 4K9 and 8K9.

Example 3

Phenotypic Analysis of the Transformed Tobacco Plants

3. Tobacco Plants Comprising the CaMV35S-AthCycD2 Chimeric Gene.

Seeds from primary transformants (T0 plants) were surface sterilized in 10% bleach for 15 minutes and thoroughly washed in sterile water. The surface-sterilized seeds were germinated on GM medium containing kanamycin to a final concentration of 100 $\mu$g/ml. Seeds on plates were placed for 5 days at 4° C. (vernalization) and then moved to 23° C. in a growth chamber. All time points refer to the day of placing in the growth chamber. Eighteen days after moving to the growth chamber (ie after 23 days in total), the kanamycin-resistant seedlings were transplanted into seed trays containing soil, and grown under 18 hr photoperiod in a growth room. After a further 10 days these plants were transferred to 3 inch plant pots and after an additional 15 days to 8 inch plant pots where they remained for the rest of the experiment. The 3 inch and 8 inch plant pots were incubated in a greenhouse supplemented with additional lighting to achieve an 18 hour photoperiod. Plants were placed in randomised design within the greenhouse.

Measurements were started two days later (i.e., after 45 days or after 27 days in soil; referred to as week 1), and repeated every week for seven weeks, when appropriate. The following number of plants were analyzed for each line: 22 plants for line C8-1, 7 plants for line C8-2, 22 plants for line C8-3, 8 plants for line C8-5, 6 plants for line C8-6, 22 plants for line C8-7, 5 plants for line C8-8, 6 plants for line C8-9, 4 plants for line C8-10, 6 plants for line C8-11, 5 plants for line C8-12, 34 plants for untransformed control (wild type).

The following parameters were analyzed: height of the plants from the soil surface to the highest point (i.e., growing tip; summarized in Table 1 as mean height ± standard deviation in cm); length of the largest leaf at defined times (summarized in Table 2 as mean length ± standard deviation in cm); time (summarized in Table 3 as mean time ± standard deviation in days) at which an inflorescence meristem is visible with the naked eye (inflorescences of 0.25 cm and 1 cm); height at which an inflorescence meristem is visible (summarized in Table 3 as mean length ± standard deviation in cm); length of the petal tube of the flowers; width of the collar of the petal tube (summarized in Table 3 as mean length and width ± standard deviation in mm); total number of seed pods per plant; and average seed yield (on a weight basis) per plant.

The transgenic plants exhibited an increased growth rate, apparent from the seedling stage, resulting in a larger average stem height (Table 1). At time point week 3, all populations of transgenic lines are significantly larger than the untransformed controls (t-test; at confidence level 95%), while lines C8-1, C8-2, C8-3, C8-5, C8-11 significantly larger than the untransformed controls at a confidence level of 99%. The increased growth rate also resulted on average in larger leaves at the indicated times, which correspond to a period when leaf expansion is continuing (Table 2) and larger flowers, wherein the petal tube of transgenic plants is on average longer than the petal tube from flowers on untransformed plants.

Also the number of flowers was increased in transgenic plants, as well as the number of fertilized flowers, resulting in a larger number of seed pods, and a greater seed yield per plant (data summarized in Table 4A). Moreover, the number of seeds per pod was larger in the transgenic plants than in the wild-type control plants. The aberrant seed yield in line C8-T1-6, was due to excessive high percentage of flower abscission.

It can thus be concluded that constitutive expression of AthCycD2 encoding DNA, leads to an increase both in number of seed pods and total yield of seeds on a per plant basis.

Finally, the root development in wild-type seedlings and transgenic seedlings was compared (Table 4B). Seeds were sterilized, sown on GM media plates without selection, vernalized and then stored in the vertical position in the growth room. Root length was measured 9 days and 13 days after vernalization and the presence of lateral roots recorded. Seeds from line C8-T1-7 and C8-T2-2 (homozygous) were used. Line C8-T1-7 possesses two inserts which segregate approximately 15:1 on kanamycin plates. 35 seedlings were grown from this line and of these, three appeared to represent the rate of growth observed in wild type seedlings. Data from these seedlings was recorded separately nine days after vernalization. The t-test was applied to determine the significance of the mean difference and the level of significance is indicated in the table. ns denotes no significant difference between the samples. It thus seems that the increase in vegative growth in the apical parts is balanced by an equal increase in the root development.

TABLE 1

Mean height (in cm) of transformed tobacco plants comprising CaMV35S-AtcycD2

| Line | Week 1 (45 days) | Week 2 (51 days) | Week 3 (59 days) | Week 4 (65 days) | Week 5 (73 days) | Week 6 (81 days) | Week 7 (89 days) |
|---|---|---|---|---|---|---|---|
| C8-T1-1 | 5.86 ± 2.45 | 13.71 ± 3.43 | 38.91 ± 6.61 | 63.09 ± 9.69 | 99.42 ± 10.25 | 123.30 ± 24.60 | 137.09 ± 31.90 |
| C8-T1-2 | 8.50 ± 1.23 | 18.29 ± 2.21 | 49.86 ± 4.73 | 77.64 ± 4.73 | 117.14 ± 10.71 | 147.71 ± 17.75 | 168.00 ± 9.93 |
| C8-T1-3 | 8.61 ± 2.59 | 17.41 ± 4.94 | 43.14 ± 9.08 | 66.61 ± 11.04 | 100.41 ± 15.57 | 134.95 ± 21.17 | 145.73 ± 22.15 |
| C8-T1-5 | 6.81 ± 1.16 | 16.31 ± 1.89 | 44.38 ± 3.66 | 70.69 ± 5.30 | 106.50 ± 6.12 | 143.63 ± 12.33 | 159.88 ± 9.88 |
| C8-T1-6 | 4.83 ± 1.75 | 10.75 ± 2.51 | 33.10 ± 6.47 | 52.67 ± 5.83 | 84.83 ± 8.08 | 120.50 ± 13.73 | 141.80 ± 5.63 |
| C8-T1-7 | 8.64 ± 3.04 | 18.82 ± 4.56 | 48.32 ± 6.12 | 74.66 ± 7.12 | 111.50 ± 8.38 | 149.59 ± 11.05 | 169.14 ± 11.99 |
| C8-T1-8 | 5.50 ± 1.41 | 13.2 ± 2.41 | 41.2 ± 2.17 | 62.40 ± 3.98 | 97.40 ± 8.08 | 134.20 ± 5.63 | 156.80 ± 11.86 |
| C8-T1-9 | 3.75 ± 1.44 | 10.58 ± 3.32 | 35.67 ± 6.80 | 62.17 ± 9.72 | 100.67 ± 12.24 | 137.83 ± 20.34 | 162.17 ± 18.67 |
| C8-T1-10 | 9.88 ± 1.89 | 21.00 ± 4.08 | 47.75 ± 8.02 | 75.38 ± 7.11 | 113.75 ± 9.21 | 152.75 ± 11.99 | 164.50 ± 177.21 |
| C8-T1-11 | 10.00 ± 2.30 | 19.51 ± 3.82 | 45.17 ± 5.63 | 72.25 ± 5.50 | 103.33 ± 11.52 | 144.58 ± 5.63 | 152.83 ± 18.28 |
| C8-T1-12 | 9.20 ± 2.66 | 17.9 ± 5.15 | 42.8 ± 11.01 | 68.6 ± 13.32 | 103.40 ± 14.40 | 140.80 ± 12.16 | 161.8 ± 10.76 |
| wild-type | 4.48 ± 1.63 | 10.50 ± 3.33 | 31.82 ± 6.62 | 54.00 ± 7.89 | 86.56 ± 10.91 | 121.81 ± 18.28 | 145.18 ± 19.44 |

TABLE 2

Mean leaf length (in cm) of the largest leaf of transformed tobacco plants comprising CaMV35S-AtcycD2

| Line | Week 1 | Week 2 | Week 3 |
|---|---|---|---|
| C8-T1-1 | 13.500 ± 1.846 | 19.909 ± 2.004 | 27.114 ± 2.182 |
| C8-T1-2 | 16.643 ± 1.282 | 23.500 ± 1.354 | 29.643 ± 1.842 |
| C8-T1-3 | 15.955 ± 2.400 | 20.951 ± 3.737 | 27.341 ± 3.095 |
| C8-T1-5 | 15.062 ± 1.635 | 21.563 ± 1.741 | 28.875 ± 2.372 |
| C8-T1-6 | 14.667 ± 1.402 | 20.833 ± 1.807 | 29.927 ± 1.201 |
| C8-T1-7 | 15.886 ± 1.718 | 22.000 ± 1.498 | 28.909 ± 1.974 |
| C8-T1-8 | 14.167 ± 2.229 | 20.500 ± 1.871 | 27.583 ± 1.856 |
| C8-T1-9 | 12.417 ± 2.035 | 18.917 ± 2.010 | 26.333 ± 2.113 |
| C8-T1-10 | 14.750 ± 2.693 | 20.167 ± 2.825 | 27.583 ± 2.635 |
| C8-T1-11 | 15.833 ± 2.113 | 21.333 ± 1.602 | 28.333 ± 1.722 |
| C8-T1-12 | 14.600 ± 1.432 | 21.400 ± 1.475 | 28.100 ± 2.608 |
| wild-type | 12.676 ± 1.846 | 18.691 ± 2.280 | 26.352 ± 1.960 |

TABLE 3A

Floral development [mean height to infloresence of 0.25 cm or 1 cm (in cm), mean time required to reach the development of an infloresence of 0.25 or 1 cm (in days after vernalization)] in tobacco transformed with CaMV35SAthCycD2

| Line | Mean time to inflorescence of 0.25 cm (days) | Mean time to inflorescence of 1 cm (days) | Mean height at inflorescence of 1 cm (cm) |
|---|---|---|---|
| C8-T1-1 | 67.35 ± 4.580 | 74.75 ± 4.541 | 105.5 ± 21.670 |
| C8-T1-2 | 65.42 ± 2.573 | 72.00 ± 3.546 | 110.6 ± 21.439 |
| C8-T1-3 | 68.77 ± 3.436 | 74.32 ± 3.414 | 106.5 ± 14.134 |
| C8-T1-5 | 70.25 ± 2.712 | 76.63 ± 2.387 | 122.4 ± 6.737 |
| C8-T1-6 | 68.00 ± 2.828 | 73.33 ± 2.944 | 117.0 ± 5.550 |
| C8-T1-7 | 70.95 ± 3.034 | 77.15 ± 2.852 | 133.4 ± 14.497 |
| C8-T1-8 | 72.60 ± 3.286 | 77.60 ± 2.793 | 116.1 ± 5.482 |
| C8-T1-9 | 73.17 ± 3.251 | 79.50 ± 2.429 | 129.25 ± 10.324 |
| C8-T1-10 | 72.50 ± 2.517 | 77.75 ± 2.986 | 127.7 ± 19.202 |
| C8-T1-11 | 66.67 ± 1.033 | 73.17 ± 2.137 | 104.6 ± 4.924 |
| C8-T1-12 | 70.00 ± 4.000 | 76.40 ± 3.715 | 121.6 ± 7.893 |
| mean value | 69.61 ± 2.587 | 75.69 ± 2.329 | 117.70 ± 10.082 |
| wild-type | 74.90 ± 3.222 | 79.09 ± 2.342 | 111 ± 10.020 |

TABLE 3B

Floral development [mean flower size i.e., length and width (mm)] in tobacco transformed with CaMV35SAthCycD2. The length and width of five flowers from each plant was measured and the mean flower length or width for each transgenic line was calculated. The values for each independent transgenic line were compared to wild type using the t-test. The table reveals the level of probability that the results are statistically significant compared to wild type. ns means not significant.

| Line | Mean flower length (mm) | Level of significance | Mean flower width (mm) | Level of significance |
|---|---|---|---|---|
| C8-T1-1 | 47.22 ± 2.261 | P < 0.001 | 33.45 ± 1.668 | P < 0.001 |
| C8-T1-2 | 44.19 ± 1.848 | P < 0.01 | 31.14 ± 1.486 | P < 0.001 |
| C8-T1-3 | 41.30 ± 1.720 | ns | 31.04 ± 1.360 | P < 0.001 |
| C8-T1-5 | 47.30 ± 2.822 | P < 0.002 | 33.30 ± 1.945 | P < 0.001 |
| C8-T1-6 | 50.78 ± 1.990 | P < 0.001 | 34.25 ± 1.467 | P < 0.001 |
| C8-T1-7 | 48.04 ± 2.604 | P < 0.001 | 33.19 ± 1.391 | P < 0.001 |
| C8-T1-8 | 42.90 ± 1.252 | ns | 30.13 ± 2.270 | ns |
| C8-T1-9 | 45.12 ± 1.906 | P < 0.01 | 30.56 ± 1.333 | P < 0.002 |
| C8-T1-10 | 44.60 ± 1.627 | P < 0.01 | 30.93 ± 2.002 | P < 0.01 |
| C8-T1-11 | 42.40 ± 1.891 | ns | 29.10 ± 2.998 | ns |
| C8-T1-12 | 42.57 ± 0.978 | P < 0.05 | 28.55 ± 1.190 | P < 0.05 |
| mean value | 45.093 ± 2.877 | P < 0.002 | 31.43 ± 1.886 | P < 0.001 |
| wild-type | 41.22 ± 1.005 | — | 26.76 ± 1.099 | |

TABLE 4A

Mean number of seed pods per plant, mean weight of the seed content of six pods (g), mean seed yield per plant (g), in tobacco transformed with CaMV35SAthCycD2

| Line | Mean number of seed pods | mean weight of seed content of six pods (g) | Mean seed yield per plant (g) |
|---|---|---|---|
| C8-T1-1 | 105.15 ± 14.96 | 1.085 ± 0.174 | 19.015 |
| C8-T1-2 | 127.29 ± 7.52 | 0.824 ± 0.137 | 17.481 |
| C8-T1-3 | 110.46 ± 16.30 | 1.106 ± 0.179 | 20.361 |
| C8-T1-5 | 97.86 ± 10.81 | 1.105 ± 0.178 | 18.023 |
| C8-T1-6 | 78.60 ± 12.97 | 1.078 ± 0.150 | 14.123 |
| C8-T1-7 | 118.17 ± 15.64 | 1.131 ± 0.253 | 22.275 |
| C8-T1-8 | 123.75 ± 4.78 | 1.123 ± 0.165 | 23.162 |
| C8-T1-9 | 110.83 ± 20.91 | 1.090 ± 0.218 | 20.134 |
| C8-T1-10 | 104.20 ± 10.99 | 1.122 ± 0.311 | 19.485 |
| C8-T1-11 | 138.20 ± 8.35 | 1.116 ± 0.222 | 25.705 |
| C8-T1-12 | 106.20 ± 12.62 | 1.134 ± 0.056 | 20.072 |
| wild-type | 106.73 ± 16.47 | 0.938 ± 0.118 | 16.685 |

TABLE 4B

Comparison of root development in wild-type and transgenic seedlings

| Line | Number of plants | % Lateral roots | Mean root length (mm) | Level of significance |
|---|---|---|---|---|
| 9 days after vernalization | | | | |
| WT | 23 | 36 | 15.326 ± 1.893 | |
| C8-T1-7 | 25 | 100 | 26.520 ± 1.971 | 0.001 |
|  | 3 | 33 | 14.000 ± 3.464 | ns |
| C8-T2-2 | 28 | 100 | 26.911 ± 2.064 | 0.001 |
| 13 days after vernalization | | | | |
| WT | 16 | 100 | 28.188 ± 1.893 | |
| C8-T1-7 | 13 | 100 | 53.846 ± 1.971 | 0.001 |
| C8-T2-2 | 15 | 100 | 51.267 ± 3.464 | 0.001 |

3.2, Tobacco Plants Comprising the CaMV35S-AthCycD3 Chimeric Gene.

Plants comprising the CaMV35S-AthCycD3 chimeric genes, were grown from T1 seeds and treated as described under 3.1. Measurements were started at 49 days after germination, with intervals of about 7 days. The following number of plant lines were analyzed for each line: 11 plants for line 1K9; 19 plants for line 3K9, 20 plants for line 4K9 and 18 plants for the untransformed control.

The following parameters were analyzed: the petal tube length and width (in cm) and the time (in days) at which at least 75% of the plants have reached at least the stage wherein an inflorescence is clearly developed, summarized in Table 5.

TABLE 5

Summary of the measurements on tobacco plants comprising the CaMV35SAthCycD3 chimeric gene.

| Line | Mean petal tube length (cm) | mean petal tube width (cm) | mean time required to reach inflorescence of 1 cm (days) |
|---|---|---|---|
| 1K9 | 5.66 ± 0.46 | 3.44 ± 0.27 | 100 |
| 3K9 | 5.18 ± 0.37 | 3.20 ± 0.35 | 100 |
| 4K9 | 5.48 ± 0.38 | 2.90 ± 0.35 | 93 |
| wt | 3.96 ± 0.12 | 2.39 ± 0.10 | 84 |

These transgenic plants had larger flowers, wherein the petal tube of transgenic plants was on average longer than the petal tube from flowers on untransformed plants, and also required more time to reach the stage wherein an inflorescence is clearly developed.

Example 4

Isolation of cycD-homologous Genes from Other Plants

A c-DNA library, made from exponentially growing tobacco BY-2 cells was constructed in a Lambda Zap Express vector (Stratagene). Approximately 7.5×10$^5$ library clones were plated out, and replica blots made from each plate using Hybond N$^+$ nylon membranes (Amersham Int.) which were then fixed by baking at 80° C. for two hours. The membranes were hybridized with cycD2 or cycD3 heterologous probes labelled with α-$^{32}$P dCTP by random priming. The cycD3 probe comprised a cycD3 fragment from A. thaliana (405 bp Hincll-Kpnl fragment; having the nucleotide sequence of EMBL Accesion No X83371 from nucleotide position 557 to nuceotide position 962). The cycD2 probe consisted of an 1298 bp Ncol-Sacl fragment of cycD2 from A. thaliana (having the nucleotide sequence of EMBL Accesion No X83370 from nucleotide position 194 to nuceotide position 1332), cycD3 hybridizations were carried out at 55° C. and the membranes were washed for 10 min in 2×SSC/0.1% SDS twice, followed by a single 10 min wash in 0.1 SSC/0.1% SDS prior to autoradiography. The cycD2 hybridizations were carried out at 48° C.; the membranes were washed for 10 min in 2×SSC/0.1 % SDS three times. All washes were carried out at room temperature. Isolated library clones were excised in vivo (according to the manufacturer's protocol) to generate subclones in the pBK-CMV phagemid (Stratagene) and DNA sequence was determined according to standard methods. Sequence information was analyzed using the GCG (Genetics Computer Group) Software (1994). The sequences of cycD2;1, cycD3;1 and cycD3;2 cDNAs from tobacco are represented in respectively, SEQ ID NO:1, SEQ ID NO:3, SEQ ID NO:5.

Another cDNA library was made from polyadenylated RNA isolated from tubers, roots and leaves of *Helianthus tuberosus*. The cDNA was synthesized from an oligo (dT) primer and ligated into lambda ZAPII vector at the EcpRI site.

Approximately 1.25×10⁶ clones were plated out, replica plaque blots were made as described above and hybridized using the labelled probes mentioned above. In addition the blots were screened with a cycD1 probe, comprising the 401 bp XbaI-AvaI fragment of cycD1 gene of *A. thaliana* (having the nucleotide sequence of EMBL Accesion No X83369 from nucleotide position 312 to nuceotide position 713). Isolated clones were analysed as above. The sequence of cycD1;1 and cycD3;1 genes from *Helianthus tuberosus* is represented in (SEQ ID NO:7) and (SEQ ID NO:9), respectively.

Yet another cDNA library was made from polyadenylated RNA isolated from callus material of *Zea mays* (Pa91xH99) xH99. The cDNA was synthesized from an oligo (dT) primer and ligated into lambda ZAPII vector at the EcoRI site. Approximately 1.25×10⁶ clones were plated out, replica plaque blots were made as described above and hybridized using the labelled probes mentioned above. Isolated clones were analysed as above. The sequence of the cycD2 cDNA from *Zea mays* is represented in SEQ ID NO:26.

Example 5

Construction of the Antisense Chimeric Genes and Transformation of Tobacco

A 1298 bp Ncol-Sacl fragment comprising the DNA encoding CYCD2 from *A. thaliana* (having the nucleotide sequence of EMBL Accesion No X83370 from nucleotide position 194 to nuceotide position 1332) was treated with Klenow polymerase to render the protruding termini blunt, and ligated to SmaI linearized pART7 (Gleave, 1992). A plasmid was selected wherein the inserted DNA fragment was in such an orientation that the DNA encoding the CYCD2 was introduced in the reverse way between a CaMV35S promoter of the CabbB-J1 isolate (Harpster et al., 1988) and a 3'ocs region (MacDonald et al., 1991), so that upon expression an antisense RNA is produced.

The chimeric antisense gene was then inserted between the T-DNA border of a T-DNA vector, comprising also a selectable chimeric marker gene. To this end, the chimeric cycD2 gene was excised from pCEC2, using NotI, and ligated to NotI linearized pART27 (Gleave et al., 1992) to create pCEC6.

Tobacco plants were transformed with this chimeric genes as described in Example 2.

Example 6

Analysis of the Transformants

Plants transformed with the chimeric genes of Example 5 were treated as described in Example 3.1 and the following number of plants were analyzed: 7 plants for line C9-2, and 6 plants for line C9-7.

The following parameters were analyzed: height of the plants from the soil surface to the highest point (summarized in Table 6 as mean height ± standard deviation in cm); length of the largest leaf at defined times (summarized in Table 7 as mean length ± standard deviation in cm); time (summarized in Table 8 as mean time ± standard deviation in days) at which an inflorescence merisitem is visible with the naked eye; height at which an inflorescence meristem is visible (summarized in Table 8 as mean length ± standard deviation in cm).

The transgenic plants exhibited a decreased growth rate, apparent from the seedling stage, resulting in a smaller average stem height (Table 6). The decreased growth rate also resulted on average in smaller leaves at the indicated times, which correspond to a period when leaf expansion is continuing (Table 7).

TABLE 6

Mean height (in cm) of transformed tobacco plants comprising CaMV35S-antisense cycD2

| Line   | C9-2          | C9-7          | untransformed control |
|--------|---------------|---------------|----------------------|
| Week 1 | 2.64 ± 1.22   | 2.75 ± 0.89   | 4.48 ± 1.63          |
| Week 2 | 6.64 ± 1.68   | 6.07 ± 1.43   | 10.50 ± 3.33         |
| Week 3 | 20.00 ± 3.74  | 17.21 ± 6.47  | 31.82 ± 7.89         |
| Week 4 | 34.07 ± 6.13  | 28.50 ± 5.83  | 54.00 ± 7.89         |
| Week 5 | 54.00 ± 8.87  | 45.14 ± 8.46  | 86.56 ± 10.91        |
| Week 6 | 74.29 ± 9.97  | 61.29 ± 5.11  | 121.80 ± 18.28       |
| Week 7 | 85.92 ± 12.03 | 71.50 ± 23.19 | 145.18 ± 19.44       |

TABLE 7

Difference in mean leaf length of the largest leaf of transformed tobacco plants comprising CaMV35S antisense cycD2 and the mean leaf length of the largest leaf of untransformed tobacco plants (in cm).

| Line   | C9-2  | C9-7  | untransformed control |
|--------|-------|-------|----------------------|
| Week 1 | −2.31 | −4.30 | 0                    |
| Week 2 | −3.26 | −6.44 | 0                    |
| Week 3 | −4.35 | −8.91 | 0                    |

TABLE 8A

Mean flower size (mm), mean height to infloresence (cm), mean time required to reach the development of an inflorescence (days) in tobacco transformed with CaMV35S antisense cycD2.

| Line | Mean time to inflorescence (days) | Mean height to infloresence (cm) | Mean flower length (mm) |
|------|-----------------------------------|----------------------------------|-------------------------|
| C9-2 | 102[a]                            | 95                               | NA                      |
| C9-7 | 89 ± 7.95                         | 68.57 ± 9.62                     | 38.31                   |
| untransformed control | 79 ± 2.39            | 111 ± 10.02                      | 41.22                   |

[a]Only one plant developed an inflorescence during the monitoring period.

TABLE 8B

The effect of antisense CycD2 expression on flower length of transgenic tobacco was analyzed in other lines (T1 generation) and statistically compared to wild type using the student t-test. The length of five flowers from each plant was measured and the mean flower length for each transgenic line was calculated. The values for each independent transgenic line were compared to wild type using the t-test. The table reveals the level of probability that the results are statistically significant compared to wild type.

| Line       | Mean flower length (mm) | Level of significance |
|------------|-------------------------|-----------------------|
| C9-T1-1    | 41.05 ± 1.558           | ns                    |
| C9-T1-3    | 40.68 ± 1.574           | ns                    |
| C9-T1-7    | 38.68 ± 1.991           | ns                    |
| C9-T1-10   | 39.78 ± 1.024           | P < 0.05              |
| C9-T1-12   | 39.55 ± 1.568           | P < 0.05              |
| Mean value | 40 ± 1.301              | P < 0.05              |
| wild type  | 41.22 ± 1.005           | —                     |

Example 7

Transformation of Oil Seed Rape with the T-DNAs of Example 1 and Similar Vectors and Analysis of Transformed Plants Hypocotyl explants of *Brassica napus* are obtained, cultured and transformed essentially as described by De Block et al. (1989), except for the following modifications:

hypocotyl explants are precultured for 1 day on A2 medium [MS, 0.5 g/l Mes (pH5.7), 1.2% glucose, 0.5% agarose, 1 mg/l 2,4-D, 0.25 mg/l naphthalene acetic acid (NAA)and 1 mg/l 6-benzylaminopurine (BAP)].

infection medium A3 is MS, 0.5 g/l Mes (pH5.7), 1.2% glucose, 0.1 mg/l NAA, 0.75 mg/l BAP and 0.01 mg/l gibberellinic acid (GA3).

selection medium A5G is MS, 0.5 g/l Mes (pH5.7), 1.2% glucose, 40 mg/l adenine.$SO_4$, 0.5 g/l polyvinylpyrrolidone (PVP), 0.5% agarose, 0.1 mg/l NAA, 0.75 mg/l BAP, 0.01 mg/l GA3, 250 mg/l carbenicillin, 250 mg/l triacillin, 5 mg/l $AgNO_3$ for three weeks. After this period selection is continued on A5J medium (similar a A5G but with 3% sucrose)

regeneration medium A6 is MS, 0.5 g/l Mes (pH5.7), 2% sucrose, 40 mg/l adenine.$SO_4$, 0.5 g/l PVP, 0.5% agarose, 0.0025 mg/l BAP and 250 mg/l triacillin.

healthy shoots are transferred to rooting medium which was A9: half concentrated MS, 1,5% sucrose (pH5.8), 100 mg/l triacillin, 0.6% agar in 1 liter vessels. MS stands for Murashige and Skoog medium (Murashige and Skoog, 1962).

Hypocotyl explants are infected with *Agrobacterium tumefaciens* strain C58C1Rif$^R$ carrying a helper Ti-plasmid such as pGV4000 which is a derivative of pMP90 (Koncz and Schell, 1986) obtained by insertion of a bacterial chloramphenicol resistance gene linked to a 2.5 kb fragment having homology with the T-DNA vector pGSV5, into pMP90; and a T-DNA vector derived from pGSV5 comprising between the T-DNA borders the chimeric genes of Example 1 and the chimeric marker gene (pCEC5b and pCRK9b).

Transgenic oilseed rape plants comprising the chimeric genes of the invention, exhibit an accelerated vegetative program (increased growth rate), a reduction in the time required to reach the flowering stage, an increased number of flowers and an increased seed yield per plant.

Example 8

Transformation of Corn Plants with the Vectors of Example 1 and Similar Vectors and Analysis of the Transformed Plants Corn plants are transformed with the vectors of Example 1, according to WO92/09696. Transgenic corn plants comprising the chimeric genes of the invention exhibit an accelerated vegetative program (increased growth rate), a reduction in the time required to reach the flowering stage, an increased number of flowers and an increased seed yield per plant.

Example 9

Transformation of Tomato Plants with the Vectors of Example 1 and Similar Vectors and Analysis of the Transformed Plants Tomato plants are transformed with the vectors of Example 1, according to De Block et al. (1987) Transgenic tomato plants comprising the chimeric genes of the invention exhibit an accelerated vegetative program (increased growth rate), a reduction in the time required to reach the flowering stage, an increased number of flowers and an increased fruit yield per plant.

Example 10

Transformation of Lettuce Plants with the Vectors of Example 1 and Similar Vectors and Analysis of the Transformed Plants Lettuce plants are transformed with the vectors of Example 1, according to Micheimore et al. (1987). Transgenic lettuce plants comprising the chimeric genes of the invention exhibit an accelerated vegetative program (increased growth rate), a reduction in the time required to reach the flowering stage, an increased number of flowers and an increased seed yield per plant.

Example 11

Further Phenotypic Analysis of the Progeny of the Transgenic Tobacco Lines Transformed with the CaMV35SAthCycD2 Constructs of Example 3 in Segregating and Non-segregating Populations Progeny populations (either segregating or non-segregating) of plants from two transgenic tobacco lines transformed with the CaMV35SAthCycD2 constructs (line 2 and line 5 of Example 3) were analyzed for length of time to flowering and increase in vegetative growth by measuring the mean heigth of the stem or the mean dry weight of the plants.

Segregation of the transgenes was monitored by establishing their resistance to kanamycine. For segregating populations, 32 plants were analyzed, while for non-segregating populations, 12 plants were analyzed. The non-transformed population consisted also of 12 plants.

The following populations were used:

Segregating Populations:

Line 2
C8-T1-2 [T1 seed from C8-2 primary transformant; segregates 3:1 for T-DNA]
C8-T2-2 [T2 seed from C8-T1-2 plant #3 selfed, which was hemizygous and thus seed segregates 3:1 for T-DNA]
C8-T2-2 [T2 seed from a cross of C8-T1-2 plant #3 to wild type plant using wild type as pollen parent. This seed segregates 1:1 for T-DNA, and all T-DNA containing plants are hemizygous]

Line 5
C8-T1-5 [T1 seed from C8-5 primary transformant; segregates 3:1 for T-DNA]
C8-T2-5 [T2 seed from C8-T1-5 plant #304 selfed, which was hemizygous and thus seed segregates 3:1 for T-DNA]

Non-segregating Populations

Line 2
C8-T2-2 [T2 seed from C8-T1-2 plant #302 selfed, which was homozygous for T-DNA]

Line 5
C8-T2-5 [T2 seed from C8-T1-5 plant #121 crossed to wild type plant using wild type as pollen parent. Plant #121 was homozygous for T-DNA and all T2 seed is hemizygous for the T-DNA]
C8-T2-5 [T2 seed from C8-T1-5 plant #121 selfed. Plant #121 was homozygous for T-DNA and all T2 seed is homozygous for the T-DNA].

The effect of CycD2 overexpression on the length of time to initiate inflorescence development in transgenic tobacco was measured and statistically compared to values for the same parameter measured for a wild type control population, using a non-parametric t-test in which the variances of the wt and transgenic populations were not assumed to be equal. The length of the time for each plant to develop an inflorescence of 0.5 cm was recorded and the mean number of days, post-vernalization was calculated. The values for each transgenic population was compared to the value for the wild-population using the t-test. The data for the segregating lines were separated in data for the kanamycin resistant population and the kanamycin sensitive population. The data for the kanamycin resistant population were also indicated separately for the homozygous kanamycin resistant sub-population (not further segregating) and the hemizygous kanamycin resistant subpopulation (further segregating 3:1). In Table 9 these data are summarized. Table 10 summarizes the mean values of the stem heights in transgenic non-segregating lines at different timepoints post-vernalization, in comparison with a wild type population (statistically analyzed). A significance level of less than 0.05 is considered a highly significant difference between the mean height of each transgenic line and the mean height of the controls. ns indicates there is no significant difference between the populations. In addition, the biomass of seedlings from the mentioned non-segregating populations was compared to wild type seedlings during early vegetative growth. Seedlings were harvested at the days indicated after vernalisation and weighed before drying at 70° C. for 2 days. The mean dry weight of the seedlings and standard deviation was calculated and the results are presented in Table 11.

TABLE 9

The effect of CycD2 overexpression on the length of time to initiatiate inflorescence development in transgenic tobacco

| Population | Mean time to inflorescence of 0.5 cm (days) | Standard deviation | Level of significance |
|---|---|---|---|
| Non-segregating lines | | | |
| WT | 72.125 | 2.258 | — |
| C8-T2-2 (302 selfed) | 63.62 | 3.863 | 0.001 |
| C8-T1-5 (121 selfed) | 67.78 | 2.438 | 0.02 |
| C8-T1-5 (121 × WT) | 64.18 | 1.991 | 0.001 |
| Mean value | 65.19 | 2.258 | 0.001 |
| Segregating lines | | | |
| C8-T1-2 selfed all Kan R | 59.04 | 2.973 | 0.001 |
| hemizygous | 59.32 | 3.110 | 0.001 |
| homozygous | 58.50 | 2.507 | 0.001 |
| Kanamycin sensitive | 73.00 | 5.944 | ns |
| C8-T2-2 pl 3 × WT | | | |
| Kanamycin resistant all | 59.44 | 2.756 | 0.001 |
| Kanamycin sensitive | 69.10 | 2.846 | ns |
| C8-T2-2 pl 3 selfed all Kan R | 59.20 | 2.141 | 0.001 |
| hemizygous | 59.25 | 1.653 | 0.001 |
| homozygous | 59.38 | 3.021 | 0.001 |
| Kanamycin sensitive | 73.50 | 5.431 | ns |
| C8-T1-5 All Kan R | 62.67 | 3.367 | 0.001 |
| Kanamycin sensitive | 71.50 | 5.782 | ns |
| C8-T2-5 pl 304 selfed | | | |
| hemizygous | 64.50 | 3.030 | 0.001 |
| homozygous | 65.83 | 2.483 | 0.002 |
| Kanamycin sensitive | 74.50 | 7.764 | ns |

TABLE 10

Staticstical comparison of stem height of transgenic tobacco comprising CaMV35SAthCycD2 with wild type controls

| Population | 34 days | 37 days | 41 days | 45 days | 49 days | 55 days | 63 days | 70 days | 77 days | terminal height |
|---|---|---|---|---|---|---|---|---|---|---|
| wild type | 1.48 ± 0.238 | 3.50 ± 0.831 | 7.59 ± 1.932 | 14.59 ± 3.816 | 25.81 ± 6.030 | 58.24 ± 8.423 | 107.06 ± 8.306 | 136.75 ± 7.105 | 153.94 ± 7.430 | 177.71 ± 13.129 |
| C8-T2-2 (302 selfed) | 3.55 ± 0.451 | 6.02 ± 1.662 | 11.11 ± 3.823 | 19.35 ± 6.528 | 32.81 ± 9.181 | 67.50 ± 12.281 | 120.12 ± 12.829 | 151.46 ± 15.253 | 165.23 ± 14.696 | 177.23 ± 13.935 |
| level of significance | 0.002 | 0.001 | 0.01 | 0.05 | 0.05 | 0.05 | 0.01 | 0.01 | 0.05 | ns |
| C8-T2-5 (121 selfed) | 4.25 ± 0.507 | 6.02 ± 1.662 | 11.11 ± 3.823 | 19.35 ± 6.528 | 32.81 ± 9.181 | 71.82 ± 7.604 | 119.86 ± 10.675 | 152.82 ± 11.297 | 170.73 ± 11.130 | 192.18 ± 7.846 |
| level of significance | 0.001 | 0.001 | 0.001 | 0.001 | 0.001 | 0.001 | 0.01 | 0.001 | 0.001 | 0.01 |
| C8-T2-5 (121x WT) | 4.37 ± 0.378 | 8.14 ± 1.914 | 14.76 ± 2.550 | 25.18 ± 3.314 | 39.91 ± 4.898 | 75.04 ± 6.258 | 117.83 ± 9.808 | 146.54 ± 13.422 | 160.71 ± 15.183 | 174.1 ± 14.963 |
| level of significance | 0.001 | 0.001 | 0.001 | 0.001 | 0.001 | 0.001 | 0.01 | 0.05 | ns | ns |

TABLE 11

Summary of dry weight measurements (in mg) obtained from non-segregating populations of transgenic seedlings overexpressing CycD2 and wild type (WT) seedlings at different time points post-vernilization. For all cases, the t-test indicates that there is a highly significant difference between the mean biomass of each transgenic line and the mean biomass of the controls.

| Population | 17 days | 23 days | 28 days | 34 days | 38 days |
|---|---|---|---|---|---|
| C8-T2-2 (302 selfed) | 3.75 ± 1.462 | 22.11 ± 6.59 | 53.19 ± 9.97 | 337 ± 58.3 | 530 ± 60.0 |
| C8-T2-5 (121 selfed) | 4.30 ± 1.623 | 29.05 ± 10.50 | 49.14 ± 8.51 | 351 ± 67.6 | 547 ± 24.9 |
| C8-T2-5 (121 × WT) | 5.48 ± 1.130 | 39.51 ± 10.13 | 79.81 ± 20.36 | 476 ± 120.2 | 946 ± 154 |
| Wild type | 1.2 ± 0.510 | 13.16 ± 3.09 | 29.88 ± 14.89 | 135 ± 60.72 | 382 ± 90.3 |

REFERENCES

An et al., 1985 *EMBO J.* 4: 277–284

An et al., 1988 Binary vectors in: Gelvin S B, Schilperoort R A, Verrna DPS (eds) *Plant Molecular Biology Manual* pp A3/1-A3/19. Kluwer Academic Publishers, Dordrecht).

An et al., 1996, *The Plant Cell* 8: 15–30

Ando et al., 1993, *Proc. Natl. Acad. Sci. USA* 90: 8571–9575

Atherton-Fessier et al., 1993 *Semin. Cell Biol.* 4: 433–442

Ausubel et al. 1994 *Current Protocols in Molecular Biology, Current Protocols*, USA.

Baldin et al. 1993 *Genes Dev.* 7: 812–821

Ballas et al. 1989 *Nucl. Acids Res.* 17: 7891–7903

Bernards et al. 1989 *Proc. Natl. Acad. Sci. USA* 86: 6474–6478

Boehmelt et al. 1994 *Cell Growth Differ.* 5: 221–230

Chiatante et al. 1993 *Plant Sci.* 89: 13–21

Colasanti et al. 1991 *Proc. Natl. Acad. Sci. USA* 88: 3377–3381

Colasanti et al. 1993 *Plant Cell* 5: 1101–1111

Cornelissen and Vandewiele 1989 *Nucl. Acids Res.* 17: 833

Cross 1988, *Mol. Cell. Biol.* 8: 4675–4684

Croy 1993 *Plant Molecular Biology Labfax BIOS Scientific Publications Ltd (UK) and Blackwell Scientific Publications, UK.*

Dahl et al. 1995 *Plant Cell* 7: 1847–1857

Day and Reddy 1994 *Biochim. Biophys. Acta Gene Struct. Express.* 1218: 115–118

De Almeida et al. 1989 *Mol. Gen. Genet.* 218: 78–86

De Block et al. 1987 Embo J. 6: 2513–2518

De Block et al. 1989 *Plant Physiol.* 91: 694

De Greve et al. 1982 *J. Mol. Appl. Genet.* 1: 499

Depicker et al. 1982 *J. Mol. Appl. Genet.* 1: 561

Destree et al. 1992 Dev Biol. 153: 141–149

Dirick and Nasmyth 1991 *Nature* 351: 754–757

Ditta et al. 1980 *Proc. Natl. Acad. Sci. USA* 77: 7347–7351

Doerner et al. 1996 *Nature* 380: 520–523

Doonan et al. 1998 in "*Plant Cell Division*" (Francis, Duditz and Inze, Eds.) Portland Press, London.

Dowdy et al. 1993 *Cell* 73: 499–511

Du et al. 1996 *Genes and Development* 10: 1206–1218

Durfee et al. 1993 *Genes and Development* 7:555–569

Evans and van't Hof, 1974 *Exp. Cell Res.* 87: 259–264

Evans et al., 1983 *Cell* 33: 389–396

Ewen et al. 1991 *Cell* 66: 1155–1164

Ewen et al. 1993 *Cell* 73: 487–497

Fang and Newport 1991 *Cell* 66: 731–742

Feiler and Jacobs 1990 *Proc. Natl. Acad. Sci. USA* 87: 5397–5401

Feilloter et al. 1994 *Nucl. Acids Res.* 22: 1502–1503

Ferreira et al. 1991 *Plant Cell* 3: 531–540

Fields and Song 1989 *Nature* 340: 245–246

Fobert et al. 1994 *EMBO J.* 13: 616–624

Fromm et al. 1990 *Bio/Technology* 8: 833

Fuerst et al. 1996 *Plant Physiol.* 112: 1023–1033

Gallie et al. 1987 *Nucl. Acids Res.* 15: 3257–3273

Gleave 1992 *Plant Mol. Biol.* 20: 1203–1207

Gordon-Kamm et al. 1990 *The Plant Cell* 2: 603

Gould et al. 1981 *Protoplasma* 106: 1–13

Grafi and Larkins 1995 *Science* 269: 1262–1264

Grafi et al. 1996 *Proc. Natl. Acad. Sci. USA* 93: 8962–8967

Guerineau et al. 1991 *Mol. Gen. Genet.* 226:141–144

Hannon et al. 1993 *Genes Dev.* 7: 2378–2391

Hata et al. 1991 *EMBO J* 10: 2681–2688

Harper et al. 1993 *Cell* 75: 805–816

Harpster et al. 1988 *Mol. Gen. Genet.* 212: 182–190

Hartwell 1974 *Bacteriol. Rev.* 38: 164–198

Hemerly et al. 1992 *Proc. Natl. Acad. Sci. USA* 89: 3295–3299

Hemerly et al. 1995 *EMBO J.* 14: 3295–3299

Hirayama et al. 1991 *Gene* 105: 159–165

Hirt et al., 1991 *Proc. Natl. Acad. Sci. USA* 88: 1636–1640

Hirt et al., 1992 *Plant Cell* 4: 1531–1538

Hirt et al. 1993 *Plant J.* 4: 61–69

Howard and Pelc, 1953 *Heredity* 6 (suppl.): 216–273

Hudspeth et al. 1989 *Plant Mol Biol* 12: 579–589

John et al. 1989 *Plant Cell* 1: 1185–1193

John et al. 1990 *J. Cell Sci.* 97: 627–630

John et al. 1991 *Protoplasma* 161: 70–74

Johnson et al., 1993 *Nature* 365: 349–352

Jones et al. 1992 *Transgen. Research* 1: 285–297

Joshi et al. 1987 *Nucl. Acids Res.* 15: 9627–9639

Joshi 1987 *Nucl. Acids Res.* 15: 6643–6653

Keil et al., 1989 *EMBO J.* 8: 1323–1330

Keller et al. 1988 *EMBO J.* 7: 3625–3633

Keller et al. 1989 *Genes. Devel.* 3: 1639–1646

Klapwijk et al. 1980 *J. Bacterial.* 141: 128–136

Koff et al. 1991 *Cell* 66: 1217–1228

Koff et al. 1992 *Science* 257: 1689–1694

Koff et al. 1993 *Science* 260: 536–539

Koncz and Schell 1986 *Mol. Gen. Genet.* 204: 383

Lahue et al. 1991 *Genes Dev.* 5: 2166–2175

Leopold and O'Farrell 1991 *Cell* 66: 1207–1216
Lee et al. 1987 *Nature* 329: 642–645
Lew et al. 1991 *Cell* 66: 1197–1206
Long et al. 1996 *Nature* 379: 66–69
Luehrsen and Walbot 1991 *Mol. Gen. Genet.* 225: 81–93
MacDonald et al. 1991 *Nucl. Acids. Res.* 19: 5575–5581
Matsushime et al. 1991 *Cell* 65: 701–713
Matsushime et al. 1992 *Cell* 71: 323–334
Meyer et al. 1987 *Nature* 330: 677
Meyerson and Harlow 1994 *Mol. Cell. Biol.* 14: 2077–2086
Meyerson et al. 1991 *Cold Spring Harbor Symp. Quant. Biol.* 56: 177–186
Meyerson et al. 1992 *EMBO J.* 11: 2909–2917
Miao et al. 1993 *Proc. Natl. Acad. Sci. USA* 90: 943–947
Micheimore et al. 1987 *Plant Cell Rep.* 6: 439–442
Mineyuki et al. 1991 *Protoplasma* 162: 182–186
Mogen et al. 1990 *Plant Cell*, 2: 1261–1272
Munroe et al. 1990 *Gene*, 91: 151–158
Murashige and Skoog 1962 *Physiol. Plant.* 15: 473
Murray et al. 1989 *Nature* 339: 280–286
Nasmyth 1993 *Curr. Opin. Cell. Biol.* 5: 166–179
Nevins 1992 *Science* 258: 424–429
Nurse 1990 *Nature* 344: 503–508
Ohtsubo and Roberts 1993 *Science* 259: 1908–1912
O'Reilly et al., 1992. *Baculovirus expression vectors—A Laboratory manual.* Freeman and Co. New York
Pardee 1989 *Science* 246: 603–608
Peleman et al. 1989 *Gene* 84: 359–369
Phelps et al. 1992 *J. Virol.* 66: 2418–2427
Pines, 1993 *Trends Biochem. Sci.* 18: 195–197
Pines 1995 *Biochem J.* 308: 697–711
Pines 1995 *Adv. Cancer Res.* 66: 181–212
Proudfoot 1991 *Cell*, 64:671–674
Quelle et al. 1993 Genes Dev. 7: 1559–1571
Rechsteiner 1990 *Seminars Cell Biol.* 1: 433–440
Reed 1991 *Trends Genet.* 7: 95–99
Renaudin et al. 1994 *Proc. Natl. Acad. Sci. USA* 91: 7375–7379
Renaudin et al. 1996 *Plant Molecular Biology* 32: 1003–1018
Richardson et al., 1989 *Cell* 59:1127–113
Rogers et al. 1986 *Science* 234: 364–368
Safacon et al. 1991 *Genes Dev* 5: 141–149
Salama et al. 1994 *Mol. Cell. Biol.* 14: 7953–7966
Sambrook et al. 1989 *Molecular Cloning: A Laboratory Manual, Second Edition,* Cold Spring Harbor Laboratory Press, NY
Sewing et al. 1993 *J. Cell. Sci.* 104: 545–555
Snedecor and Cochran 1967 *Statistical Methods* The Iowa State University Press, Ames, Iowa, U.S.A.
Solomon 1993 *Curr. Opin. Cell Biol.* 5: 180–186
Soni et al. 1995 *The Plant Cell* 7: 85–103
Tsai et al. 1993a Development 119: 1029–1040
Tsai et al. 1993b Oncogene 8: 1593–1602
Tyers et al. 1992 *EMBO J.* 11: 1773–1784
Tyers et al., 1993 *EMBO J.* 12: 1955–1968
van den Heuvel and Harlow 1993 *Science* 262: 2050–2054
van't Hof and Kovacs 1972 In The Dynamics of Meristem Cell Populations, M. W. Miller and C C Keuhnert, eds (NY: Plenum) pp 15–32
van't Hof, 1985 In The Cell Division Cycle in Plants, J. A. Bryant and D. Francis, eds (Cambridge: Cambridge University Press) pp 1-13
Velten and Schell 1985 *Nucl. Acids Res.* 13: 6998
Walkerpeach and Velten 1995 In: Gelvin S B, Schilperoort R A, Verma D P S (eds) Plant Molecular Biology Manual pp B1/1-B1/19. Kluwer Academic Publishers, Dordrecht Wilbur and Lipmann 1983 *Proc. Nat. Acad. Sci. U.S.A.* 80: 726
Wimmel et al. 1994 *Oncogene* 9: 995–997
Wittenberg and Reed 1988 *Cell* 54:1061–1072
Wittenberg et al. 1990 *Cell* 62: 225–237
Xie et al. 1996 *EMBO J.* 15: 49004908
Xiong et al., 1992 *Cell* 71: 505–514
Xiong et al., 1991 *Cell* 65: 691–699

What is claimed is:

1. A process to obtain a plant which flowers later than a wild-type plant, said process comprising the step of transforming cells of said plant with a chimeric gene comprising the following operably linked DNA fragments:
   a) a plant expressible promoter region;
   b) a transcribed DNA region encoding a D-type cyclin which is *Arabidopsis thaliana* CYCD3, said transcribed DNA region comprising the nucleotide sequence of SEQ ID No. 31 from the nucleotide position 266 to the nucleotide position 1396; and
   c) a 3' end formation and a polyadenylation signal functional in plant cells.

2. The process of claim 1, wherein said plant expressible promoter region is a CaMV35S promoter region.

3. A chimeric gene as described in claim 1.

4. A plant cell, comprising the chimeric gene of claim 3.

5. A plant, consisting essentially of the plant cells of claim 4.

6. The plant of claim 5, which is a greenhouse-grown plant.

7. A seed of the plant of claim 5, said seed comprising the chimeric gene of claim 3.

* * * * *

SEQUENCE LISTING

<160> NUMBER OF SEQ ID NOS: 32

<210> SEQ ID NO 1
<211> LENGTH: 1284
<212> TYPE: DNA
<213> ORGANISM: Nicotiana tabacum
<220> FEATURE:
<221> NAME/KEY: CDS
<222> LOCATION: (182)..(1243)
<223> OTHER INFORMATION:

<400> SEQUENCE: 1

```
caaattttc tcccttctat agtctctttc ctgttctctt aaaaatcctt aaaaatttat      60 ttttttaac aatctcatgt aaatgggatt aaattttgta aaaatataag attttgataa     120 aggggttta attataacat agtaaattaa gattttttt ttgctttgct agtttgcttt      180 a atg gca gct gat aac att tat gat ttt gta gcc tca aat ctt tta tgt   229
```

-continued

```
    Met Ala Ala Asp Asn Ile Tyr Asp Phe Val Ala Ser Asn Leu Leu Cys
    1               5                   10                  15 aca gaa aca aaa agt ctt tgt ttt gat gat gtt gat tct ttg act ata          277
Thr Glu Thr Lys Ser Leu Cys Phe Asp Asp Val Asp Ser Leu Thr Ile
            20                  25                  30 agt caa cag aac att gaa act aag agt aaa gac ttg agc ttt aac aat          325
Ser Gln Gln Asn Ile Glu Thr Lys Ser Lys Asp Leu Ser Phe Asn Asn
        35                  40                  45 ggt att aga tca gag cca ttg att gat ttg cca agt tta agt gaa gaa          373
Gly Ile Arg Ser Glu Pro Leu Ile Asp Leu Pro Ser Leu Ser Glu Glu
50                  55                  60 tgc ttg agt ttt atg gtg caa agg gaa atg gag ttt ttg cct aaa gat          421
Cys Leu Ser Phe Met Val Gln Arg Glu Met Glu Phe Leu Pro Lys Asp
65                  70                  75                  80 gat tat gtc gag aga ttg aga agt gga gat ttg gat ttg agt gtg aga          469
Asp Tyr Val Glu Arg Leu Arg Ser Gly Asp Leu Asp Leu Ser Val Arg
                85                  90                  95 aaa gag gct ctt gat tgg att ttg aag gct cat atg cac tat gga ttt          517
Lys Glu Ala Leu Asp Trp Ile Leu Lys Ala His Met His Tyr Gly Phe
            100                 105                 110 gga gag ctg agt ttt tgt ttg tcg ata aat tac ttg gat cga ttt cta          565
Gly Glu Leu Ser Phe Cys Leu Ser Ile Asn Tyr Leu Asp Arg Phe Leu
        115                 120                 125 tct ctg tat gaa ttg cca aga agt aaa act tgg aca gtg caa ttg tta          613
Ser Leu Tyr Glu Leu Pro Arg Ser Lys Thr Trp Thr Val Gln Leu Leu
130                 135                 140 gct gtg gcc tgt cta tca ctt gca gcc aaa atg gaa gaa att aat gtt          661
Ala Val Ala Cys Leu Ser Leu Ala Ala Lys Met Glu Glu Ile Asn Val
145                 150                 155                 160 cct ttg act gtt gat tta cag gta ggg gat ccc aaa ttt gta ttt gaa          709
Pro Leu Thr Val Asp Leu Gln Val Gly Asp Pro Lys Phe Val Phe Glu
                165                 170                 175 ggc aaa act ata caa aga atg gaa ctt ttg gta tta agc aca ttg aag          757
Gly Lys Thr Ile Gln Arg Met Glu Leu Leu Val Leu Ser Thr Leu Lys
            180                 185                 190 tgg aga atg caa gct tat aca cct tac aca ttc ata gat tat ttt atg          805
Trp Arg Met Gln Ala Tyr Thr Pro Tyr Thr Phe Ile Asp Tyr Phe Met
        195                 200                 205 aga aag atg aat ggt gat caa atc cca tct cgg ccg ttg att tct gga          853
Arg Lys Met Asn Gly Asp Gln Ile Pro Ser Arg Pro Leu Ile Ser Gly
210                 215                 220 tca atg caa ctg ata tta agc ata ata aga agt att gat ttc ttg gaa          901
Ser Met Gln Leu Ile Leu Ser Ile Ile Arg Ser Ile Asp Phe Leu Glu
225                 230                 235                 240 ttc agg tct tct gaa att gca gca tca gtg gca atg tct gtt tca ggg          949
Phe Arg Ser Ser Glu Ile Ala Ala Ser Val Ala Met Ser Val Ser Gly
                245                 250                 255 gaa ata caa gca aaa gac att gat aag gca atg cct tgc ttc ttc ata          997
Glu Ile Gln Ala Lys Asp Ile Asp Lys Ala Met Pro Cys Phe Phe Ile
            260                 265                 270 cac tta gac aag ggt aga gtg cag aag tgt gtt gaa ctg att caa gat         1045
His Leu Asp Lys Gly Arg Val Gln Lys Cys Val Glu Leu Ile Gln Asp
        275                 280                 285 ttg aca act gct act att act act gct gct gct gcc tca tta gta cct         1093
Leu Thr Thr Ala Thr Ile Thr Thr Ala Ala Ala Ala Ser Leu Val Pro
290                 295                 300 caa agt cct att gga gtg ttg gaa gca gca gca tgc ttg agc tac aaa         1141
Gln Ser Pro Ile Gly Val Leu Glu Ala Ala Ala Cys Leu Ser Tyr Lys
                305                 310                 315                 320
```

```
agt ggt gat gag aga aca gtt gga tca tgt aca act tct tca cat act   1189
Ser Gly Asp Glu Arg Thr Val Gly Ser Cys Thr Thr Ser Ser His Thr
            325                 330                 335 aaa agg aga aaa ctt gac aca tca tct tta gag cat ggg act tca gaa   1237
Lys Arg Arg Lys Leu Asp Thr Ser Ser Leu Glu His Gly Thr Ser Glu
            340                 345                 350 aag ttg tgaatctgaa ttttcccttt ttaaaaaaaa aaaaaaaaaa a             1284
Lys Leu
```

<210> SEQ ID NO 2
<211> LENGTH: 354
<212> TYPE: PRT
<213> ORGANISM: Nicotiana tabacum

<400> SEQUENCE: 2

```
Met Ala Ala Asp Asn Ile Tyr Asp Phe Val Ala Ser Asn Leu Leu Cys
  1               5                  10                  15

Thr Glu Thr Lys Ser Leu Cys Phe Asp Asp Val Asp Ser Leu Thr Ile
                 20                  25                  30

Ser Gln Gln Asn Ile Glu Thr Lys Ser Lys Asp Leu Ser Phe Asn Asn
             35                  40                  45

Gly Ile Arg Ser Glu Pro Leu Ile Asp Leu Pro Ser Leu Ser Glu Glu
         50                  55                  60

Cys Leu Ser Phe Met Val Gln Arg Glu Met Glu Phe Leu Pro Lys Asp
 65                  70                  75                  80

Asp Tyr Val Glu Arg Leu Arg Ser Gly Asp Leu Asp Leu Ser Val Arg
                 85                  90                  95

Lys Glu Ala Leu Asp Trp Ile Leu Lys Ala His Met His Tyr Gly Phe
            100                 105                 110

Gly Glu Leu Ser Phe Cys Leu Ser Ile Asn Tyr Leu Asp Arg Phe Leu
            115                 120                 125

Ser Leu Tyr Glu Leu Pro Arg Ser Lys Thr Trp Thr Val Gln Leu Leu
        130                 135                 140

Ala Val Ala Cys Leu Ser Leu Ala Ala Lys Met Glu Glu Ile Asn Val
145                 150                 155                 160

Pro Leu Thr Val Asp Leu Gln Val Gly Asp Pro Lys Phe Val Phe Glu
                165                 170                 175

Gly Lys Thr Ile Gln Arg Met Glu Leu Leu Val Leu Ser Thr Leu Lys
            180                 185                 190

Trp Arg Met Gln Ala Tyr Thr Pro Tyr Thr Phe Ile Asp Tyr Phe Met
            195                 200                 205

Arg Lys Met Asn Gly Asp Gln Ile Pro Ser Arg Pro Leu Ile Ser Gly
        210                 215                 220

Ser Met Gln Leu Ile Leu Ser Ile Ile Arg Ser Ile Asp Phe Leu Glu
225                 230                 235                 240

Phe Arg Ser Ser Glu Ile Ala Ala Ser Val Ala Met Ser Val Ser Gly
                245                 250                 255

Glu Ile Gln Ala Lys Asp Ile Asp Lys Ala Met Pro Cys Phe Phe Ile
            260                 265                 270

His Leu Asp Lys Gly Arg Val Gln Lys Cys Val Glu Leu Ile Gln Asp
        275                 280                 285

Leu Thr Thr Ala Thr Ile Thr Thr Ala Ala Ala Ser Leu Val Pro
    290                 295                 300

Gln Ser Pro Ile Gly Val Leu Glu Ala Ala Ala Cys Leu Ser Tyr Lys
305                 310                 315                 320
```

-continued

```
Ser Gly Asp Glu Arg Thr Val Gly Ser Cys Thr Thr Ser Ser His Thr
            325                 330                 335

Lys Arg Arg Lys Leu Asp Thr Ser Ser Leu Glu His Gly Thr Ser Glu
            340                 345                 350

Lys Leu

<210> SEQ ID NO 3
<211> LENGTH: 1679
<212> TYPE: DNA
<213> ORGANISM: Nicotiana tabacum
<220> FEATURE:
<221> NAME/KEY: CDS
<222> LOCATION: (181)..(1299)
<223> OTHER INFORMATION: cDNA encoding cyclin CYCD3;1

<400> SEQUENCE: 3
aaacgagtct ctgtgtactc ctcctcctat agcttttctc tcttcttctc ttcacacctc      60
ccacaacaca caatcagaca aaatagagag gaaaatgagt atggtgaaaa agctttgttt     120
tgtataatga gaaaagaga tttatataca tctcttcttc tacttccttc ttactagaag     180 atg gca ata gaa cac aat gag caa caa gaa cta tct caa tct ttt ctt      228
Met Ala Ile Glu His Asn Glu Gln Gln Glu Leu Ser Gln Ser Phe Leu
  1               5                  10                  15 tta gat gct ctt tac tgt gaa gaa gaa gaa gaa aaa tgg gga gat tta      276
Leu Asp Ala Leu Tyr Cys Glu Glu Glu Glu Glu Lys Trp Gly Asp Leu
             20                  25                  30 gta gat gat gag act att att aca cca ctc tct tca gaa gta aca aca      324
Val Asp Asp Glu Thr Ile Ile Thr Pro Leu Ser Ser Glu Val Thr Thr
         35                  40                  45 aca aca aca aca aca aca aag cct aat tct tta tta cct ttg ctt ttg      372
Thr Thr Thr Thr Thr Thr Lys Pro Asn Ser Leu Leu Pro Leu Leu Leu
     50                  55                  60 ttg gaa caa gat tta ttt tgg gaa gat gaa gag ctt ctt tca ctt ttc      420
Leu Glu Gln Asp Leu Phe Trp Glu Asp Glu Glu Leu Leu Ser Leu Phe
 65                  70                  75                  80 tct aaa gaa aaa gaa acc cat tgt tgg ttt aac agt ttt caa gat gac      468
Ser Lys Glu Lys Glu Thr His Cys Trp Phe Asn Ser Phe Gln Asp Asp
                 85                  90                  95 tct tta ctc tgt tct gcc cgt gtt gat tct gtg gaa tgg att tta aaa      516
Ser Leu Leu Cys Ser Ala Arg Val Asp Ser Val Glu Trp Ile Leu Lys
            100                 105                 110 gtg aat ggt tat tat ggt ttc tct gct ttg act gcc gtt tta gcc ata      564
Val Asn Gly Tyr Tyr Gly Phe Ser Ala Leu Thr Ala Val Leu Ala Ile
        115                 120                 125 aat tac ttt gac agg ttt ctg act agt ctt cat tat cag aaa gat aaa      612
Asn Tyr Phe Asp Arg Phe Leu Thr Ser Leu His Tyr Gln Lys Asp Lys
    130                 135                 140 cct tgg atg att caa ctt gct gct gtt act tgt ctt tct tta gct gct      660
Pro Trp Met Ile Gln Leu Ala Ala Val Thr Cys Leu Ser Leu Ala Ala
145                 150                 155                 160 aaa gtt gaa gaa act caa gtt cct ctt ctt tta gat ttt caa gtg gag      708
Lys Val Glu Glu Thr Gln Val Pro Leu Leu Leu Asp Phe Gln Val Glu
                165                 170                 175 gat gct aaa tat gtg ttt gag gca aaa act att caa aga atg gag ctt      756
Asp Ala Lys Tyr Val Phe Glu Ala Lys Thr Ile Gln Arg Met Glu Leu
            180                 185                 190 tta gtg ttg tct tca cta aaa tgg agg atg aat cca gtg acc cca ctt      804
Leu Val Leu Ser Ser Leu Lys Trp Arg Met Asn Pro Val Thr Pro Leu
        195                 200                 205 tca ttt ctt gat cat att ata agg agg ctt ggg cta aga aat aat att      852
```

```
Ser Phe Leu Asp His Ile Ile Arg Arg Leu Gly Leu Arg Asn Asn Ile
    210                 215                 220 cac tgg gaa ttt ctt aga aga tgt gaa aat ctc ctc ctc tct att atg    900
His Trp Glu Phe Leu Arg Arg Cys Glu Asn Leu Leu Leu Ser Ile Met
225                 230                 235                 240 gct gat tgt aga ttc gta cgt tat atg ccg tct gta ttg gcc act gca    948
Ala Asp Cys Arg Phe Val Arg Tyr Met Pro Ser Val Leu Ala Thr Ala
                    245                 250                 255 att atg ctt cac gtt att cat caa gtt gag cct tgt aat tct gtt gac    996
Ile Met Leu His Val Ile His Gln Val Glu Pro Cys Asn Ser Val Asp
            260                 265                 270 tac caa aat caa ctt ctt ggg gtt ctc aaa att aac aag gag aaa gtg    1044
Tyr Gln Asn Gln Leu Leu Gly Val Leu Lys Ile Asn Lys Glu Lys Val
        275                 280                 285 aat aat tgc ttt gaa ctc ata tca gaa gtg tgt tct aag ccc att tca    1092
Asn Asn Cys Phe Glu Leu Ile Ser Glu Val Cys Ser Lys Pro Ile Ser
    290                 295                 300 cac aaa cgc aaa tat gag aat cct agt cat agc cca agt ggt gta att    1140
His Lys Arg Lys Tyr Glu Asn Pro Ser His Ser Pro Ser Gly Val Ile
305                 310                 315                 320 gat cca att tac agt tca gaa agt tca aat gat tca tgg gat ttg gag    1188
Asp Pro Ile Tyr Ser Ser Glu Ser Ser Asn Asp Ser Trp Asp Leu Glu
                    325                 330                 335 tca aca tct tca tat ttt cct gtt ttc aag aaa agc aga gta caa gaa    1236
Ser Thr Ser Ser Tyr Phe Pro Val Phe Lys Lys Ser Arg Val Gln Glu
            340                 345                 350 cag caa atg aaa ttg gca tct tca att agc aga gtt ttt gtg gaa gct    1284
Gln Gln Met Lys Leu Ala Ser Ser Ile Ser Arg Val Phe Val Glu Ala
        355                 360                 365 gtt ggt agt cct cat taaaatcaat cacctgattt atctcttttc tttcttatta   1339
Val Gly Ser Pro His
    370 ccaactatgg tggtaataat atttattgat attcagaagt atttaccttt aatgtcattt   1399 tcaaaaatta catgaaaatg gaaaaaaaga aagaagagc ttagctggtg gttgcagttg    1459 gcagagaaga ggactggctt tttttgcag gagtgtagtc tactactact ggaaagcaga    1519 gatagagaga ggagaaaaga cagaaaatct gcactatttg tttttctct attcatatca    1579 attctctctt aggtcctttt catgcatgca tactttttgat ggacatattt tatatattta   1639 ctataatcat aaattcttga ataaaaaaaa aaaaaaaaa                          1679

<210> SEQ ID NO 4
<211> LENGTH: 373
<212> TYPE: PRT
<213> ORGANISM: Nicotiana tabacum

<400> SEQUENCE: 4

Met Ala Ile Glu His Asn Glu Gln Gln Glu Leu Ser Gln Ser Phe Leu
1               5                   10                  15

Leu Asp Ala Leu Tyr Cys Glu Glu Glu Glu Lys Trp Gly Asp Leu
                20                  25                  30

Val Asp Asp Glu Thr Ile Ile Thr Pro Leu Ser Ser Glu Val Thr Thr
            35                  40                  45

Thr Thr Thr Thr Thr Thr Lys Pro Asn Ser Leu Leu Pro Leu Leu Leu
        50                  55                  60

Leu Glu Gln Asp Leu Phe Trp Glu Asp Glu Glu Leu Leu Ser Leu Phe
65                  70                  75                  80

Ser Lys Glu Lys Glu Thr His Cys Trp Phe Asn Ser Phe Gln Asp Asp
```

```
                    85                  90                  95
Ser Leu Leu Cys Ser Ala Arg Val Asp Ser Val Glu Trp Ile Leu Lys
                100                 105                 110

Val Asn Gly Tyr Tyr Gly Phe Ser Ala Leu Thr Ala Val Leu Ala Ile
            115                 120                 125

Asn Tyr Phe Asp Arg Phe Leu Thr Ser Leu His Tyr Gln Lys Asp Lys
        130                 135                 140

Pro Trp Met Ile Gln Leu Ala Ala Val Thr Cys Leu Ser Leu Ala Ala
145                 150                 155                 160

Lys Val Glu Glu Thr Gln Val Pro Leu Leu Asp Phe Gln Val Glu
                165                 170                 175

Asp Ala Lys Tyr Val Phe Glu Ala Lys Thr Ile Gln Arg Met Glu Leu
            180                 185                 190

Leu Val Leu Ser Ser Leu Lys Trp Arg Met Asn Pro Val Thr Pro Leu
        195                 200                 205

Ser Phe Leu Asp His Ile Ile Arg Arg Leu Gly Leu Arg Asn Asn Ile
    210                 215                 220

His Trp Glu Phe Leu Arg Arg Cys Glu Asn Leu Leu Ser Ile Met
225                 230                 235                 240

Ala Asp Cys Arg Phe Val Arg Tyr Met Pro Ser Val Leu Ala Thr Ala
                245                 250                 255

Ile Met Leu His Val Ile His Gln Val Glu Pro Cys Asn Ser Val Asp
            260                 265                 270

Tyr Gln Asn Gln Leu Leu Gly Val Leu Lys Ile Asn Lys Glu Lys Val
        275                 280                 285

Asn Asn Cys Phe Glu Leu Ile Ser Glu Val Cys Ser Lys Pro Ile Ser
    290                 295                 300

His Lys Arg Lys Tyr Glu Asn Pro Ser His Ser Pro Ser Gly Val Ile
305                 310                 315                 320

Asp Pro Ile Tyr Ser Ser Glu Ser Ser Asn Asp Ser Trp Asp Leu Glu
                325                 330                 335

Ser Thr Ser Ser Tyr Phe Pro Val Phe Lys Lys Ser Arg Val Gln Glu
            340                 345                 350

Gln Gln Met Lys Leu Ala Ser Ser Ile Ser Arg Val Phe Val Glu Ala
        355                 360                 365

Val Gly Ser Pro His
    370

<210> SEQ ID NO 5
<211> LENGTH: 1431
<212> TYPE: DNA
<213> ORGANISM: Nicotiana tabacum
<220> FEATURE:
<221> NAME/KEY: CDS
<222> LOCATION: (198)..(1298)
<223> OTHER INFORMATION: cDNA encoding cyclin CYCD3;2

<400> SEQUENCE: 5
cacctttact ctcttctcct ttttggctct tcccattctc tccttctctt tctttatttt      60
ctgtcctgta gagagagaga gaaagtataa gcaaagcagc agatatgtta ctgggtccaa     120
gattgagttt tggcttacct tgaagataat gagtagagcc tccattgtct tcttccgtca     180
agaagaagaa gaagaag atg gtt ttc cct tta gat act cag ctc cta aat        230
                   Met Val Phe Pro Leu Asp Thr Gln Leu Leu Asn
                    1               5                   10 cca atc ttt gat gtc ctt tac tgt gag gaa gat cga ttc ttg gac gat       278
```

```
                Pro Ile Phe Asp Val Leu Tyr Cys Glu Glu Asp Arg Phe Leu Asp Asp
                            15                  20                  25 gat gat tta gga gaa tgg tct agt act tta gaa caa gta gga aat aat          326
Asp Asp Leu Gly Glu Trp Ser Ser Thr Leu Glu Gln Val Gly Asn Asn
            30                  35                  40 gtg aaa aag act cta cct tta tta gaa tgt gac atg ttt tgg gaa gat          374
Val Lys Lys Thr Leu Pro Leu Leu Glu Cys Asp Met Phe Trp Glu Asp
        45                  50                  55 gac cag ctt gtc act ctt tta act aag gaa aaa gag tct cat ttg ggt          422
Asp Gln Leu Val Thr Leu Leu Thr Lys Glu Lys Glu Ser His Leu Gly
 60                  65                  70                  75 ttt gat tgt tta atc tca gat gga gat ggg ttt tta gtg gag gtt aga          470
Phe Asp Cys Leu Ile Ser Asp Gly Asp Gly Phe Leu Val Glu Val Arg
                80                  85                  90 aaa gag gca ttg gat tgg atg ttg aga gtc att gct cac tat ggt ttc          518
Lys Glu Ala Leu Asp Trp Met Leu Arg Val Ile Ala His Tyr Gly Phe
            95                 100                 105 act gct atg act gct gtt tta gct gtg aat tat ttt gat agg ttt gta          566
Thr Ala Met Thr Ala Val Leu Ala Val Asn Tyr Phe Asp Arg Phe Val
        110                 115                 120 tct gga ctc tgc ttt cag aaa gat aag cct tgg atg agt caa ctt gct          614
Ser Gly Leu Cys Phe Gln Lys Asp Lys Pro Trp Met Ser Gln Leu Ala
125                 130                 135 gct gtg gct tgt ctt tct att gct gct aaa gtg gaa gag acc caa gtc          662
Ala Val Ala Cys Leu Ser Ile Ala Ala Lys Val Glu Glu Thr Gln Val
140                 145                 150                 155 ccc ctt ctc tta gac ctc caa gtg gct gat tca aga ttt gtg ttt gag          710
Pro Leu Leu Leu Asp Leu Gln Val Ala Asp Ser Arg Phe Val Phe Glu
                160                 165                 170 gca aag act att cag aga atg gaa ctc ttg gtg ctc tcc act ctt aag          758
Ala Lys Thr Ile Gln Arg Met Glu Leu Leu Val Leu Ser Thr Leu Lys
            175                 180                 185 tgg aaa atg aat cca gtg aca cca cta tct ttc att gat cat atc atg          806
Trp Lys Met Asn Pro Val Thr Pro Leu Ser Phe Ile Asp His Ile Met
        190                 195                 200 agg aga ttt gga ttc atg acc aat cta cat ttg gat ttt ctt agg aga          854
Arg Arg Phe Gly Phe Met Thr Asn Leu His Leu Asp Phe Leu Arg Arg
    205                 210                 215 tgt gaa cgc ctc att ctt ggt att atc act gat tct agg ctc ttg cat          902
Cys Glu Arg Leu Ile Leu Gly Ile Ile Thr Asp Ser Arg Leu Leu His
220                 225                 230                 235 tat cct cca tct gtt att gca act gca gta gtg tat ttc gtg atc aat          950
Tyr Pro Pro Ser Val Ile Ala Thr Ala Val Val Tyr Phe Val Ile Asn
                240                 245                 250 gag att gag cct tgc aat gca atg gaa tac cag aat cag ctc atg act          998
Glu Ile Glu Pro Cys Asn Ala Met Glu Tyr Gln Asn Gln Leu Met Thr
            255                 260                 265 gtt ctt aaa gtc aaa cag gat agt ttt gaa gaa tgc cat gat ctt att         1046
Val Leu Lys Val Lys Gln Asp Ser Phe Glu Glu Cys His Asp Leu Ile
        270                 275                 280 cta gag cta atg ggc act tct ggc tac aat atc tgc caa agc ctc aag         1094
Leu Glu Leu Met Gly Thr Ser Gly Tyr Asn Ile Cys Gln Ser Leu Lys
    285                 290                 295 cgc aaa cat caa tct gta cct ggc agt cca agt gga gtt atc gat gca         1142
Arg Lys His Gln Ser Val Pro Gly Ser Pro Ser Gly Val Ile Asp Ala
300                 305                 310                 315 tat ttt agt tgc gac agc tct aat gat tcg tgg tcg gta gca tct tca         1190
Tyr Phe Ser Cys Asp Ser Ser Asn Asp Ser Trp Ser Val Ala Ser Ser
                320                 325                 330
```

```
att tca tcg tca cca gaa cct cag tat aag agg atc aaa act cag gat      1238
Ile Ser Ser Ser Pro Glu Pro Gln Tyr Lys Arg Ile Lys Thr Gln Asp
        335                 340                 345 cag aca atg aca ctg gct cca ctg agt tct gtt tct gtc gtt gtg ggc      1286
Gln Thr Met Thr Leu Ala Pro Leu Ser Ser Val Ser Val Val Val Gly
            350                 355                 360 agt agt cct cgt tgatcagtat ctcattctct agattatcta gtattacggc          1338
Ser Ser Pro Arg
    365 tatggttact atatgatctc tctttttttgg tatgttctct taaactgcag ttgcacaatg   1398 ctctgatgtt ccattaaaaa aaaaaaaaaa aaa                                 1431

<210> SEQ ID NO 6
<211> LENGTH: 367
<212> TYPE: PRT
<213> ORGANISM: Nicotiana tabacum

<400> SEQUENCE: 6

Met Val Phe Pro Leu Asp Thr Gln Leu Leu Asn Pro Ile Phe Asp Val
1               5                   10                  15

Leu Tyr Cys Glu Glu Asp Arg Phe Leu Asp Asp Asp Leu Gly Glu
            20                  25                  30

Trp Ser Ser Thr Leu Glu Gln Val Gly Asn Asn Val Lys Lys Thr Leu
        35                  40                  45

Pro Leu Leu Glu Cys Asp Met Phe Trp Glu Asp Gln Leu Val Thr
    50                  55                  60

Leu Leu Thr Lys Glu Lys Glu Ser His Leu Gly Phe Asp Cys Leu Ile
65                  70                  75                  80

Ser Asp Gly Asp Gly Phe Leu Val Glu Val Arg Lys Glu Ala Leu Asp
                85                  90                  95

Trp Met Leu Arg Val Ile Ala His Tyr Gly Phe Thr Ala Met Thr Ala
            100                 105                 110

Val Leu Ala Val Asn Tyr Phe Asp Arg Phe Val Ser Gly Leu Cys Phe
        115                 120                 125

Gln Lys Asp Lys Pro Trp Met Ser Gln Leu Ala Ala Val Ala Cys Leu
    130                 135                 140

Ser Ile Ala Ala Lys Val Glu Glu Thr Gln Val Pro Leu Leu Leu Asp
145                 150                 155                 160

Leu Gln Val Ala Asp Ser Arg Phe Val Phe Glu Ala Lys Thr Ile Gln
                165                 170                 175

Arg Met Glu Leu Leu Val Leu Ser Thr Leu Lys Trp Lys Met Asn Pro
            180                 185                 190

Val Thr Pro Leu Ser Phe Ile Asp His Ile Met Arg Arg Phe Gly Phe
        195                 200                 205

Met Thr Asn Leu His Leu Asp Phe Leu Arg Arg Cys Glu Arg Leu Ile
    210                 215                 220

Leu Gly Ile Ile Thr Asp Ser Arg Leu Leu His Tyr Pro Pro Ser Val
225                 230                 235                 240

Ile Ala Thr Ala Val Val Tyr Phe Val Ile Asn Glu Ile Glu Pro Cys
                245                 250                 255

Asn Ala Met Glu Tyr Gln Asn Gln Leu Met Thr Val Leu Lys Val Lys
            260                 265                 270

Gln Asp Ser Phe Glu Glu Cys His Asp Leu Ile Leu Glu Leu Met Gly
        275                 280                 285

Thr Ser Gly Tyr Asn Ile Cys Gln Ser Leu Lys Arg Lys His Gln Ser
```

```
                290                 295                 300
Val Pro Gly Ser Pro Ser Gly Val Ile Asp Ala Tyr Phe Ser Cys Asp
305                 310                 315                 320

Ser Ser Asn Asp Ser Trp Ser Val Ala Ser Ile Ser Ser Pro
                325                 330                 335

Glu Pro Gln Tyr Lys Arg Ile Lys Thr Gln Asp Gln Thr Met Thr Leu
            340                 345                 350

Ala Pro Leu Ser Ser Val Ser Val Val Gly Ser Ser Pro Arg
            355                 360                 365

<210> SEQ ID NO 7
<211> LENGTH: 1788
<212> TYPE: DNA
<213> ORGANISM: Helianthus tuberosus
<220> FEATURE:
<221> NAME/KEY: CDS
<222> LOCATION: (165)..(1109)
<223> OTHER INFORMATION: cDNA encoding cyclin CYCD1;1

<400> SEQUENCE: 7
cacaacaatc acttctactc actattcact acttactaat cactgcaact tctccggcca      60
cttttcacct caaaccgccg gaactccgcc gctccggtcg acggtgaatc actgaatctt     120
agcaattatg ttcacaacag tatgaacaat caacaccggt catc atg tca atc tcg     176
                                                Met Ser Ile Ser
                                                  1
```

```
tgc tct gac tgc ttc tcc gac tta ctc tgc tgc gag gac tcc ggc ata      224
Cys Ser Asp Cys Phe Ser Asp Leu Leu Cys Cys Glu Asp Ser Gly Ile
  5                  10                  15                  20 tta tcc ggc gac gac cgg ccg gag tgc tcc tat gat ttc gaa tat tcc      272
Leu Ser Gly Asp Asp Arg Pro Glu Cys Ser Tyr Asp Phe Glu Tyr Ser
                 25                  30                  35 ggc gac ttt gat gat tcg atc gcg gag ttt ata gaa cag gag aga aag      320
Gly Asp Phe Asp Asp Ser Ile Ala Glu Phe Ile Glu Gln Glu Arg Lys
             40                  45                  50 ttc gtt cca gga atc gat tac gtc gag cga ttt caa tcg caa gtt ctc      368
Phe Val Pro Gly Ile Asp Tyr Val Glu Arg Phe Gln Ser Gln Val Leu
         55                  60                  65 gat gct tct gct aga gaa gaa tcg gtt gcc tgg atc ctt aag gtg caa      416
Asp Ala Ser Ala Arg Glu Glu Ser Val Ala Trp Ile Leu Lys Val Gln
     70                  75                  80 cgg ttt tac gga ttt cag ccg ttg acg gcg tac ctc tcc gtt aac tat      464
Arg Phe Tyr Gly Phe Gln Pro Leu Thr Ala Tyr Leu Ser Val Asn Tyr
 85                  90                  95                 100 ctg gat cgt ttc atc tat tgc cgt ggc ttc ccg gtg gca aat ggg tgg      512
Leu Asp Arg Phe Ile Tyr Cys Arg Gly Phe Pro Val Ala Asn Gly Trp
                105                 110                 115 ccc ttg caa ctc tta tct gta gca tgc ttg tct tta gct gct aaa atg      560
Pro Leu Gln Leu Leu Ser Val Ala Cys Leu Ser Leu Ala Ala Lys Met
            120                 125                 130 gag gaa acc ctt att cct tct att ctt gat ctc cag gtt gaa ggt gca      608
Glu Glu Thr Leu Ile Pro Ser Ile Leu Asp Leu Gln Val Glu Gly Ala
        135                 140                 145 aaa tat att ttc gag ccg aaa aca atc cga aga atg gag ttt ctt gtg     656
Lys Tyr Ile Phe Glu Pro Lys Thr Ile Arg Arg Met Glu Phe Leu Val
    150                 155                 160 ctt agt gtt ttg gat tgg aga cta aga tcc gtt aca ccg ttt agc ttt     704
Leu Ser Val Leu Asp Trp Arg Leu Arg Ser Val Thr Pro Phe Ser Phe
165                 170                 175                 180 atc ggc ttc ttt tcg cac aaa atc gat cca tct gga atg tat acg ggt     752
```

```
                                                                              -continued Ile Gly Phe Phe Ser His Lys Ile Asp Pro Ser Gly Met Tyr Thr Gly
                185                 190                 195 ttc ctt atc tca agg gca aca caa att atc ctc tca aat att caa gaa      800
Phe Leu Ile Ser Arg Ala Thr Gln Ile Ile Leu Ser Asn Ile Gln Glu
                200                 205                 210 gct agt tta ctt gag tat tgg cca tca tgt att gct gct gca aca ata      848
Ala Ser Leu Leu Glu Tyr Trp Pro Ser Cys Ile Ala Ala Ala Thr Ile
                215                 220                 225 ctt tgt gca gca agt gat ctt tct aaa ttc tca ctt atc aat gct gat      896
Leu Cys Ala Ala Ser Asp Leu Ser Lys Phe Ser Leu Ile Asn Ala Asp
            230                 235                 240 cat gct gaa tca tgg tgt gat ggc ctt agc aaa gag aag atc aca aaa      944
His Ala Glu Ser Trp Cys Asp Gly Leu Ser Lys Glu Lys Ile Thr Lys
245                 250                 255                 260 tgt tac aga ctt gta caa tct cca aag ata ttg ccg gta cat gtt cga      992
Cys Tyr Arg Leu Val Gln Ser Pro Lys Ile Leu Pro Val His Val Arg
                265                 270                 275 gtc atg acg gct cga gtg agt act gag tca ggt gac tca tcg tcg tcg     1040
Val Met Thr Ala Arg Val Ser Thr Glu Ser Gly Asp Ser Ser Ser Ser
                280                 285                 290 tct tct tcg cca tcg cct tac aaa aag agg aaa cta aat aac tac tca     1088
Ser Ser Ser Pro Ser Pro Tyr Lys Lys Arg Lys Leu Asn Asn Tyr Ser
            295                 300                 305 tgg ata gag gag gac aaa aga tgaaataag gagacaaaat aaataaataa         1139
Trp Ile Glu Glu Asp Lys Arg
        310             315 atccggattc tctctatat tttttaaagg aatcaacaaa tatatataaa aaaaaaaaat    1199
ggagtcagga aaagcaacga aagccgccgg aggaagaaaa ggcgccggag cgaggaagaa   1259
gtccgtcaca aagtccgtca aagccggtct ccagttcccc gtcggaagaa tcgctaggtt   1319
tctaaaaaaa ggccgatacg ctcaacgtac cggatccgga gctccgatct accttgctgc   1379
tgttctagaa taccttgctg ctgaggtttt ggagttggcg ggaaatgcag cgagagataa   1439
caagaagaca aggataaacc ctaggcactt gctattggct gttaggaacg atgaggaatt   1499
ggggaaattg cttgctggtg ttactattgc tagtggaggt gtgttgccca atatcaatcc   1559
ggttcttttg cccaagaagt cttccttctt ttctgctgct gagaagaccc ccaaatctaa   1619
aaagtcgcct aaaaaggctg cttagataga tgtttctggt tatagttggt tagattaagt   1679
tgaagcaaaa cagtctcttt tgttcaatta gtcgtctggc aatgtaacta ttttggtcgt   1739
cttcaaaatg ttaattggat actatcttct ttaaaaaaaa aaaaaaaaa               1788

<210> SEQ ID NO 8
<211> LENGTH: 315
<212> TYPE: PRT
<213> ORGANISM: Helianthus tuberosus

<400> SEQUENCE: 8

Met Ser Ile Ser Cys Ser Asp Cys Phe Ser Asp Leu Leu Cys Cys Glu
1               5                   10                  15

Asp Ser Gly Ile Leu Ser Gly Asp Asp Arg Pro Glu Cys Ser Tyr Asp
                20                  25                  30

Phe Glu Tyr Ser Gly Asp Phe Asp Asp Ser Ile Ala Glu Phe Ile Glu
            35                  40                  45

Gln Glu Arg Lys Phe Val Pro Gly Ile Asp Tyr Val Glu Arg Phe Gln
        50                  55                  60

Ser Gln Val Leu Asp Ala Ser Ala Arg Glu Glu Ser Val Ala Trp Ile
65                  70                  75                  80
```

```
Leu Lys Val Gln Arg Phe Tyr Gly Phe Gln Pro Leu Thr Ala Tyr Leu
                85                  90                  95

Ser Val Asn Tyr Leu Asp Arg Phe Ile Tyr Cys Arg Gly Phe Pro Val
            100                 105                 110

Ala Asn Gly Trp Pro Leu Gln Leu Leu Ser Val Ala Cys Leu Ser Leu
        115                 120                 125

Ala Ala Lys Met Glu Glu Thr Leu Ile Pro Ser Ile Leu Asp Leu Gln
130                 135                 140

Val Glu Gly Ala Lys Tyr Ile Phe Glu Pro Lys Thr Ile Arg Arg Met
145                 150                 155                 160

Glu Phe Leu Val Leu Ser Val Leu Asp Trp Arg Leu Arg Ser Val Thr
                165                 170                 175

Pro Phe Ser Phe Ile Gly Phe Ser His Lys Ile Asp Pro Ser Gly
            180                 185                 190

Met Tyr Thr Gly Phe Leu Ile Ser Arg Ala Thr Gln Ile Ile Leu Ser
            195                 200                 205

Asn Ile Gln Glu Ala Ser Leu Leu Glu Tyr Trp Pro Ser Cys Ile Ala
        210                 215                 220

Ala Ala Thr Ile Leu Cys Ala Ala Ser Asp Leu Ser Lys Phe Ser Leu
225                 230                 235                 240

Ile Asn Ala Asp His Ala Glu Ser Trp Cys Asp Gly Leu Ser Lys Glu
                245                 250                 255

Lys Ile Thr Lys Cys Tyr Arg Leu Val Gln Ser Pro Lys Ile Leu Pro
            260                 265                 270

Val His Val Arg Val Met Thr Ala Arg Val Ser Thr Glu Ser Gly Asp
        275                 280                 285

Ser Ser Ser Ser Ser Ser Pro Ser Pro Tyr Lys Lys Arg Lys Leu
290                 295                 300

Asn Asn Tyr Ser Trp Ile Glu Glu Asp Lys Arg
305                 310                 315

<210> SEQ ID NO 9
<211> LENGTH: 1414
<212> TYPE: DNA
<213> ORGANISM: Helianthus tuberosus
<220> FEATURE:
<221> NAME/KEY: CDS
<222> LOCATION: (48)..(1118)
<223> OTHER INFORMATION: cDNA encoding CYCD3;1

<400> SEQUENCE: 9
ttgaaccttc atttcttttc ttttcttctt tctaatcacc aacccca atg gcc att       56
                                                    Met Ala Ile
                                                      1 tta tca cca tat tca tct tct ttc tta gac aca ctc ttt tgc aat gaa      104
Leu Ser Pro Tyr Ser Ser Ser Phe Leu Asp Thr Leu Phe Cys Asn Glu
  5                  10                  15 caa caa gat cat gaa tat cat gaa tat gag tat gaa gat gaa ttt aca      152
Gln Gln Asp His Glu Tyr His Glu Tyr Glu Tyr Glu Asp Glu Phe Thr
 20                  25                  30                  35 caa acc acc ctc aca gat tca tct gat ctc cat ctt ccc ccc ctg gac      200
Gln Thr Thr Leu Thr Asp Ser Ser Asp Leu His Leu Pro Pro Leu Asp
                 40                  45                  50 caa cta gat ttg tca tgg gaa cat gaa gag ctt gtg tcc ttg ttc aca      248
Gln Leu Asp Leu Ser Trp Glu His Glu Glu Leu Val Ser Leu Phe Thr
             55                  60                  65 aaa gaa caa gag cag caa aaa caa acc cct tgt act ctc tct ttt ggc      296
```

```
                Lys Glu Gln Glu Gln Lys Gln Thr Pro Cys Thr Leu Ser Phe Gly
                             70                  75                  80 aaa act agt ccc tca gtt ttt gct gct cgt aaa gag gct gta gat tgg      344
Lys Thr Ser Pro Ser Val Phe Ala Ala Arg Lys Glu Ala Val Asp Trp
            85                  90                  95 atc ctt aag gtc aaa agt tgt tat gga ttc aca cct ctt aca gcc att      392
Ile Leu Lys Val Lys Ser Cys Tyr Gly Phe Thr Pro Leu Thr Ala Ile
100                 105                 110                 115 tta gcc atc aat tat ctt gat agg ttt ctt tct agc ctc cat ttt caa      440
Leu Ala Ile Asn Tyr Leu Asp Arg Phe Leu Ser Ser Leu His Phe Gln
                    120                 125                 130 gaa gat aaa cct tgg atg att caa ctt gtt gct gtt agt tgt ctc tct      488
Glu Asp Lys Pro Trp Met Ile Gln Leu Val Ala Val Ser Cys Leu Ser
                135                 140                 145 tta gct gct aaa gtt gaa gaa act caa gtg cca ctc cta cta gat ctt      536
Leu Ala Ala Lys Val Glu Glu Thr Gln Val Pro Leu Leu Leu Asp Leu
            150                 155                 160 caa gta gag gac act aag tac ttg ttt gag gct aaa aac ata caa aaa      584
Gln Val Glu Asp Thr Lys Tyr Leu Phe Glu Ala Lys Asn Ile Gln Lys
            165                 170                 175 atg gag ctt ttg gtg atg tca act ttg aaa tgg agg atg aac cca gtg      632
Met Glu Leu Leu Val Met Ser Thr Leu Lys Trp Arg Met Asn Pro Val
180                 185                 190                 195 aca cca atc tca ttt ctt gat cac att gta aga agg ctt gga tta act      680
Thr Pro Ile Ser Phe Leu Asp His Ile Val Arg Arg Leu Gly Leu Thr
                    200                 205                 210 gat cat gtt cat tgg gat ttt ttc aag aaa tgt gaa gct atg atc ctt      728
Asp His Val His Trp Asp Phe Phe Lys Lys Cys Glu Ala Met Ile Leu
                215                 220                 225 tgt tta gtt tca gat tca aga ttc gtg tgt tat aaa cca tcc gtg ttg      776
Cys Leu Val Ser Asp Ser Arg Phe Val Cys Tyr Lys Pro Ser Val Leu
            230                 235                 240 gcc aca gct aca atg ctt cac gtt gta gat gaa att gat cct ccc aat      824
Ala Thr Ala Thr Met Leu His Val Val Asp Glu Ile Asp Pro Pro Asn
245                 250                 255 tgt att gac tac aaa agt caa ctt ctg gat ctt ctc aaa acc act aag      872
Cys Ile Asp Tyr Lys Ser Gln Leu Leu Asp Leu Leu Lys Thr Thr Lys
260                 265                 270                 275 gac gac ata aac gag tgt tac gag ctc att gtc gag cta gct tac gat      920
Asp Asp Ile Asn Glu Cys Tyr Glu Leu Ile Val Glu Leu Ala Tyr Asp
                    280                 285                 290 cat cac aac aaa cga aaa cat gat gca aac gag aca aca acc aat ccg      968
His His Asn Lys Arg Lys His Asp Ala Asn Glu Thr Thr Thr Asn Pro
                295                 300                 305 gtt agt cca gct ggc gtg atc gat ttc act tgt gat gaa agt tca aat     1016
Val Ser Pro Ala Gly Val Ile Asp Phe Thr Cys Asp Glu Ser Ser Asn
            310                 315                 320 gag tca tgg gaa ctt aat gct cat cat ttc cgc gag cct tca ttc aag     1064
Glu Ser Trp Glu Leu Asn Ala His His Phe Arg Glu Pro Ser Phe Lys
325                 330                 335 aaa aca aga atg gat tca aca att cgg gtt cgg gtt tgg ttc act tat     1112
Lys Thr Arg Met Asp Ser Thr Ile Arg Val Arg Val Trp Phe Thr Tyr
340                 345                 350                 355 aag ctt taatcgaggg tagttgtaaa catgtaatcc gcatgcacgc tattaatcct      1168
Lys Leu acggtccact actacatata atcggcctat aaaattatag gttaagatga ccagtcgtag   1228
gcgtcgagat gtccttatgg ttggtcaatt tctctatggt tttaggtcgt ttttaatgtg   1288
agataaatta aattcggtat gttaagtctt tatcaagcaa tggacgttat atttattgtt   1348
```

```
tgatattgag aattaaattc catgggaaaa aaaaaaaaaa aaaaaaaaaa aaaaaaaaaa      1408
aaaaaa                                                                 1414
```

<210> SEQ ID NO 10
<211> LENGTH: 357
<212> TYPE: PRT
<213> ORGANISM: Helianthus tuberosus

<400> SEQUENCE: 10

```
Met Ala Ile Leu Ser Pro Tyr Ser Ser Phe Leu Asp Thr Leu Phe
1               5                   10                  15

Cys Asn Glu Gln Gln Asp His Glu Tyr His Glu Tyr Glu Tyr Glu Asp
                20                  25                  30

Glu Phe Thr Gln Thr Thr Leu Thr Asp Ser Ser Asp Leu His Leu Pro
            35                  40                  45

Pro Leu Asp Gln Leu Asp Leu Ser Trp Glu His Glu Leu Val Ser
50                  55                  60

Leu Phe Thr Lys Glu Gln Glu Gln Lys Gln Thr Pro Cys Thr Leu
65                  70                  75                  80

Ser Phe Gly Lys Thr Ser Pro Ser Val Phe Ala Ala Arg Lys Glu Ala
                85                  90                  95

Val Asp Trp Ile Leu Lys Val Lys Ser Cys Tyr Gly Phe Thr Pro Leu
            100                 105                 110

Thr Ala Ile Leu Ala Ile Asn Tyr Leu Asp Arg Phe Leu Ser Ser Leu
        115                 120                 125

His Phe Gln Glu Asp Lys Pro Trp Met Ile Gln Leu Val Ala Val Ser
130                 135                 140

Cys Leu Ser Leu Ala Ala Lys Val Glu Glu Thr Gln Val Pro Leu Leu
145                 150                 155                 160

Leu Asp Leu Gln Val Glu Asp Thr Lys Tyr Leu Phe Glu Ala Lys Asn
                165                 170                 175

Ile Gln Lys Met Glu Leu Leu Val Met Ser Thr Leu Lys Trp Arg Met
            180                 185                 190

Asn Pro Val Thr Pro Ile Ser Phe Leu Asp His Ile Val Arg Arg Leu
        195                 200                 205

Gly Leu Thr Asp His Val His Trp Asp Phe Phe Lys Lys Cys Glu Ala
210                 215                 220

Met Ile Leu Cys Leu Val Ser Asp Ser Arg Phe Val Cys Tyr Lys Pro
225                 230                 235                 240

Ser Val Leu Ala Thr Ala Thr Met Leu His Val Val Asp Glu Ile Asp
                245                 250                 255

Pro Pro Asn Cys Ile Asp Tyr Lys Ser Gln Leu Leu Asp Leu Leu Lys
            260                 265                 270

Thr Thr Lys Asp Asp Ile Asn Glu Cys Tyr Glu Leu Ile Val Glu Leu
        275                 280                 285

Ala Tyr Asp His His Asn Lys Arg Lys His Asp Ala Asn Glu Thr Thr
290                 295                 300

Thr Asn Pro Val Ser Pro Ala Gly Val Ile Asp Phe Thr Cys Asp Glu
305                 310                 315                 320

Ser Ser Asn Glu Ser Trp Glu Leu Asn Ala His His Phe Arg Glu Pro
                325                 330                 335

Ser Phe Lys Lys Thr Arg Met Asp Ser Thr Ile Arg Val Arg Val Trp
            340                 345                 350
```

Phe Thr Tyr Lys Leu
            355

<210> SEQ ID NO 11
<211> LENGTH: 100
<212> TYPE: DNA
<213> ORGANISM: Artificial Sequence
<220> FEATURE:
<223> OTHER INFORMATION: T-DNA of pGSV5

<400> SEQUENCE: 11
aattacaacg gtatatatcc tgccagtact cggccgtcga ccgcggtacc cggggaagct    60
tagatccatg gagccattta caattgaata tatcctgccg                          100

<210> SEQ ID NO 12
<211> LENGTH: 17
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D1 type
      cyclin.

<400> SEQUENCE: 12
gcmtggatyc tyaaggt                                                   17

<210> SEQ ID NO 13
<211> LENGTH: 17
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D1 type
      cyclin.

<400> SEQUENCE: 13
tgcttgtcwt tagctgc                                                   17

<210> SEQ ID NO 14
<211> LENGTH: 18
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D1 type
      cyclin.

<400> SEQUENCE: 14
aagaatggar yttcttgt                                                  18

<210> SEQ ID NO 15
<211> LENGTH: 19
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D1 type
      cyclin.
<221> NAME/KEY: misc_feature
<222> LOCATION: (5)..(5)
<223> OTHER INFORMATION: n is any nucleotide (A, T, C, G)

<400> SEQUENCE: 15
aragnatycy kgcwgcagc                                                 19

<210> SEQ ID NO 16
<211> LENGTH: 19
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D1 type
      cyclin.
<221> NAME/KEY: misc_feature
<222> LOCATION: (14)..(14)
<223> OTHER INFORMATION: n is any nucleotide (A, T, C, G)

<400> SEQUENCE: 16
ccrtcacacc awgnytcag                                                19

<210> SEQ ID NO 17
<211> LENGTH: 16
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D2 type
      cyclin.

<400> SEQUENCE: 17
tggwgatttg gatttg                                                   16

<210> SEQ ID NO 18
<211> LENGTH: 17
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D2 type
      cyclin.
<221> NAME/KEY: misc_feature
<222> LOCATION: (3)..(3)
<223> OTHER INFORMATION: n is any nucleotide (A, T, C, G)
<221> NAME/KEY: misc_feature
<222> LOCATION: (6)..(6)
<223> OTHER INFORMATION: n is any nucleotide (A, T, C, G)

<400> SEQUENCE: 18
atnaantact tggatcg                                                  17

<210> SEQ ID NO 19
<211> LENGTH: 19
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D2 type
      cyclin.
<221> NAME/KEY: misc_feature
<222> LOCATION: (9)..(9)
<223> OTHER INFORMATION: n is any nucleotide (A, T, C, G)
<221> NAME/KEY: misc_feature
<222> LOCATION: (16)..(16)
<223> OTHER INFORMATION: n is any nucleotide (A, T, C, G)

<400> SEQUENCE: 19
agcttgcant ctccanttc                                                19

<210> SEQ ID NO 20
<211> LENGTH: 17

```
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D2 type
      cyclin.
<221> NAME/KEY: misc_feature
<222> LOCATION: (8)..(8)
<223> OTHER INFORMATION: n is any nucleotide (A, T, C, G)
<221> NAME/KEY: misc_feature
<222> LOCATION: (15)..(15)
<223> OTHER INFORMATION: n is any nucleotide (A, T, C, G)

<400> SEQUENCE: 20
tcagaagncc tgaantc                                                      17

<210> SEQ ID NO 21
<211> LENGTH: 17
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D3 type
      cyclin.
<221> NAME/KEY: misc_feature
<222> LOCATION: (3)..(3)
<223> OTHER INFORMATION: n is any nucleotide (A, T, C, G)
<221> NAME/KEY: misc_feature
<222> LOCATION: (9)..(9)
<223> OTHER INFORMATION: n is any nucleotide (A, T, C, G)
<221> NAME/KEY: misc_feature
<222> LOCATION: (12)..(12)
<223> OTHER INFORMATION: n is any nucleotide (A, T, C, G)

<400> SEQUENCE: 21
gantggatny tnaargt                                                      17

<210> SEQ ID NO 22
<211> LENGTH: 17
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D3 type
      cyclin.

<400> SEQUENCE: 22
aagabaarcc wtggatg                                                      17

<210> SEQ ID NO 23
<211> LENGTH: 20
<212> TYPE: DNA
<213> ORGANISM: Artificial Sequence
<220> FEATURE:
<223> OTHER INFORMATION: synthetic degenerate oligonucleotide
      corresponding to the sequences encoding conserved amino acid
      sequences within the cyclin box for PCR amplification of a D3 type
      cyclin.

<400> SEQUENCE: 23
gtkgaagara ctcaagtbcc                                                   20

<210> SEQ ID NO 24
<211> LENGTH: 24
<212> TYPE: DNA
<213> ORGANISM: Artificial Sequence
<220> FEATURE:
<223> OTHER INFORMATION: synthetic degenerate oligonucleotide
``` corresponding to the sequences encoding conserved amino acid
sequences within the cyclin box for PCR amplification of a D3 type
cyclin.
<221> NAME/KEY: misc_feature
<222> LOCATION: (4)..(4)
<223> OTHER INFORMATION: n is any nucleotide (A, T, C, G)
<221> NAME/KEY: misc_feature
<222> LOCATION: (7)..(7)
<223> OTHER INFORMATION: n is any nucleotide (A, T, C, G)
<221> NAME/KEY: misc_feature
<222> LOCATION: (13)..(13)
<223> OTHER INFORMATION: n is any nucleotide (A, T, C, G)

<400> SEQUENCE: 24
tggngtnacw ggntkcatyy tcca                                          24

<210> SEQ ID NO 25
<211> LENGTH: 20
<212> TYPE: DNA
<213> ORGANISM: Artificial Sequence
<220> FEATURE:
<223> OTHER INFORMATION: synthetic degenerate oligonucleotide
corresponding to the sequences encoding conserved amino acid
sequences within the cyclin box for PCR amplification of a D3 type
cyclin.
<221> NAME/KEY: misc_feature
<222> LOCATION: (1)..(20)
<223> OTHER INFORMATION: n is any nucleotide (A, T, C, G)

<400> SEQUENCE: 25 gcwgnnngcna nnncagangg                                              20

<210> SEQ ID NO 26
<211> LENGTH: 1846
<212> TYPE: DNA
<213> ORGANISM: Zea mays

<400> SEQUENCE: 26
ctgcagtggc ctagccggcg tcgtcctccc cctctchcgc tcctctgtcc tccctctcc     60 acttgagaag aacacaatta ggaaaaaaag gcaaaaaaca tttaccttttt ttctatctgt  120 atattatctg aataaatcaa gaggaggaag aggggaggga gcgagggagg gggaggagta   180
gcaaatccag actccatagc aaccagctcg cgagaagggg aaaaggggga ggaagagctt   240
cgcttgtgta ttgattgctc gctgctccag tccctgcatt cgtgccgttt ttggcaagta   300
ggtggcgtgg caagcatggt gccgggctat gactgcgccg cctccgtgct gctgtgcgcg   360
gaggacaacg ctgctattct cggcctggac gacgatgggg aggagtcctc ctgggcggcc   420
gccgctacgc cgccacgtga caccgtcgcc gccgccgccg ccaccggggt cgccgtcgat   480
gggattttga cggagttccc cttgctctcg gatgactgcg ttgcgacgct cgtggagaag   540
gaggtggagc acatgcccgc ggaggggtac ctccagaagc tgcagcgacg gcatggggac   600
ctggatttgg ccgccgtcag gaaggacgcc atcgattgga tttggaaggt cattgagcat   660
tacaatttcg caccgttgac tgccgttttg tctgtgaact acctcgatag attcctctcc   720
acgtatgagt tccctgaagg cagagcttgg atgactcagc tcttggcagt ggcttgcttg   780
tctttggctt cgaaaatcga agagactttt gtgccactcc ccttggattt gcaggtagcg   840
gaggcaaagt ttgtttttga gggaaggacc ataaaaagga tggagcttct ggtgctaagc   900
accttaaagt ggaggatgca tgctgttact gcttgctcat tgttgaata ctttcttcat   960 aaattgagtg atcatggtgc accctccttg cttgcacgct ctcgctcttc ggaccttgtc  1020
ttgagcaccg ctaaaggtgc tgaattcgtg gtattcagac cctccgagat tgctgccagt  1080

-continued

```
gttgcacttg ctgctatcgg cgaatgcagg agttctgtaa ttgagagagc tgctagtagc     1140
tgcaaatatt tggacaagga gagggtttta agatgccatg aaatgattca agagaagatt     1200
actgcgggaa gcattgtcct aaagtctgct ggatcatcaa tctcctctgt gccacaaagc     1260
ccaataggtg tcctggacgc tgcagcctgt ctgagtcaac aaagcgatga cgctactgtc     1320
gggtctcctg cagtatgtta ccatagttct tccacaagca agaggagaag gatcactaga     1380
cgtctactct aattgtggta cgcttcaggt gtgctcctca ccgctctagg agttttgat      1440 tggttcaaac atcttaaatt tagttttggcc gctggaggat tatggtttag tcaagtagtt     1500
gctgaatgga caacaaaaca cgcacactac ttggtccata agacaagaa ataactggc      1560 agcgtcccgc gagccagcgc tgcaatccag ttcatgcaag accctagagt ccagggggggg     1620 tgctggtgta ggtagagagg gaacaaggca ttcacatacg ccgtagagat gagagagcct     1680
ctcgtatgtt ttgtactttt gctccttcag tttgcaatga actatataaa caaggattgc     1740 cttgggcag tgaacatttg tcggatgaaa agaatcaaaa aggatggggg tcggcagagg     1800
aatagaacaa tttgatatat ttccataaac taaaaaaaaa aaaaaa                     1846
```

<210> SEQ ID NO 27
<211> LENGTH: 1951
<212> TYPE: DNA
<213> ORGANISM: Arabidopsis thaliana
<220> FEATURE:
<221> NAME/KEY: CDS
<222> LOCATION: (104)..(1111)
<223> OTHER INFORMATION: product = cyclin delta

<400> SEQUENCE: 27

```
caaaattcaa aaacctcaca tttcacttct ctcttctcgc ttcttctaga tctcaccggt      60
ttatctagct ccggtttgat tcatctccgg ttatggggag aga atg agg agt tac       115
                                              Met Arg Ser Tyr
                                               1 cgt ttt agt gat tat cta cac atg tct gtt tca ttc tct aac gat atg      163
Arg Phe Ser Asp Tyr Leu His Met Ser Val Ser Phe Ser Asn Asp Met
  5               10                  15                  20 gat ttg ttt tgt gga gaa gac tcc ggt gtg ttt tcc ggt gag tca acg      211
Asp Leu Phe Cys Gly Glu Asp Ser Gly Val Phe Ser Gly Glu Ser Thr
             25                  30                  35 gtt gat ttc tcg tct tcc gag gtt gat tca tgg cct ggt gat tct atc      259
Val Asp Phe Ser Ser Ser Glu Val Asp Ser Trp Pro Gly Asp Ser Ile
         40                  45                  50 gct tgt ttt atc gaa gac gag cgt cac ttc gtt cct gga cat gat tat      307
Ala Cys Phe Ile Glu Asp Glu Arg His Phe Val Pro Gly His Asp Tyr
     55                  60                  65 ctc tct aga ttt caa act cga tct ctc gat gct tcc gct aga gaa gat      355
Leu Ser Arg Phe Gln Thr Arg Ser Leu Asp Ala Ser Ala Arg Glu Asp
 70                  75                  80 tcc gtc gca tgg att ctc aag gta caa gcg tat tat aac ttt cag cct      403
Ser Val Ala Trp Ile Leu Lys Val Gln Ala Tyr Tyr Asn Phe Gln Pro
 85                  90                  95                 100 tta acg gcg tac ctc gcc gtt aac tat atg gat cgg ttt ctt tac gct      451
Leu Thr Ala Tyr Leu Ala Val Asn Tyr Met Asp Arg Phe Leu Tyr Ala
                105                 110                 115 cgt cga tta ccg gaa acg agt ggt tgg cca atg caa ctt tta gca gtg      499
Arg Arg Leu Pro Glu Thr Ser Gly Trp Pro Met Gln Leu Leu Ala Val
            120                 125                 130 gca tgc ttg tct tta gct gca aag atg gag gaa att ctc gtt cct tct      547
Ala Cys Leu Ser Leu Ala Ala Lys Met Glu Glu Ile Leu Val Pro Ser
        135                 140                 145
```

```
ctt ttt gat ttt cag gtt gca gga gtg aag tat tta ttt gaa gca aaa        595
Leu Phe Asp Phe Gln Val Ala Gly Val Lys Tyr Leu Phe Glu Ala Lys
    150                 155                 160 act ata aaa aga atg gaa ctt ctt gtt cta agt gtg tta gat tgg aga        643
Thr Ile Lys Arg Met Glu Leu Leu Val Leu Ser Val Leu Asp Trp Arg
165                 170                 175                 180 cta aga tcg gtt aca ccg ttt gat ttc att agc ttc ttt gct tac aag        691
Leu Arg Ser Val Thr Pro Phe Asp Phe Ile Ser Phe Phe Ala Tyr Lys
                185                 190                 195 atc gat cct tcg ggt acc ttt ctc ggg ttc ttt atc tcc cat gct aca        739
Ile Asp Pro Ser Gly Thr Phe Leu Gly Phe Phe Ile Ser His Ala Thr
        200                 205                 210 gag att ata ctc tcc aac ata aaa gaa gcg agc ttt ctt gag tac tgg        787
Glu Ile Ile Leu Ser Asn Ile Lys Glu Ala Ser Phe Leu Glu Tyr Trp
            215                 220                 225 cca tcg agt ata gct gca gcc gcg att ctc tgt gta gcg aac gag tta        835
Pro Ser Ser Ile Ala Ala Ala Ala Ile Leu Cys Val Ala Asn Glu Leu
                230                 235                 240 cct tct cta tcc tct gtt gtc aat ccc cac gag agc cct gag act tgg        883
Pro Ser Leu Ser Ser Val Val Asn Pro His Glu Ser Pro Glu Thr Trp
245                 250                 255                 260 tgt gac gga ttg agc aaa gag aag ata gtg aga tgc tat aga ctg atg        931
Cys Asp Gly Leu Ser Lys Glu Lys Ile Val Arg Cys Tyr Arg Leu Met
                265                 270                 275 aaa gcg atg gcc atc gag aat aac cgg tta aat aca cca aaa gtg ata        979
Lys Ala Met Ala Ile Glu Asn Asn Arg Leu Asn Thr Pro Lys Val Ile
            280                 285                 290 gca aag ctt cga gtg agt gta agg gca tca tcg acg tta aca agg cca       1027
Ala Lys Leu Arg Val Ser Val Arg Ala Ser Ser Thr Leu Thr Arg Pro
                295                 300                 305 agt gat gaa tcc tct tct cct tgt aaa agg aga aaa tta agt ggc tat       1075
Ser Asp Glu Ser Ser Ser Pro Cys Lys Arg Arg Lys Leu Ser Gly Tyr
310                 315                 320 tca tgg gta ggt gat gaa aca tct acc tct aat taa aatttgggga            1121
Ser Trp Val Gly Asp Glu Thr Ser Thr Ser Asn
325                 330                 335 gtgaaagtag aggaccaagg aaacaaaacc tagaagaaaa aaaaccctct tctgtttaag      1181
tagagtatat ttttaacaa gtacatagta ataagggagt gatgaagaaa agtaaaagtg       1241
tttattggct gagttaaagt aattaagagt tttccaacca aggggaagga ataagagttt      1301
tggttacaat tactttatg gaaagggtaa aaattgggtt ttggggttgg ttggttggtt       1361
gggagagacg aagctcacat taatggcttt gcagattccc aagaaagcaa aatgagtaag      1421
tgagtgtaac acacacgtgt tagagaaaag atatgatcat gtgagtgtgt gtgtgtgaga      1481
gagagagaga agagtatttg cattagagtc ctcatcacac aggtactgat ggataagaca      1541
ggggagcgtc tgcaaaagat tgtgagtgg agatttttct gagctctttg tcttaatgga       1601
tcgcagcagt tcatgggacc cttcctcagc ttcatcatca aacaaaaaaa aaatcaagtt      1661
gcgaagtata tataatttgt tttttgtttg gattttttaag attttttgatt ccttgtgtgt   1721 gacttcacgt gacggaggcg tgtgtctcac gtgtttgttt tctcttcaaa tcttttattt     1781
tggcgggaaa ttttttgtgtt tttgattttct atacgtattc gtggactcca aatgagtttt   1841
gtcacggtgc gttttagtaa cgtatgcatg cgtgtaaggt gtcacgtatg tgtatatata     1901 tgatttttttt tttggattct tgaaaggtta aatttttatat ataaaacgtt              1951

<210> SEQ ID NO 28
```

<211> LENGTH: 335
<212> TYPE: PRT
<213> ORGANISM: Arabidopsis thaliana

<400> SEQUENCE: 28

| | | | | | | | | | | | | | | | |
|---|---|---|---|---|---|---|---|---|---|---|---|---|---|---|---|
| Met | Arg | Ser | Tyr | Arg | Phe | Ser | Asp | Tyr | Leu | His | Met | Ser | Val | Ser | Phe |
| 1 | | | | 5 | | | | | 10 | | | | | 15 | |
| Ser | Asn | Asp | Met | Asp | Leu | Phe | Cys | Gly | Glu | Asp | Ser | Gly | Val | Phe | Ser |
| | | | 20 | | | | | 25 | | | | | 30 | | |
| Gly | Glu | Ser | Thr | Val | Asp | Phe | Ser | Ser | Glu | Val | Asp | Ser | Trp | Pro | |
| | | 35 | | | | | 40 | | | | | 45 | | | |
| Gly | Asp | Ser | Ile | Ala | Cys | Phe | Ile | Glu | Asp | Glu | Arg | His | Phe | Val | Pro |
| | 50 | | | | | 55 | | | | | 60 | | | | |
| Gly | His | Asp | Tyr | Leu | Ser | Arg | Phe | Gln | Thr | Arg | Ser | Leu | Asp | Ala | Ser |
| 65 | | | | | 70 | | | | | 75 | | | | | 80 |
| Ala | Arg | Glu | Asp | Ser | Val | Ala | Trp | Ile | Leu | Lys | Val | Gln | Ala | Tyr | Tyr |
| | | | | 85 | | | | | 90 | | | | | 95 | |
| Asn | Phe | Gln | Pro | Leu | Thr | Ala | Tyr | Leu | Ala | Val | Asn | Tyr | Met | Asp | Arg |
| | | | 100 | | | | | 105 | | | | | 110 | | |
| Phe | Leu | Tyr | Ala | Arg | Arg | Leu | Pro | Glu | Thr | Ser | Gly | Trp | Pro | Met | Gln |
| | | 115 | | | | | 120 | | | | | 125 | | | |
| Leu | Leu | Ala | Val | Ala | Cys | Leu | Ser | Leu | Ala | Ala | Lys | Met | Glu | Glu | Ile |
| | 130 | | | | | 135 | | | | | 140 | | | | |
| Leu | Val | Pro | Ser | Leu | Phe | Asp | Phe | Gln | Val | Ala | Gly | Val | Lys | Tyr | Leu |
| 145 | | | | | 150 | | | | | 155 | | | | | 160 |
| Phe | Glu | Ala | Lys | Thr | Ile | Lys | Arg | Met | Glu | Leu | Leu | Val | Leu | Ser | Val |
| | | | | 165 | | | | | 170 | | | | | 175 | |
| Leu | Asp | Trp | Arg | Leu | Arg | Ser | Val | Thr | Pro | Phe | Asp | Phe | Ile | Ser | Phe |
| | | | 180 | | | | | 185 | | | | | 190 | | |
| Phe | Ala | Tyr | Lys | Ile | Asp | Pro | Ser | Gly | Thr | Phe | Leu | Gly | Phe | Phe | Ile |
| | | 195 | | | | | 200 | | | | | 205 | | | |
| Ser | His | Ala | Thr | Glu | Ile | Ile | Leu | Ser | Asn | Ile | Lys | Glu | Ala | Ser | Phe |
| | 210 | | | | | 215 | | | | | 220 | | | | |
| Leu | Glu | Tyr | Trp | Pro | Ser | Ser | Ile | Ala | Ala | Ala | Ile | Leu | Cys | Val | |
| 225 | | | | | 230 | | | | | 235 | | | | | 240 |
| Ala | Asn | Glu | Leu | Pro | Ser | Leu | Ser | Ser | Val | Val | Asn | Pro | His | Glu | Ser |
| | | | | 245 | | | | | 250 | | | | | 255 | |
| Pro | Glu | Thr | Trp | Cys | Asp | Gly | Leu | Ser | Lys | Glu | Lys | Ile | Val | Arg | Cys |
| | | | 260 | | | | | 265 | | | | | 270 | | |
| Tyr | Arg | Leu | Met | Lys | Ala | Met | Ala | Ile | Glu | Asn | Asn | Arg | Leu | Asn | Thr |
| | | 275 | | | | | 280 | | | | | 285 | | | |
| Pro | Lys | Val | Ile | Ala | Lys | Leu | Arg | Val | Ser | Val | Arg | Ala | Ser | Ser | Thr |
| | 290 | | | | | 295 | | | | | 300 | | | | |
| Leu | Thr | Arg | Pro | Ser | Asp | Glu | Ser | Ser | Pro | Cys | Lys | Arg | Arg | Lys | |
| 305 | | | | | 310 | | | | | 315 | | | | | 320 |
| Leu | Ser | Gly | Tyr | Ser | Trp | Val | Gly | Asp | Glu | Thr | Ser | Thr | Ser | Asn | |
| | | | | 325 | | | | | 330 | | | | | 335 | |

<210> SEQ ID NO 29
<211> LENGTH: 1650
<212> TYPE: DNA
<213> ORGANISM: Arabidopsis thaliana
<220> FEATURE:
<221> NAME/KEY: CDS
<222> LOCATION: (195)..(1280)
<223> OTHER INFORMATION: product = cyclin delta2

-continued

```
<400> SEQUENCE: 29
cttctcctct gccatgaaaa tcgcagttcc tcaagacaaa acctcctcag aaatctccca       60
tctttgatga cttttgcttc cttagttttc actttcttgt ccgaacgctc tcaaaaactt      120
tgagaccacc ccaataaacg aattaaacag actattatca atcaatacac aacacaacaa      180
tcaaaccaaa cccc atg gct gag aat ctt gct tgt ggt gaa acc agc gag        230
              Met Ala Glu Asn Leu Ala Cys Gly Glu Thr Ser Glu
                1               5                   10 tca tgg atc att gac aac gac gat gat atc aac tat ggc ggc gga            278
Ser Trp Ile Ile Asp Asn Asp Asp Asp Ile Asn Tyr Gly Gly Gly
         15                  20                  25 ttt acg aac gag att gat tac aat cac caa ctt ttt gct aaa gac gac        326
Phe Thr Asn Glu Ile Asp Tyr Asn His Gln Leu Phe Ala Lys Asp Asp
     30                  35                  40 aac ttt ggc ggc aac gga tca att ccg atg atg ggt tct tct tca tcg        374
Asn Phe Gly Gly Asn Gly Ser Ile Pro Met Met Gly Ser Ser Ser Ser
45                  50                  55                  60 tcc ttg agt gaa gac aga atc aaa gag atg ttg gtg aga gag att gag        422
Ser Leu Ser Glu Asp Arg Ile Lys Glu Met Leu Val Arg Glu Ile Glu
                 65                  70                  75 ttt tgc cct gga act gat tat gtt aag aga ttg ctt tct ggt gat ttg        470
Phe Cys Pro Gly Thr Asp Tyr Val Lys Arg Leu Leu Ser Gly Asp Leu
             80                  85                  90 gat ttg tct gtt cga aac caa gct ctt gat tgg att cta aag gtt tgt        518
Asp Leu Ser Val Arg Asn Gln Ala Leu Asp Trp Ile Leu Lys Val Cys
         95                 100                 105 gct cat tac cat ttt gga cat ctg tgc ata tgc cta tcc atg aac tac        566
Ala His Tyr His Phe Gly His Leu Cys Ile Cys Leu Ser Met Asn Tyr
     110                 115                 120 ttg gat cgg ttc tta aca tcc tat gaa ttg ccg aaa gac aag gat tgg        614
Leu Asp Arg Phe Leu Thr Ser Tyr Glu Leu Pro Lys Asp Lys Asp Trp
125                 130                 135                 140 gct gct cag tta cta gct gtg tct tgc tta tca tta gca tcc aaa atg        662
Ala Ala Gln Leu Leu Ala Val Ser Cys Leu Ser Leu Ala Ser Lys Met
                145                 150                 155 gaa gaa act gat gtg cct cac att gtt gat tta cag gtg gaa gat ccc        710
Glu Glu Thr Asp Val Pro His Ile Val Asp Leu Gln Val Glu Asp Pro
            160                 165                 170 aag ttt gtt ttt gag gcc aaa aca ata aaa agg atg gag ctt ttg gtt        758
Lys Phe Val Phe Glu Ala Lys Thr Ile Lys Arg Met Glu Leu Leu Val
        175                 180                 185 gtc acc act ttg aat tgg aga ttg caa gct cta act cca ttc tcc ttc        806
Val Thr Thr Leu Asn Trp Arg Leu Gln Ala Leu Thr Pro Phe Ser Phe
    190                 195                 200 att gat tat ttc gtt gac aag atc agt ggt cac gtg tcg gag aat ttg        854
Ile Asp Tyr Phe Val Asp Lys Ile Ser Gly His Val Ser Glu Asn Leu
205                 210                 215                 220 atc tat aga tcg tca aga ttc atc tta aac acc acc aaa gca att gaa        902
Ile Tyr Arg Ser Ser Arg Phe Ile Leu Asn Thr Thr Lys Ala Ile Glu
                225                 230                 235 ttc tta gac ttc agg cct tct gag ata gct gca gct gct gca gtg tct        950
Phe Leu Asp Phe Arg Pro Ser Glu Ile Ala Ala Ala Ala Ala Val Ser
            240                 245                 250 gtt tcc att tca gga gaa aca gaa tgc att gat gag gaa aag gca ctg        998
Val Ser Ile Ser Gly Glu Thr Glu Cys Ile Asp Glu Glu Lys Ala Leu
        255                 260                 265 tct agt ctc ata tat gta aaa cag gag agg gtg aag aga tgt ttg aat       1046
Ser Ser Leu Ile Tyr Val Lys Gln Glu Arg Val Lys Arg Cys Leu Asn
    270                 275                 280
```

-continued

```
ctg atg aga agt ctc act ggg gag gag aat gtg cgg gga act agt tta    1094
Leu Met Arg Ser Leu Thr Gly Glu Glu Asn Val Arg Gly Thr Ser Leu
285                 290                 295                 300 tcg cag gag cag gcg cga gtt gcg gta aga gct gta cct gca agt cca    1142
Ser Gln Glu Gln Ala Arg Val Ala Val Arg Ala Val Pro Ala Ser Pro
                305                 310                 315 gtt gga gtg ttg gaa gca aca tgt ttg agc tat agg agt gaa gag aga    1190
Val Gly Val Leu Glu Ala Thr Cys Leu Ser Tyr Arg Ser Glu Glu Arg
            320                 325                 330 aca gtt gag tca tgt aca aat tcc tca cag agt agt cca gac aac aac    1238
Thr Val Glu Ser Cys Thr Asn Ser Ser Gln Ser Ser Pro Asp Asn Asn
        335                 340                 345 aac aac aac aac aac agc aac aag agg agg aga aaa caa tga             1280
Asn Asn Asn Asn Asn Ser Asn Lys Arg Arg Arg Lys Gln
    350                 355                 360 gagagaataa aagagtcata cattgctttt tacaacccaa aaccacaagt actcatgaca   1340
tttgaggttc ttatttattt ttttggtttt ttttttctac ataaattttc tttttctttc   1400
tttgatttct cattttcaat ctgaaaattg gattgaatat gagagttttg tgagaaagga   1460
aaaaagaaaa taagagagag agagagagct ctttggaagg cgggcaaaat taataagtca   1520
ttattgatga tgatgagaga catccctgtt cttgctccaa gggactttt ttttctaca    1580
taatgtcaga gatataatta aaaaaaaaag aaatagaaag agaattaatt ttatgaaaaa   1640
aaaaaaaaaa                                                         1650
```

<210> SEQ ID NO 30
<211> LENGTH: 361
<212> TYPE: PRT
<213> ORGANISM: Arabidopsis thaliana

<400> SEQUENCE: 30

```
Met Ala Glu Asn Leu Ala Cys Gly Glu Thr Ser Glu Ser Trp Ile Ile
1               5                   10                  15

Asp Asn Asp Asp Asp Asp Ile Asn Tyr Gly Gly Gly Phe Thr Asn Glu
                20                  25                  30

Ile Asp Tyr Asn His Gln Leu Phe Ala Lys Asp Asp Asn Phe Gly Gly
            35                  40                  45

Asn Gly Ser Ile Pro Met Met Gly Ser Ser Ser Ser Leu Ser Glu
        50                  55                  60

Asp Arg Ile Lys Glu Met Leu Val Arg Glu Ile Glu Phe Cys Pro Gly
65                  70                  75                  80

Thr Asp Tyr Val Lys Arg Leu Leu Ser Gly Asp Leu Asp Leu Ser Val
                85                  90                  95

Arg Asn Gln Ala Leu Asp Trp Ile Leu Lys Val Cys Ala His Tyr His
                100                 105                 110

Phe Gly His Leu Cys Ile Cys Leu Ser Met Asn Tyr Leu Asp Arg Phe
            115                 120                 125

Leu Thr Ser Tyr Glu Leu Pro Lys Asp Lys Asp Trp Ala Ala Gln Leu
        130                 135                 140

Leu Ala Val Ser Cys Leu Ser Leu Ala Ser Lys Met Glu Glu Thr Asp
145                 150                 155                 160

Val Pro His Ile Val Asp Leu Gln Val Glu Asp Pro Lys Phe Val Phe
                165                 170                 175

Glu Ala Lys Thr Ile Lys Arg Met Glu Leu Leu Val Val Thr Thr Leu
            180                 185                 190
```

-continued

```
Asn Trp Arg Leu Gln Ala Leu Thr Pro Phe Ser Phe Ile Asp Tyr Phe
        195                 200                 205

Val Asp Lys Ile Ser Gly His Val Ser Glu Asn Leu Ile Tyr Arg Ser
    210                 215                 220

Ser Arg Phe Ile Leu Asn Thr Thr Lys Ala Ile Glu Phe Leu Asp Phe
225                 230                 235                 240

Arg Pro Ser Glu Ile Ala Ala Ala Ala Val Ser Val Ser Ile Ser
                245                 250                 255

Gly Glu Thr Glu Cys Ile Asp Glu Lys Ala Leu Ser Ser Leu Ile
                260                 265                 270

Tyr Val Lys Gln Glu Arg Val Lys Arg Cys Leu Asn Leu Met Arg Ser
        275                 280                 285

Leu Thr Gly Glu Glu Asn Val Arg Gly Thr Ser Leu Ser Gln Glu Gln
        290                 295                 300

Ala Arg Val Ala Val Arg Ala Val Pro Ala Ser Pro Val Gly Val Leu
305                 310                 315                 320

Glu Ala Thr Cys Leu Ser Tyr Arg Ser Glu Glu Arg Thr Val Glu Ser
                325                 330                 335

Cys Thr Asn Ser Ser Gln Ser Ser Pro Asp Asn Asn Asn Asn Asn
                340                 345                 350

Asn Ser Asn Lys Arg Arg Lys Gln
        355                 360

<210> SEQ ID NO 31
<211> LENGTH: 1632
<212> TYPE: DNA
<213> ORGANISM: Arabidopsis thaliana
<220> FEATURE:
<221> NAME/KEY: CDS
<222> LOCATION: (266)..(1396)
<223> OTHER INFORMATION: product = cyclin delta3

<400> SEQUENCE: 31
atcactctcc gaaacccact tccagctttt tcctctctct ttctctctct agtctctctt      60
ttgtagctct cccctgctaa gcctaaccac tgcacgtttc catagagagg aaagatgagt    120
ctctctccga gagattttct ctctatcatc ttatcttctt ccgtgtaatg ctctgagcca    180
aaacccaata actaaatcaa caacaatata gaagagaaga gaaagatctt atctttcttc    240
tcattcttga gtttagtccc ccaca atg gcg att cgg aag gag gaa gaa agt     292
                              Met Ala Ile Arg Lys Glu Glu Glu Ser
                                1               5 aga gaa gaa cag agc aat tcg ttt ctt ctt gat gct ctc tac tgc gaa     340
Arg Glu Glu Gln Ser Asn Ser Phe Leu Leu Asp Ala Leu Tyr Cys Glu
10                  15                  20                  25 gaa gag aaa tgg gac gat gaa gga gaa gaa gtt gaa gaa aac tct tcc     388
Glu Glu Lys Trp Asp Asp Glu Gly Glu Glu Val Glu Glu Asn Ser Ser
                30                  35                  40 ttg tct tct tct tct tct cca ttc gtt gtt ttg caa caa gat ttg ttc     436
Leu Ser Ser Ser Ser Ser Pro Phe Val Val Leu Gln Gln Asp Leu Phe
            45                  50                  55 tgg gaa gat gaa gat ctg gtt aca ctc ttc tcc aaa gaa gaa gaa caa     484
Trp Glu Asp Glu Asp Leu Val Thr Leu Phe Ser Lys Glu Glu Glu Gln
        60                  65                  70 gga ctc agc tgt ctc gat gat gtt tat ctt tcc acg gat cga aaa gaa     532
Gly Leu Ser Cys Leu Asp Asp Val Tyr Leu Ser Thr Asp Arg Lys Glu
    75                  80                  85 gct gtt ggt tgg att ctg aga gtc aac gct cat tat ggc ttc tct act     580
Ala Val Gly Trp Ile Leu Arg Val Asn Ala His Tyr Gly Phe Ser Thr
90                  95                 100
```

```
        90               95              100              105
tta gca gct gtt tta gcc ata act tat ctc gat aag ttc atc tgt agc      628
Leu Ala Ala Val Leu Ala Ile Thr Tyr Leu Asp Lys Phe Ile Cys Ser
                110             115              120 tac agc tta cag aga gac aaa cca tgg atg ctt cag ctc gtt tct gtc      676
Tyr Ser Leu Gln Arg Asp Lys Pro Trp Met Leu Gln Leu Val Ser Val
            125             130             135 gcg tgt ctc tca tta gct gct aaa gtc gaa gaa acc caa gtc cct ctt      724
Ala Cys Leu Ser Leu Ala Ala Lys Val Glu Glu Thr Gln Val Pro Leu
        140             145             150 ctt cta gac ttt caa gtg gag gag aca aag tat gtg ttt gaa gca aaa      772
Leu Leu Asp Phe Gln Val Glu Glu Thr Lys Tyr Val Phe Glu Ala Lys
    155             160             165 acc ata cag aga atg gag cta ctg att ctg tct act ctc gag tgg aag      820
Thr Ile Gln Arg Met Glu Leu Leu Ile Leu Ser Thr Leu Glu Trp Lys
170         175             180             185 atg cat ctc att act cca att tcg ttt gta gac cac att atc agg aga      868
Met His Leu Ile Thr Pro Ile Ser Phe Val Asp His Ile Ile Arg Arg
            190             195             200 ttg gga ctt aag aac aat gct cac tgg gat ttc ctc aac aaa tgc cac      916
Leu Gly Leu Lys Asn Asn Ala His Trp Asp Phe Leu Asn Lys Cys His
        205             210             215 cgt ctc ctc ctc tct gta atc tcc gat tca aga ttt gtc ggg tac ctc      964
Arg Leu Leu Leu Ser Val Ile Ser Asp Ser Arg Phe Val Gly Tyr Leu
    220             225             230 cca tca gta gtt gcc gca gct acc atg atg cga att ata gag caa gtt     1012
Pro Ser Val Val Ala Ala Ala Thr Met Met Arg Ile Ile Glu Gln Val
235             240             245 gat ccc ttt gac cct ctt tca tac caa act aat ctc ctc ggt gtc ctt     1060
Asp Pro Phe Asp Pro Leu Ser Tyr Gln Thr Asn Leu Leu Gly Val Leu
250             255             260             265 aac tta acc aag gaa aag gtg aaa act tgc tac gat cta atc ctc caa     1108
Asn Leu Thr Lys Glu Lys Val Lys Thr Cys Tyr Asp Leu Ile Leu Gln
            270             275             280 cta cca gtg gac cgc atc tgt tta cag atc caa atc caa tct tcc aag     1156
Leu Pro Val Asp Arg Ile Cys Leu Gln Ile Gln Ile Gln Ser Ser Lys
        285             290             295 aaa cgc aag agt cac gat tca tca tca tcg ttg aac agt cca agc tgc     1204
Lys Arg Lys Ser His Asp Ser Ser Ser Ser Leu Asn Ser Pro Ser Cys
    300             305             310 gtg att gat gca aac cct ttc aat agc gac gaa agc tca aac gat tcg     1252
Val Ile Asp Ala Asn Pro Phe Asn Ser Asp Glu Ser Ser Asn Asp Ser
315             320             325 tgg tca gcg agt tcg tgc aac cca cca acg tcg tcg tcc ccg cag         1300
Trp Ser Ala Ser Ser Cys Asn Pro Pro Thr Ser Ser Ser Pro Gln
330             335             340             345 caa caa cct cca ttg aag aag atg aga gga gct gaa gag aat gag aag     1348
Gln Gln Pro Pro Leu Lys Lys Met Arg Gly Ala Glu Glu Asn Glu Lys
            350             355             360 aag aag ccg att ttg cat ctg cca tgg gca atc gta gcc act cca taa     1396
Lys Lys Pro Ile Leu His Leu Pro Trp Ala Ile Val Ala Thr Pro
        365             370             375 tcgaaagctc gatttcgttt atatgatatt tactgttttt ttaaactttg agaacaatct   1456
ttgttgtatt aagctttacc cgtttgcata tacgaaatgt cgcgaatcgc cttacgtgcc   1516
atggcttgat agagttaatg ggtaaagggt attcatgaca tttgactgca tgggatgtga   1576
cgaaggagag aattagaaat aataataata atattgcgta aaaaaaaaaa aaaaaa       1632
```

```
<210> SEQ ID NO 32
<211> LENGTH: 376
<212> TYPE: PRT
<213> ORGANISM: Arabidopsis thaliana

<400> SEQUENCE: 32

Met Ala Ile Arg Lys Glu Glu Ser Arg Glu Glu Gln Ser Asn Ser
1               5                   10                  15

Phe Leu Leu Asp Ala Leu Tyr Cys Glu Glu Lys Trp Asp Asp Glu
                20                  25                  30

Gly Glu Glu Val Glu Glu Asn Ser Ser Leu Ser Ser Ser Ser Pro
            35                  40                  45

Phe Val Val Leu Gln Gln Asp Leu Phe Trp Glu Asp Glu Asp Leu Val
    50                  55                  60

Thr Leu Phe Ser Lys Glu Glu Gln Gly Leu Ser Cys Leu Asp Asp
65                  70                  75                  80

Val Tyr Leu Ser Thr Asp Arg Lys Glu Ala Val Gly Trp Ile Leu Arg
                85                  90                  95

Val Asn Ala His Tyr Gly Phe Ser Thr Leu Ala Ala Val Leu Ala Ile
                100                 105                 110

Thr Tyr Leu Asp Lys Phe Ile Cys Ser Tyr Ser Leu Gln Arg Asp Lys
                115                 120                 125

Pro Trp Met Leu Gln Leu Val Ser Val Ala Cys Leu Ser Leu Ala Ala
        130                 135                 140

Lys Val Glu Glu Thr Gln Val Pro Leu Leu Asp Phe Gln Val Glu
145                 150                 155                 160

Glu Thr Lys Tyr Val Phe Glu Ala Lys Thr Ile Gln Arg Met Glu Leu
                165                 170                 175

Leu Ile Leu Ser Thr Leu Glu Trp Lys Met His Leu Ile Thr Pro Ile
                180                 185                 190

Ser Phe Val Asp His Ile Ile Arg Arg Leu Gly Leu Lys Asn Asn Ala
                195                 200                 205

His Trp Asp Phe Leu Asn Lys Cys His Arg Leu Leu Leu Ser Val Ile
        210                 215                 220

Ser Asp Ser Arg Phe Val Gly Tyr Leu Pro Ser Val Val Ala Ala Ala
225                 230                 235                 240

Thr Met Met Arg Ile Ile Glu Gln Val Asp Pro Phe Asp Pro Leu Ser
                245                 250                 255

Tyr Gln Thr Asn Leu Leu Gly Val Leu Asn Leu Thr Lys Glu Lys Val
                260                 265                 270

Lys Thr Cys Tyr Asp Leu Ile Leu Gln Leu Pro Val Asp Arg Ile Cys
        275                 280                 285

Leu Gln Ile Gln Ile Gln Ser Ser Lys Lys Arg Lys Ser His Asp Ser
    290                 295                 300

Ser Ser Ser Leu Asn Ser Pro Ser Cys Val Ile Asp Ala Asn Pro Phe
305                 310                 315                 320

Asn Ser Asp Glu Ser Ser Asn Asp Ser Trp Ser Ala Ser Ser Cys Asn
                325                 330                 335

Pro Pro Thr Ser Ser Ser Pro Gln Gln Gln Pro Pro Leu Lys Lys
                340                 345                 350

Met Arg Gly Ala Glu Glu Asn Glu Lys Lys Pro Ile Leu His Leu
            355                 360                 365

Pro Trp Ala Ile Val Ala Thr Pro
    370                 375
```